(12) United States Patent
Murphy Kessabi et al.

(10) Patent No.: US 7,704,961 B2
(45) Date of Patent: Apr. 27, 2010

(54) AVERMECTINS AND AVERMECTIN MONOSACHARIDES SUBSTITUTED IN THE 4'-AND 4" POSITION HAVING PESTICIDAL PROPERTIES

(75) Inventors: Fiona Murphy Kessabi, Basel (CH); Thomas Pitterna, Basel (CH); Peter Maienfisch, Basel (CH); Jérôme Cassayre, Basel (CH); Laura Quaranta, Basel (CH); Pierre Jung, Basel (CH); Ottmar Franz Hueter, Basel (CH)

(73) Assignee: Merial Limited, Duluth, GA (US)

( * ) Notice: Subject to any disclaimer, the term of this patent is extended or adjusted under 35 U.S.C. 154(b) by 1063 days.

(21) Appl. No.: 10/568,715

(22) PCT Filed: Aug. 27, 2004

(86) PCT No.: PCT/EP2004/009594

§ 371 (c)(1),
(2), (4) Date: Feb. 17, 2006

(87) PCT Pub. No.: WO2005/021569

PCT Pub. Date: Mar. 10, 2005

(65) Prior Publication Data

US 2008/0194498 A1    Aug. 14, 2008

(30) Foreign Application Priority Data

Aug. 28, 2003  (GB)  .................... 0320176.1

(51) Int. Cl.
*A61K 31/70* (2006.01)
*A61K 31/7028* (2006.01)
*C07H 17/08* (2006.01)

(52) U.S. Cl. .............................. 514/30; 514/27; 514/25; 536/7.1; 536/7.2; 536/4.1

(58) Field of Classification Search .................. 514/30, 514/27, 25; 536/7.1, 4.1, 7.2
See application file for complete search history.

(56) References Cited

U.S. PATENT DOCUMENTS 4,203,976 A    5/1980   Fisher et al.

(Continued)

FOREIGN PATENT DOCUMENTS

EP           0 001 688        5/1979

(Continued)

OTHER PUBLICATIONS

Mrozik, H. et al.: "Avermectin acyl derivatives with anthelmintic activity," J. Med Chem., vol. 25, 1982, pp. 658-663, XP0023098565, table II.

(Continued)

*Primary Examiner*—Shaojia Anna Jiang
*Assistant Examiner*—Michael C Henry
(74) *Attorney, Agent, or Firm*—Judy Jarecki-Black; Thomas Kowalski, Esq.; Merial Limited

(57) ABSTRACT

Described is a compound of the formula (I) wherein the bond between carbon atoms 22 and 23 is a single or double bond; m is 0 or 1; $R_1$, is $C_1$-$C_{12}$alkyl, $C_3$-$C_8$cycloalkyl or $C_2$-$C_{12}$alkenyl; and either (A) $R_2$ is $—N(R_3)R_4$, and (1) X is 0, wherein $R_3$ is, for instance, hydrogen, unsubstituted or mono- to pentasubstituted $C_1$-$C_{12}$alkyl, and $R_4$ is, for instance, mono- to pentasubstituted $C_1$-$C_{12}$alkyl, unsubstituted or mono- to pentasubstituted $C_3$-$C_{12}$cycloalkyl; or (2) X is S, wherein $R_3$ is, for instance, hydrogen, unsubstituted or mono- to pentasubstituted $C_1$-$C_{12}$alkyl, and $R_4$ is, for instance, hydrogen, unsubstituted or mono- to pentasubstituted $C_1$-$C_{12}$alkyl; or (3) X is 0 or S, wherein $R_3$ and $R_4$ together are, for instance, a three- to seven membered alkylene or a four- to seven-membered alkenylene bridge; or (B) $R_2$ is $OR_5$, X is 0 or S, wherein $R_5$ is, for instance, $C_1$-$C_{12}$alkyl, mono- to pentasubstituted $C_1$-$C_{12}$alkyl; or, if appropriate, an E/Z isomer, E/Z isomer mixture and/or tautomer thereof, in each case in free form or in salt form; such a compound demonstrates pesticidal activity.

(I)

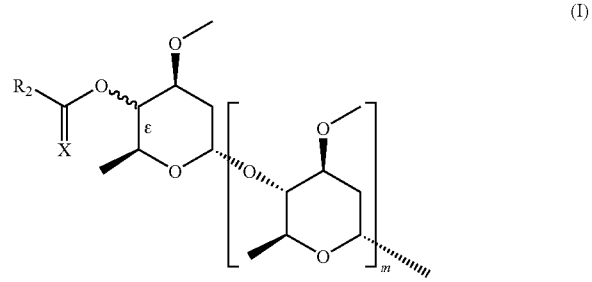

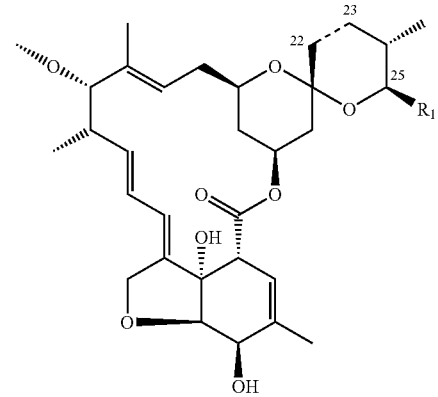

19 Claims, No Drawings

U.S. PATENT DOCUMENTS

| | | | |
|---|---|---|---|
| 4,206,205 | A | 6/1980 | Mrozik et al. |
| 4,427,663 | A | 1/1984 | Mrozik et al. |
| 4,622,313 | A | 11/1986 | Wyvrath, Jr. et al. |
| 4,831,016 | A | 5/1989 | Mrozik et al. |
| 4,895,837 | A | 1/1990 | Mrozik et al. |
| 5,023,241 | A | 6/1991 | Linn et al. |
| 5,057,499 | A | 10/1991 | Mrozik et al. |
| 5,169,839 | A | 12/1992 | Linn et al. |
| 5,192,546 | A | 3/1993 | Abercrombie et al. |
| 5,208,222 | A | 5/1993 | Meinke et al. |
| 5,229,415 | A | 7/1993 | Linn et al. |
| 5,346,698 | A | 9/1994 | Abercrombie |
| 5,362,863 | A | 11/1994 | Cvetovich et al. |
| 5,436,355 | A | 7/1995 | Demchak et al. |
| 5,945,445 | A | 8/1999 | Barringer et al. |
| 5,981,500 | A | 11/1999 | Bishop et al. |
| 6,605,595 | B1 | 8/2003 | Omura et al. |
| 6,875,727 | B2 | 4/2005 | Hofer et al. |
| 6,933,260 | B2 | 8/2005 | Cassayre |
| 7,250,402 | B2 | 7/2007 | Omura et al. |
| 7,378,399 | B2 | 5/2008 | Cassayre et al. |
| 2006/0140997 | A1 | 6/2006 | Pitterna et al. |
| 2006/0205595 | A1 | 9/2006 | Pitterna et al. |
| 2008/0051353 | A1 | 2/2008 | Jung et al. |

FOREIGN PATENT DOCUMENTS

| | | | |
|---|---|---|---|
| EP | 0089202 | | 9/1983 |
| EP | 0001688 | | 3/1988 |
| EP | 0266131 | | 5/1988 |
| EP | 0301806 | | 1/1989 |
| EP | 0340849 | | 11/1989 |
| EP | 0343708 | | 11/1989 |
| EP | 375393 | | 6/1990 |
| EP | 375393 | A1 * | 6/1990 |
| EP | 0411897 | | 6/1991 |
| EP | 0456509 | | 11/1991 |
| EP | 0465121 | | 1/1992 |
| EP | 0506331 | | 9/1992 |
| EP | 0519731 | | 12/1992 |
| EP | 1160252 | | 12/2001 |
| WO | WO 93/15099 | | 8/1993 |
| WO | WO 95/20877 | | 8/1995 |
| WO | WO 96/22300 | | 7/1996 |
| WO | WO 02/068441 | | 9/2002 |
| WO | WO 02/068442 | | 9/2002 |
| WO | WO 03/020738 | | 3/2003 |
| WO | WO 03/053988 | | 7/2003 |
| WO | WO 2004/067534 | | 8/2004 |

OTHER PUBLICATIONS

U.S. Appl. No. 10/560,390, filed Mar. 22, 2006, Pitterna et al.
U.S. Appl. No. 10/544,274, filed Aug. 3, 2005, Cassayare et al.
U.S. Appl. No. 10/544,281, filed Aug. 3, 2005, Quaranta et al.
U.S. Appl. No. 10/543,638, filed Jul. 28, 2005, Pitterna et al.
U.S. Appl. No. 10/543,643, filed Apr. 5, 2006, Pitterna et al.
U.S. Appl. No. 10/543,637, filed Jul. 28, 2005, Pitterna et al.
U.S. Appl. No. 10/513,247, filed Nov. 2, 2004, Tobler et al.
U.S. Appl. No. 10/498,858, filed Jun. 14, 2004, Cassayare et al.
U.S. Appl. No. 10/488,225, filed Feb. 26, 2004, Tobler et al.
U.S. Appl. No. 11/319,686, filed Dec. 28, 2005, Pitterna et al.
U.S. Appl. No. 11/319,687, filed Dec. 28, 2005, Pitterna et al.
U.S. Appl. No. 10/539,274, filed Mar. 9, 2006, Maienfisch et al.
Cvetovich et al. J. Org. Chem., 1994, 59, pp. 7704-7708.
Fisher, American Chemical Society Symposium, 1997, vol. 658, Phytochemicals for Pest Control.
J Med Chem 1992, 35, 3879-3884; "Affinity Probes for the Avermectin Binding Proteins".
Jones, T K et al.; "Synthesis and Biological Activity of 4a,4-Disubstituted Avermectins"; Journal of Agriculture and Food Chemistry, American Chemical Society, 42 1994, p. 1786-1790.
Meinke et al.; "Synthesis of Avermectin B1-4',4'a -Oxide: A Precursor to Potent Antihelmintic Agents", Biorganic Medicinal Chemistry Letters, vol. 2, 1992 p. 537.
Mrozik et al. 4 Deoxy-4-Aminoavermectins With Potent Broad Sprectrum Antiparasitic Activities. Bioorrganic and Medicinal Chem. Letts. vol. 5, No. 20, Oct. 1995, pp. 2435-2440.
Shoop et al.; Efficacy in Sheep and Pharmacokinetics in Cattle that Led to the Selection of Epinomectin as Atopical Endectocide for Cattle, International Journal for Parasitology, 1996, 26 (11), 1227-1235.
Wrzesinski et al; Journal of Agricultural and Food Chemistry, vol. 44, 1996, pp. 304-312.

* cited by examiner

AVERMECTINS AND AVERMECTIN MONOSACHARIDES SUBSTITUTED IN THE 4'-AND 4" POSITION HAVING PESTICIDAL PROPERTIES

This application is a 371 of International Application No. PCT/EP2004/009594 filed Aug. 27, 2004, which claims priority to GB 0320176.1 filed Aug. 28, 2003, the contents of which are incorporated herein by reference.

The invention provides (1) a compound of the formula

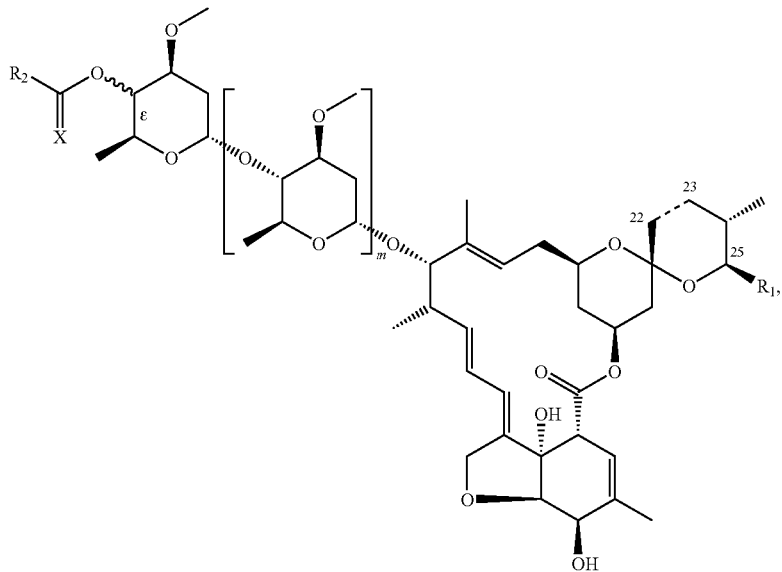

(I)

wherein the bond between carbon atoms 22 and 23 is a single or double bond;

m is 0 or 1;

$R_1$ is $C_1$-$C_{12}$alkyl, $C_3$-$C_8$cycloalkyl or $C_2$-$C_{12}$alkenyl; and either (A) $R_2$ is —$N(R_3)R_4$, and (1) X is O, wherein $R_3$ is hydrogen, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, aryl or heterocyclyl, and $R_4$ is mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted and mono- to trisubstituted heterocyclyl, unsubstituted and mono- to pentasubstituted aryl, $NH_2$, $NHC_1$-$C_{12}$alkyl, $N(C_1$-$C_{12}$alkyl)$_2$, $C_1$-$C_6$alkyl-$N(C_1$-$C_{12}$alkyl)$_2$, —$C_1$-$C_6$alkyl-$N^+(C_1$-$C_{12}$alkyl)$_3$, $SO_2NH_2$, $SO_2NHC_6H_5$, $SO_2$Phenyl, $SO_2$Benzyl, OH, —$OC_1$-$C_{12}$alkyl, —$OC_1$-$OC_{12}$alkenyl or —$OC_1$-$C_{12}$alkynyl; or (2) X is S, wherein $R_3$ is hydrogen, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl; aryl or heterocyclyl, and $R_4$ is hydrogen, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted and mono- to trisubstituted heterocyclyl, unsubstituted and mono- to pentasubstituted aryl, $NH_2$, $NHC_1$-$C_{12}$alkyl, $N(C_1$-$C_{12}$alkyl)$_2$, $SO_2NH_2$, $SO_2NHC_6H_5$, $SO_2$Phenyl, $SO_2$Benzyl, OH or —$OC_1$-$C_{12}$alkyl; or (3) X is O or S, wherein $R_3$ and $R_4$ together are a three- to seven-membered alkylene or a four- to seven-membered alkenylene bridge, in which a $CH_2$ group may be replaced by O, S, C=O or $NR_6$; or (B) $R_2$ is $OR_5$ and X is O or S, wherein $R_5$ is $C_1$-$C_{12}$alkyl, mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl;

in which the substituents of the alkyl-, alkenyl-, alkynyl-, alkylene-, alkenylene-, heterocyclyl-, aryl- and cycloalkyl-radicals mentioned under $R_3$, $R_4$ and $R_5$ are selected from the group consisting of OH, halogen, halo-$C_1$-$C_2$alkyl, CN, SCN, $NO_2$, $C_2$-$C_6$alkynyl, $C_3$-$C_8$cycloalkyl which is unsubstituted or substituted by one to three methyl groups; norbornylenyl; $C_3$-$C_8$cycloalkenyl which is unsubstituted or substituted by one to three methyl groups; $C_3$-$C_8$halocycloalkyl, $C_1$-$C_{12}$alkoxy, $C_1$-$C_{12}$alkoxy$C_1$-$C_{12}$alkoxy, $C_3$-$C_8$cycloalkoxy, $C_1$-$C_{12}$alkylthio, $C_3$-$C_8$cycloalkylthio, $C_1$-$C_{12}$haloalkylthio, $C_1$-$C_{12}$alkylsulfinyl, $C_3$-$C_8$cycloalkylsulfinyl, $C_1$-$C_{12}$haloalkylsulfinyl, $C_3$-$C_8$halocycloalkylsulfinyl, $C_1$-$C_{12}$alkylsulfonyl, $C_3$-$C_8$cycloalkylsulfonyl, $C_1$-$C_{12}$haloalkylsulfonyl, $C_3$-$C_8$halocycloalkylsulfonyl, $C_2$-$C_8$alkenyl, $C_2$-$C_8$alkynyl, —$N(R_6)_2$, wherein the two $R_6$ are independent of each other; —C(=O)$R_7$, —O—C(=O)$R_8$, —NHC(=O)$R_7$, —S—C(=S)$R_8$, —P(=O)(OC$_1$-$C_6$alkyl)$_2$, —S(=O)$_2R_{11}$; —NH—S(=O)$_2R_{11}$, —OC(=O)—$C_1$-$C_6$alkyl-S(=O)$_2R_{11}$; aryl, benzyl, heterocyclyl, aryloxy, benzyloxy, heterocyclyloxy, arylthio, benzylthio, heterocyclylthio; and also aryl, heterocyclyl, aryloxy, benzyloxy, heterocyclyloxy, arylthio, benzylthio or heterocyclylthio which, depending on the possibilities of substitution on the ring, are mono- to pentasubstituted by substituents selected from the group consisting of OH, halogen, CN, NO$_2$, C$_1$-C$_{12}$alkyl, C$_3$-C$_8$cycloalkyl, C$_1$-C$_{12}$haloalkyl, C$_1$-C$_{12}$alkoxy, C$_1$-C$_{12}$haloalkoxy, C$_1$-C$_{12}$alkylthio, C$_1$-C$_{12}$haloalkylthio, C$_1$-C$_6$alkoxy-C$_1$-C$_6$alkyl, dimethylamino-C$_1$-C$_6$alkoxy, C$_2$-C$_8$alkenyl, C$_2$-C$_8$alkynyl, phenoxy, phenyl-C$_1$-C$_6$alkyl, methylenedioxy, —C(=O)R$_7$, —O—C(=O)—R$_8$, —NH—C(=O)R$_8$, —N(R$_{10}$)$_2$, wherein the two R$_{10}$ are independent of each other; C$_1$-C$_6$alkylsulfinyl, C$_3$-C$_8$cycloalkylsulfinyl, C$_1$-C$_6$haloalkylsulfinyl, C$_3$-C$_8$halocycloalkylsulfinyl, C$_1$-C$_6$alkylsulfonyl, C$_3$-C$_8$cycloalkylsulfonyl, C$_1$-C$_6$haloalkylsulfonyl and C$_3$-C$_8$halocycloalkylsulfonyl;

R$_6$ is H, C$_1$-C$_8$alkyl, hydroxy-C$_1$-C$_8$alkyl, C$_3$-C$_8$cycloalkyl, C$_2$-C$_8$alkenyl, C$_2$-C$_8$alkynyl, phenyl, benzyl, —C(=O)R$_7$, or —CH$_2$—C(=O)—R$_7$;

R$_7$ is H, OH, SH, —N(R$_{10}$)$_2$, wherein the two R$_{10}$ are independent of each other; C$_1$-C$_{24}$alkyl, C$_2$-C$_{12}$alkenyl, C$_1$-C$_8$hydroxyalkyl, C$_1$-C$_{12}$haloalkyl, C$_1$-C$_{12}$alkoxy, C$_1$-C$_{12}$haloalkoxy, C$_1$-C$_6$alkoxy-C$_1$-C$_6$alkyl, C$_1$-C$_6$alkoxy-C$_1$-C$_6$alkoxy, C$_1$-C$_6$alkoxy-C$_1$-C$_6$alkoxyC$_1$-C$_6$alkyl, C$_1$-C$_{12}$alkylthio, C$_2$-C$_8$alkenyloxy, C$_2$-C$_8$alkynyloxy, NH—C$_1$-C$_6$alkyl-C(=O)R$_9$, —N(C$_1$-C$_6$alkyl)-C$_1$-C$_6$alkyl-C(=O)—R$_9$, —O—C$_1$-C$_2$alkyl-C(=O)R$_9$, —C$_1$-C$_6$alkyl-S(=O)$_2$R$_9$; aryl, benzyl, heterocyclyl, aryloxy, benzyloxy, heterocyclyloxy; or aryl, benzyl, heterocyclyl, aryloxy, benzyloxy or heterocyclyloxy, which are unsubstituted or mono- to trisubstituted in the ring independently of one another by halogen, nitro, C$_1$-C$_6$alkyl, C$_1$-C$_6$alkoxy, C$_1$-C$_6$haloalkyl or C$_1$-C$_6$haloalkoxy;

R$_8$ is H, C$_1$-C$_{24}$alkyl, C$_1$-C$_{12}$haloalkyl, C$_1$-C$_{12}$hydroxyalkyl, C$_2$-C$_8$alkenyl, C$_2$-C$_8$alkynyl, C$_1$-C$_6$alkoxy-C$_1$-C$_6$alkyl, N(R$_{10}$)$_2$, wherein the two R$_{10}$ are independent of each other; —C$_1$-C$_6$alkyl-C(=O)R$_{10}$, —C$_1$-C$_6$alkyl-S(=O)$_2$R$_9$, aryl, benzyl, heterocyclyl; or aryl, benzyl or heterocyclyl which, depending on the possibilities of substitution on the ring, are mono- to trisubstituted by substituents selected from the group consisting of OH, halogen, CN, NO$_2$, C$_1$-C$_{12}$alkyl, C$_1$-C$_{12}$haloalkyl, C$_1$-C$_{12}$alkoxy, C$_1$-C$_{12}$haloalkoxy, C$_1$-C$_{12}$alkylthio and C$_1$-C$_{12}$haloalkylthio;

R$_9$ is H, OH, C$_1$-C$_{24}$alkyl which is optionally substituted with OH, or —S(=O)$_2$—C$_1$-C$_6$alkyl; C$_1$-C$_{12}$alkenyl, C$_1$-C$_{12}$alkynyl, C$_1$-C$_{12}$alkoxy, C$_1$-C$_6$alkoxy-C$_1$-C$_6$alkyl, C$_1$-C$_6$alkoxy-C$_1$-C$_6$alkoxy, C$_2$-C$_8$alkenyloxy, aryl, aryloxy, benzyloxy, heterocyclyl, heterocyclyloxy or —N(R$_{10}$)$_2$, wherein the two R$_{10}$ are independent of each other;

R$_{10}$ is H, C$_1$-C$_6$alkyl, which is optionally substituted with one to five substituents selected from the group consisting of halogen, C$_1$-C$_6$alkoxy, hydroxy and cyano; C$_1$-C$_8$-cycloalkyl, aryl, benzyl, heterocyclyl; or aryl, benzyl or heterocyclyl, which, depending on the possibilities of substitution on the ring, are mono- to trisubstituted by substituents selected from the group consisting of OH, halogen, CN, NO$_2$, C$_1$-C$_{12}$alkyl, C$_1$-C$_{12}$haloalkyl, C$_1$-C$_{12}$alkoxy, C$_1$-C$_{12}$haloalkoxy, C$_1$-C$_{12}$alkylthio and C$_1$-C$_{12}$haloalkylthio;

or, if appropriate, an E/Z isomer, E/Z isomer mixture and/or tautomer thereof, in each case in free form or in salt form;

a process for preparing these compounds, their isomers and tautomers and the use of these compounds, their isomers and tautomers; pesticidal compositions whose active compound is selected from these compounds and their tautomers; intermediates for the preparation of the said compounds of the formula (I), and a method for controlling pests, especially plant damaging pests, using such compositions.

Hereinbefore and hereinafter, the bond marked by the symbol ⌇ in formula (I) and for formulae (II) to (V) below indicates that at the ε-position (4'- or 4"-position) the S- as well as the R-isomer is meant.

The literature proposes certain macrolide compounds for controlling pests. However, the biological properties of these known compounds are not entirely satisfactory, and, as a consequence, there is still a need for providing further compounds having pesticidal properties, in particular for the control of insects and representatives of the order Acarina. According to the invention, this object is achieved by providing the present compounds of the formula (I).

The compounds claimed according to the invention are derivatives of Avermectin. Avermectins are known to the person skilled in the art. They are a group of structurally closely related pesticidally active compounds which are obtained by fermenting a strain of the microorganism *Streptomyces avermitilis*. Derivatives of Avermectins can be obtained by conventional chemical syntheses.

The Avermectins which can be obtained from *Streptomyces avermitilis* are referred to as A1a, A1b, A2a, A2b, B1a, B1b, B2a and B2b. The compounds referred to as "A" and "B" have a methoxy radical and an OH group, respectively, in the 5-position. The "a" series and the "b" series are compounds in which the substituent R$_1$ (in position 25) is a sec-butyl radical and an isopropyl radical, respectively. The number 1 in the name of the compounds means that atoms 22 and 23 are linked by double bonds; the number 2 means that they are linked by a single bond and that the C atom 23 carries an OH group. The above nomenclature is adhered to in the description of the present invention to denote the specific structure type in the not naturally occurring Avermectin derivatives according to the invention which corresponds to the naturally occurring Avermectin. The present invention makes available derivatives of compounds of the B1 series, in particular mixtures of derivatives of Avermectin B1, especially B1a and B1b, along with derivatives having a single bond between carbon atoms 22 and 23, and derivatives having other substituents in the 25-position, as well as the corresponding monosaccharides.

Some of the compounds of the formula (I) can be present as tautomers. Accordingly, hereinabove and hereinbelow, the compounds of the formula (I) are, if appropriate, also to be understood as including the corresponding tautomers, even if the latter are not specifically mentioned in each case.

The compounds of formula (I) and, where applicable, their tautomers can form salts, for example acid addition salts. These acid addition salts are formed, for example, with strong inorganic acids, such as mineral acids, for example sulfuric acid, a phosphoric acid or a hydrohalic acid, with strong organic carboxylic acids, such as unsubstituted or substituted, for example halo-substituted, C$_1$-C$_4$alkanecarboxylic acids, for example acetic acid, unsaturated or saturated dicarboxylic acids, for example oxalic acid, malonic acid, maleic acid, fumaric acid or phthalic acid, hydroxycarboxylic acids, for example ascorbic acid, lactic acid, malic acid, tartaric acid or citric acid, or benzoic acid, or with organic sulfonic acids, such as unsubstituted or substituted, for example halo-substituted, C$_1$-C$_4$alkane- or aryl-sulfonic acids, for example methane- or p-toluene-sulfonic acid. Compounds of formula (I) that have at least one acidic group can furthermore form salts with bases. Suitable salts with bases are, for example, metal salts, such as alkali metal salts or alkaline earth metal salts, for example, sodium, potassium or magnesium salts, or salts with ammonia or with an organic amine, such as morpholine, piperidine, pyrrolidine, a mono-, di- or tri-lower alkylamine, for example, ethylamine, diethylamine, triethylamine or dimethylpropylamine, or a mono-, di- or trihydroxy-lower alkylamine, for example, mono-, di- or tri-ethanolamine. Corresponding internal salts may also be formed where appropriate. The free form is preferred. Among the salts of the compounds of formula (I), the agrochemically advantageous salts are preferred. Hereinbefore and hereinafter, any reference to the free compounds of formula (I) or their salts is to be understood as including, where appropriate, also the corresponding salts or the free compounds of formula (I), respectively. The same applies to tautomers of compounds of formula (I) and salts thereof.

Unless defined otherwise, the general terms used hereinabove and hereinbelow have the meanings given below.

Unless defined otherwise, carbon-containing groups contain in each case 1 up to and including 6, preferably 1 up to and including 4, in particular 1 or 2, carbon atoms.

Halogen—as a group per se and also as a structural element of other groups and compounds, such as haloalkyl, haloalkoxy and haloalkylthio—is fluorine, chlorine, bromine or iodine, in particular fluorine, chlorine or bromine, especially fluorine or chlorine.

Alkyl—as a group per se and also as a structural element of other groups and compounds, such as haloalkyl, alkoxy and alkylthio—is, in each case taking into account the number of carbon atoms contained in each case in the group or compound in question, either straight-chain, i.e. methyl, ethyl, propyl, butyl, pentyl, hexyl, heptyl or octyl, or branched, for example isopropyl, isobutyl, sec-butyl, tert-butyl, isopentyl, neopentyl or isohexyl. Preferred number of carbon atoms in an alkyl group is between 1 to 6, such as 1 to 4.

Cycloalkyl—as a group per se and also as a structural element of other groups and compounds, such as, for example, of halocycloalkyl, cycloalkoxy and cycloalkylthio—is, in each case taking into account the number of carbon atoms contained in each case in the group or compound in question, cyclopropyl, cyclobutyl, cyclopentyl, cyclohexyl, cycloheptyl or cyclooctyl. Preferred number of carbon atoms in a cycloalkyl group is between 3 to 6, such as 3 to 4.

Alkenyl—as a group per se and also as a structural element of other groups and compounds—is, taking into account the number of carbon atoms and conjugated or isolated double bonds contained in the group, either straight-chain, for example vinyl, allyl, 2-butenyl, 3-pentenyl, 1-hexenyl, 1-heptenyl, 1,3-hexadienyl or 1,3-octadienyl, or branched, for example isopropenyl, isobutenyl, isoprenyl, tert-pentenyl, isohexenyl, isoheptenyl or isooctenyl. Preference is given to alkenyl groups having 3 to 12, in particular 3 to 6, especially 3 or 4, carbon atoms.

Alkynyl—as a group per se and also as a structural element of other groups and compounds—is, in each case taking into account the number of carbon atoms and conjugated or isolated double bonds contained in the group or compound in question, either straight-chain, for example ethynyl, propargyl, 2-butynyl, 3-pentynyl, 1-hexynyl, 1-heptynyl, 3-hexen-1-ynyl or 1,5-heptadien-3-ynyl, or branched, for example 3-methylbut-1-ynyl, 4-ethylpent-1-ynyl, 4-methylhex-2-ynyl or 2-methylhept-3-ynyl. Preference is given to alkynyl groups having 3 to 12, in particular 3 to 6, especially 3 or 4, carbon atoms.

Halogen-substituted carbon-containing groups and compounds, such as, for example, halogen-substituted alkyl, alkenyl, alkynyl, cycloalkyl, alkoxy or alkylthio, can be partially halogenated or perhalogenated, where in the case of polyhalogenation the halogen substituents can be identical or different. Examples of haloalkyl—as a group per se and also as a structural element of other groups and compounds, such as haloalkoxy or haloalkylthio—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl which is mono- to heptasubstituted by fluorine, chlorine and/ or bromine, such as $CH_2CHBrCH_2Br$, $CF_2CHFCF_3$, $CH_2CF_2CF_3$, $CF(CF_3)_2$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; pentyl or one of its isomers, mono- to undecasubstituted by fluorine, chlorine and/or bromine, such as $CF(CF_3)(CHF_2)CF_3$ or $CH_2(CF_2)_3CF_3$; and hexyl or one of its isomers, mono- to tridecasubstituted by fluorine, chlorine and/or bromine, such as $(CH_2)_4$—$CHBrCH_2Br$, $CF_2(CHF)_4CF_3$, $CH_2(CF_2)_4CF_3$ or $C(CF_3)_2(CHF)_2CF_3$.

Aryl is in particular phenyl, naphthyl, anthracenyl, phenanthrenyl, perylenyl or fluorenyl, preferably phenyl.

Heterocyclyl is understood as being a three- to seven-membered monocyclic ring, which may be saturated or unsaturated, and that contains from one to three hetero atoms selected from the group consisting of N, O and S, especially N and S; or a bicyclic ring-system having from 8 to 14 ring atoms, which may be saturated or unsaturated, and that may contain either in only one ring or in both rings independently of one another, one or two hetero atoms selected from N, O and S; heterocyclyl is in particular piperidinyl, piperazinyl, oxiranyl, morpholinyl, thiomorpholinyl, pyridyl, N-oxidopyridinio, pyrimidyl, pyrazinyl, s-triazinyl, 1,2,4-triazinyl, thienyl, furanyl, dihydrofuranyl, tetrahydrofuranyl, pyranyl, tetrahydropyranyl, pyrrolyl, pyrrolinyl, pyrrolidinyl, pyrazolyl, imidazolyl, imidazolinyl, thiazolyl, isothiazolyl, triazolyl, oxazolyl, thiadiazolyl, thiazolinyl, thiazolidinyl, oxadiazolyl, dioxaborolanyl, phthalimidoyl, benzothienyl, quinolinyl, quinoxalinyl, benzofuranyl, benzimidazolyl, benzpyrrolyl, benzthiazolyl, indolinyl, isoindolinyl, cumarinyl, indazolyl, benzothiophenyl, benzofuranyl, pteridinyl or purinyl, which are preferably attached via a C atom; thienyl, benzofuranyl, benzothiazolyl, tetrahydropyranyl, dioxaborolanyl, or indolyl is preferred; in particular dioxaborolanyl, pyridyl or thiazolyl. The said heterocyclyl radicals may preferrably be unsubstituted or—depending on the substitution possibilities on the ring system—substituted by 1 to 3 substituents selected from the group consisting of halogen, =O, —OH, =S, SH, nitro, $C_1$-$C_6$alkyl, $C_1$-$C_6$hydroxyalkyl, $C_1$-$C_6$alkoxy, $C_1$-$C_6$haloalkyl, $C_1$-$C_6$haloalkoxy, phenyl and benzyl.

In the context of the present invention, preference is given to (2) compounds according to group (1) of the formula (I) in which $R_1$ is isopropyl or sec-butyl, preferably to those in which a mixture of the isopropyl and the sec-butyl derivative is present;

(3) compounds according to group (1) of the formula (I) in which $R_1$ is cyclohexyl;

(4) compounds according to group (1) of the formula (I) in which $R_1$ is 1-methyl-butyl;

(5) compounds according to anyone of groups (1) to (4) of formula (I), in which the bond between the bond between carbon atoms 22 and 22 is a single bond;

(6) compounds according to anyone of the groups (1) to (4) of formula (I), in which atoms the bond between carbon atoms 22 and 23 is a double bond;

(7) compounds according to anyone of the groups (1) to (6) of formula (I), in which m is 0;

(8) compounds according to anyone of the groups (1) or (6) of formula (I), in which m is 1;

(9) compounds according to anyone of the groups (1) to (8) of the formula (I) in which the configuration at the ϵ-position is (R);

(10) compounds according to anyone of the groups (1) to (8) of the formula (I) in which the configuration at the ϵ-position is (S);

(11) compounds according to anyone of the groups (1) to (10) of the formula (I) in which X is O;

(12) compounds according to anyone of the groups (1) to (10) of the formula (I) in which X is S;

(13) compounds according to anyone of the groups (1) to (12) of the formula (I) in which $R_2$ is —N($R_3$)$R_4$, $R_3$ is hydrogen and $R_4$ is mono- to trisubstituted $C_1$-$C_{12}$alkyl or unsubstituted or mono- to pentasubstituted $C_3$-$C_{12}$cycloalkyl;

(14) compounds according to anyone of the groups (1) to (12) of formula (I), in which $R_2$ is $OR_5$ and $R_5$ is $C_1$-$C_{12}$alkyl, $C_3$-$C_{12}$cycloalkyl or $C_2$-$C_{12}$alkenyl.

A further aspect of the invention is a compound of formula (I), wherein $R_1$ is as defined for formula (I) under (1), m is 0 or 1, the bond between carbon atoms 22 and 23 is a single or a double bond, X is O, $R_2$ is —N($R_3$)$R_4$ and $R_3$ and $R_4$ are H or $C_1$-$C_{12}$alkyl, especially wherein $R_3$ is H and $R_4$ is $C_1$-$C_6$-alkyl.

In the context of the invention, particular preference is given to the compounds of the formula (I) listed in the tables and, if appropriate, to their E/Z isomers and E/Z isomer mixtures.

The invention also provides a process for preparing the compounds of the formula and which is known or can be prepared according to known procedures, wherein $R_1$ and m have the meanings as given in formula (I) and R is a protecting group, is converted with 1,1'-carbonyldiimidazole or 1,1'-thiocarbonyldiimidazole into a compound of the formula

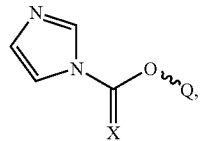

(III)

wherein Q has the same meaning as the part of the formula (II) which is in the bracket marked with Q, and X is O or S ("acylation");

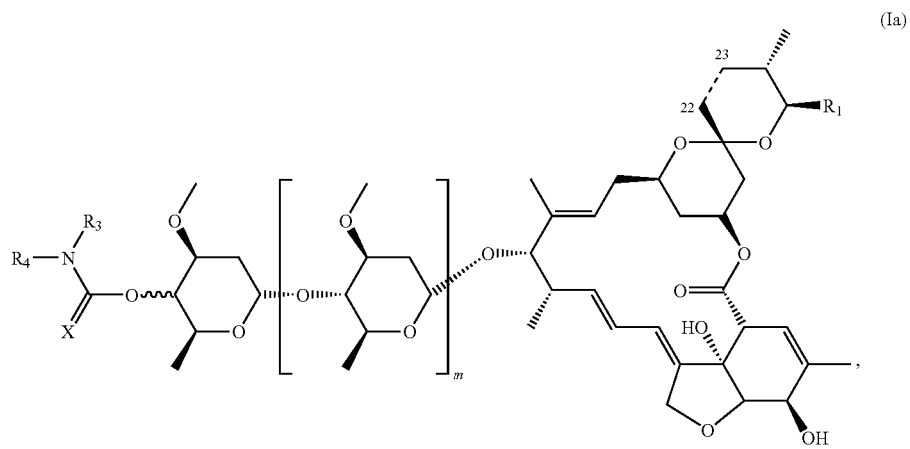

(Ia)

and, if appropriate, tautomers thereof, wherein $R_1$, $R_3$, $R_4$, X and m have the same meanings as given above under (1) for formula (I), and the bond between carbon atoms 22 and 23 is a single or double bond, wherein (A) a compound of the formula

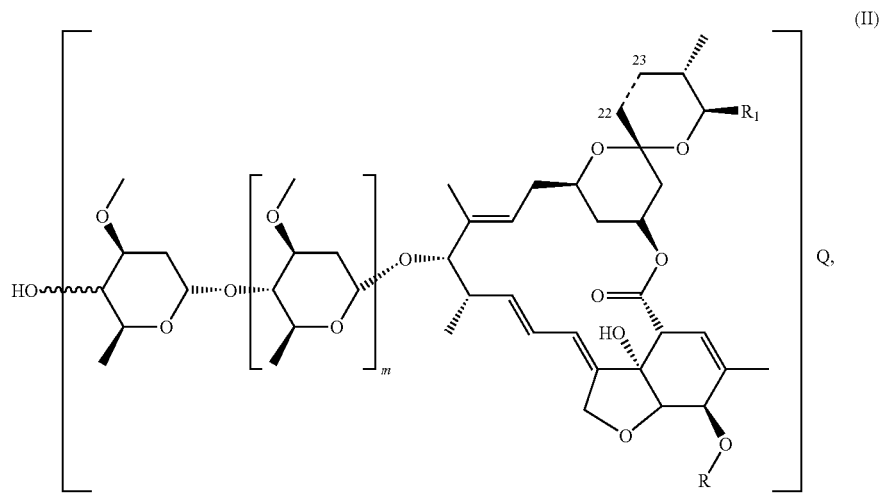

(II)

(B) a compound of the formula (IV) is prepared

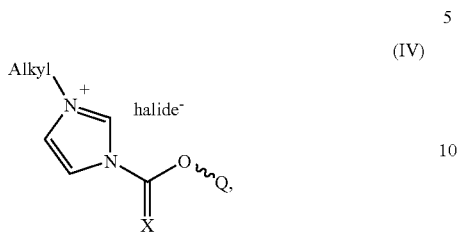
(IV)

wherein X and Q have the same meanings as given for formula (III), by reacting a compound of the formula (III) with a haloalkane, preferably iodomethane ("activation");

(C) a compound of the formula (V) is prepared

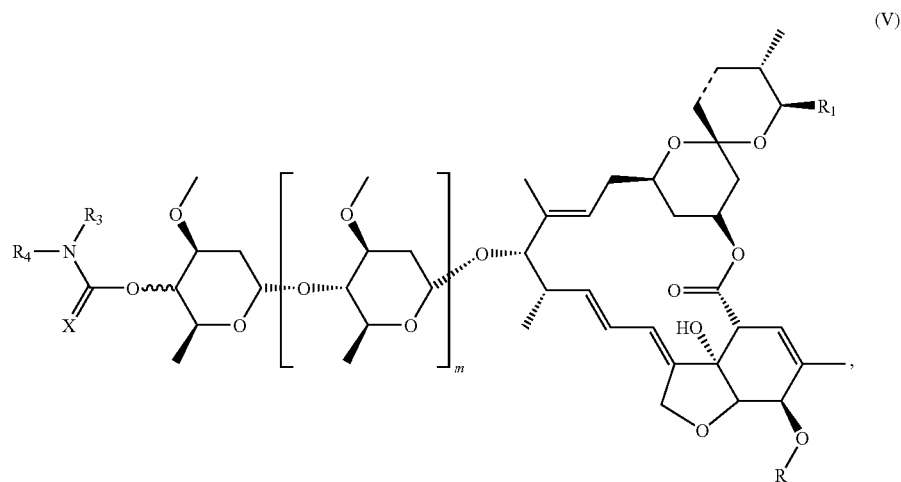
(V)

wherein $R_1$, m, $R_3$, $R_4$ and X have the same meanings as given for formula (I), and the bond between carbon atoms 22 and 23 is a single or double bond, and R is a protecting group as in formula (II), by reacting a compound of the formula (IV) with a compound of the formula $HN(R_3)R_4$, wherein $R_3$, $R_4$ and X have the same meanings as given for formula (I) ("amination"); and (D) the said compound of the formula (V) is deprotected.
The invention also provides
(E) a process for preparing the compounds of the formula wherein X is O, with a compound of the formula R₅OH in the presence of an acid, preferably methanesulphonic acid, provides compounds of formula (Ib) directly, where X=O.

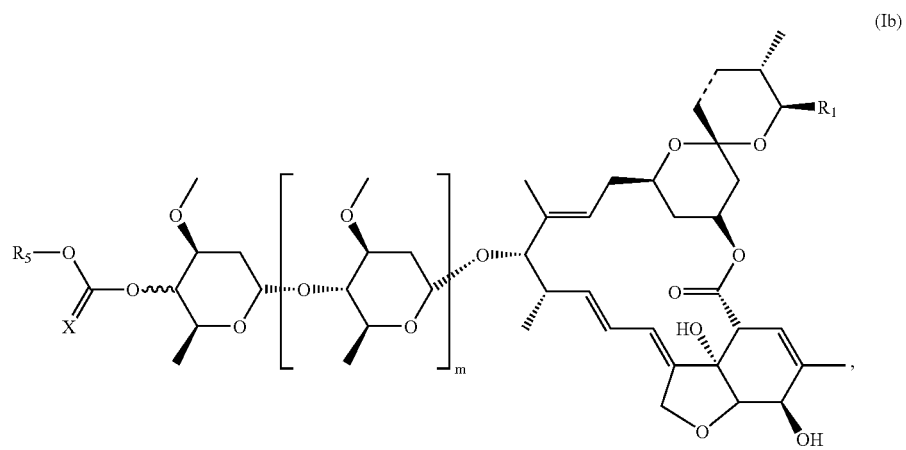

and, if appropriate, tautomers thereof, wherein $R_1$, $R_5$, X and m have the same meanings as given above under (1) for formula (I), and the bond between carbon atoms 22 and 23 is a single or double bond, wherein
a compound of the above formula (IV) is reacted with a compound of the formula $R_5$—OH, wherein $R_5$ has the same meanings as given above under (1) for formula (I), and the resulting compound is deprotected in analogy to step (D).

In an alternative variant of the above process for the preparation of the compound of the formula (Ia), the deprotection step (D) can be carried out before the "activation" step (B). The "amination" step (C) will then be carried out with the compound of the formula (IV) not having a protecting group in the 5-position.

Likewise, the activating step (B) can be omitted completely, that is to say the compound of the formula (III) is either first according to step (C) converted directly into compound (V) and the said compound (V) then deprotected according to step (D), or compound (III) is first deprotected and then in analogy to step (C) converted into a compound (Ia).

In an alternative variant for the preparation of the compound of the formula (Ia), wherein $R_3$ is H and $R_4$ is as defined above, a compound of the formula (II) is reacted with a compound of the formula $R_4N=C=X$, wherein X is O or S, and the resulting compound is deprotected in analogy to step (D).

In an additional variant for the preparation of the compound of the formula (Ia), wherein $R_3$ and $R_4$ are as defined above, a compound of the formula (II) is reacted with a compound of the formula $R_3R_4N(C=X)Cl$, wherein X is O or S, and the resulting compound is deprotected in analogy to step (D).

In an alternative variant of the above process for the preparation of the compound of the formula (Ib), the deprotection step (D) can be carried out before the "activation" step (B). The reaction with a compound of the formula $R_5OH$ (step (E)) will then be carried out with the compound of the formula (IV) not having a protecting group in the 5-position.

In another alternative of the above process for the preparation of compounds (Ib), the activating step can be omitted completely and the reaction of the compound of formula (III), In an additional variant for the preparation of the compound of formula (Ib), where X=O, a compound of the formula (II) is reacted with a compound of the formula $R_5OCOCl$ or of the formula $R_{50}(C=O)O(C=O)OR_5$, wherein $R_5$ has the same meanings as defined for formula (I), and the resulting compound is deprotected in analogy to step (D).

The comments made above in connection with tautomers of compounds of formula (I) apply analogously to the starting materials mentioned hereinabove and hereinbelow in respect of their tautomers and diasteromers.

The reactions described hereinabove and hereinbelow are carried out in a manner known per se, for example in the absence or, customarily, in the presence of a suitable solvent or diluent or of a mixture thereof, the reactions being carried out, as required, with cooling, at room temperature or with heating, for example in a temperature range of approximately from −80° C. to the boiling temperature of the reaction medium, preferably from approximately 0° C. to approximately +150° C., and, if necessary, in a closed vessel, under pressure, under an inert gas atmosphere and/or under anhydrous conditions. Especially advantageous reaction conditions can be found in the Examples. The reaction time is not critical; a reaction time of from about 0.1 to about 24 hours, especially from about 0.5 to about 10 hours, is preferred.

The product is isolated by customary methods, for example by means of filtration, crystallization, distillation or chromatography, or any suitable combination of such methods.

Protecting groups are as defined for instance in the compounds of formulae (II), (III), (IV) and (V) include: alkyl ether radicals, such as methoxymethyl, methylthiomethyl, tert-butylthiomethyl, benzyloxymethyl, p-methoxybenzyl, 2-methoxyethoxymethyl, 2,2,2-trichloroethoxymethyl, 2-(trimethylsilyl)ethoxymethyl, tetrahydropyranyl, tetrahydrofuranyl, 1-ethoxyethyl, 1-(2-chloroethoxy)ethyl, 1-methyl-1-methoxyethyl, 1-methyl-1-benzyloxyethyl, trichloroethyl, 2-trimethylsilylethyl, tert-butyl, allyl, p-methoxyphenyl, 2,4-dinitrophenyl, benzyl, p-methoxybenzyl, o-nitrobenzyl, p-nitrobenzyl, triphenylmethyl; trialkylsilyl radicals, such as trimethylsilyl, triethylsilyl, dimethyl-tert-butylsilyl, dimethyl-isopropylsilyl, dimethyl-1,1,2-trimethylpropylsilyl, diethyl-isopropylsilyl, dimethyl-terthexylsilyl, but also phenyl-tert-alkylsilyl groups, such as diphenyl-tert-butylsilyl; esters, such as formates, acetates, chloroacetates, dichloroacetates, trichloroacetates, trifluoroacetates, methoxyacetates, phenoxyacetates, pivaloates, benzoates; alkyl carbonates, such as methyl-, 9-fluorenylmethyl-, ethyl-, 2,2,2-trichloroethyl-, 2-(trimethylsilyl)ethyl-, vinyl-, allyl-, benzyl-, p-methoxybenzyl-, o-nitrobenzyl-, p-nitrobenzyl-, but also p-nitrophenyl-carbonate.

Preference is given to trialkylsilyl radicals, such as trimethylsilyl, triethylsilyl, dimethyl-tert-butylsilyl, diphenyl-tert-butylsilyl, esters, such as methoxyacetates and phenoxyacetates, and carbonates, such as 9-fluorenylmethylcarbonates and allylcarbonates. Dimethyl-tert-butylsilyl ether is especially preferred.

The starting materials mentioned hereinabove and hereinbelow that are used for the preparation of the compounds of formula (I) and, where applicable, their tautomers are known or can be prepared by methods known per se, e.g. as indicated below.

The compounds of formulae (III) to (V) are also an aspect of the present invention. The compounds (III) to (V) have either a protecting group on the oxygen atom at the 5-position, or alternatively are deprotected. The compounds of the formula (I) and of the formulae (III) to (V) in both the protected and deprotected form are valuable intermediates for the synthesis of compounds of formula (I), and can be prepared by methods known per se. The use of compounds of formula (II) and of the formulae (III) to (V) in both the protected and deprotected form for the synthesis of compounds of formula (I) are also a subject of this invention. The preferences for the substituents are the same as defined for the compound of the formula (I) in sections (2) to (14).

Process Variant (A):

Examples of solvents and diluents include: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; esters of carboxylic acids, such as ethyl acetate; amides, such as dimethylformamide, dimethylacetamide or 1-methyl-2-pyrrolidinones; nitriles, such as acetonitrile; sulfoxides, such as dimethyl sulfoxide; or mixtures of the mentioned solvents. Preference is given to amides, such as dimethylformamide and dimethylacetamide, especially dimethylacetamide.

The reactions are advantageously carried out in a temperature range of from approximately −70° C. to 50° C., preferably at from −10° C. to 25° C.

Especially preferred conditions for the reaction are described in Examples P.1 (step A) and P.7 (step A).

Process Variant (B):

Examples of solvents and diluents are the same as those mentioned under Process variant A. In particular, nitriles, such as acetonitrile are especially suitable.

The reactions are advantageously carried out in a temperature range of from approximately −70° C. to 50° C., preferably at from −10° C. to 25° C.

Especially preferred conditions for the reaction are described in Examples P.1 (step C) and P.7 (step C).

Process Variant (C):

Examples of solvents and diluents are the same as those mentioned under Process variant A.

The reactions are advantageously carried out in a temperature range of from approximately −70° C. to 60° C., preferably at from 0° C. to 25° C.

Especially preferred conditions for the reaction are described in Examples P.1 (step D), P.4 (step D) and P.7 (step D).

Process Variant (D):

Examples of solvents and diluents are the same as those mentioned under Process variant A. In addition, alcohols, such as methanol, ethanol or 2-propanol, and water are suitable.

The reactions are advantageously carried out in a temperature range of approximately from −70° C. to 100° C., preferably at from −10° C. to 25° C.

Suitable for the removal of the protecting group are Lewis acids, such as hydrochloric acid, methanesulfonic acid, $BF_3.OEt_2$, HF in pyridine, $Zn(BF_4)_2,H_2O$, p-toluenesulfonic acid, $AlCl_3$, $HgCl_2$; ammonium fluoride, such as tetrabutylammonium fluoride; bases, such as ammonia, trialkylamine or heterocyclic bases; hydrogenolysis with a catalyst, such as palladium-on-carbon; reducing agents, such as sodium borohydride or tributyltin hydride with a catalyst, such as $Pd(PPh_3)_4$, or also zinc with acetic acid.

Preference is given to acids, such as methanesulfonic acid or HF in pyridine; sodium borohydride with Pd(0); bases, such as ammonia, triethylamine or pyridine; especially acids, such as HF in pyridine or methanesulfonic acid.

Especially preferred conditions for the reaction are described in Examples P.1 (step B), P.4 (step E), P.6 (step B) and P.10 (step C).

Process Variant (E):

Examples of solvents and diluents are the same as those mentioned under Process variant A.

The reactions are advantageously carried out in a temperature range of from approximately −70° C. to 60° C., preferably at from 0° C. to 25° C.

Especially preferred conditions for the reaction are described in Examples P.21 (step A) and P.22.

The compounds of formula (I) may be in the form of one of the possible isomers or in the form of a mixture thereof, in the form of pure isomers or in the form of an isomeric mixture, i.e. in the form of a diastereomeric mixture; the invention relates both to the pure isomers and to the diastereomeric mixtures and is to be interpreted accordingly hereinabove and hereinbelow, even if stereochemical details are not mentioned specifically in every case.

The diastereomeric mixtures can be resolved into the pure isomers by known methods, for example by recrystallisation from a solvent, by chromatography, for example high pressure liquid chromatography (HPLC) on acetylcellulose, with the aid of suitable microorganisms, by cleavage with specific, immobilised enzymes, or via the formation of inclusion compounds, for example using crown ethers, only one isomer being complexed.

Apart from by separation of corresponding mixtures of isomers, pure diastereoisomers can be obtained according to the invention also by generally known methods of stereoselective synthesis, for example by carrying out the process according to the invention using starting materials having correspondingly suitable stereochemistry.

In each case it may be advantageous to isolate or synthesise the biologically more active isomer, where the individual components have different biological activity.

The compounds of formula (I) may also be obtained in the form of their hydrates and/or may include other solvents, for example solvents which may have been used for the crystallisation of compounds in solid form.

The invention relates to all those embodiments of the process according to which a compound obtainable as starting material or intermediate at any stage of the process is used as starting material and some or all of the remaining steps are carried out or a starting material is used in the form of a derivative or salt and/or its racemates or antipodes or, especially, is formed under the reaction conditions.

In the processes of the present invention it is preferable to use those starting materials and intermediates which result in the compounds of formula (I) that are especially preferred.

The invention relates especially to the preparation processes described in any one of Examples P.1 to P.20.

In the area of pest control, the compounds of formula (I) according to the invention are active ingredients exhibiting valuable preventive and/or curative activity with a very advantageous biocidal spectrum and a very broad spectrum, even at low rates of concentration, while being well tolerated by warm-blooded animals, fish and plants. They are, surprisingly, equally suitable for controlling both plant pests and ecto- and endo-parasites in humans and more especially in productive livestock, domestic animals and pets. They are effective against all or individual development stages of normally sensitive animal pests, but also of resistant animal pests, such as insects and representatives of the order Acarina, nematodes, cestodes and trematodes, while at the same time protecting useful organisms. The insecticidal or acaricidal activity of the active ingredients according to the invention may manifest itself directly, i.e. in the mortality of the pests, which occurs immediately or only after some time, for example during moulting, or indirectly, for example in reduced oviposition and/or hatching rate, good activity corresponding to a mortality of at least 50 to 60%.

Successful control within the scope of the subject of the invention is possible, in particular, of pests from the orders Lepidoptera, Coleoptera, Orthoptera, Isoptera, Psocoptera, Anoplura, Mallophaga, Thysanoptera, Heteroptera, Homoptera, Hymenoptera, Diptera, Siphonaptera, Thysanura and Acarina, mainly Lepidoptera and Coleoptera. Very especially good control is possible of the following pests:

*Abagrotis* spp., *Abraxas* spp., *Acantholeucania* spp., *Acanthoplusia* spp., *Acarus* spp., *Acarus siro*, *Aceria* spp., *Aceria sheldoni*, *Acleris* spp., *Acoloithus* spp., *Acompsia* spp., *Acossus* spp., *Acria* spp., *Acrobasis* spp., *Acrocercops* spp., *Acrolepia* spp., *Acrolepiopsis* spp., *Acronicta* spp., *Acropolitis* spp., *Actebia* spp., *Aculus* spp., *Aculus schlechtendali*, *Adoxophyes* spp., *Adoxophyes reticulana*, *Aedes* spp., *Aegeria* spp., *Aethes* spp., *Agapeta* spp., *Agonopterix* spp., *Agriopis* spp., *Agriotes* spp., *Agriphila* spp., *Agrochola* spp., *Agroperina* spp., *Alabama* ssp., *Alabama argillaceae*, *Agrotis* spp., *Albuna* spp., *Alcathoe* spp., *Alcis* spp., *Aleimma* spp., *Aletia* spp., *Aleurothrixus* spp., *Aleurothrixus floccosus*, *Aleyrodes* spp., *Aleyrodes brassicae*, *Allophyes* spp., *Alsophila* spp., *Amata* spp., *Amathes* spp., *Amblyomma* spp., *Amblyptilia* spp., *Ammoconia* spp., *Amorbia* spp., *Amphion* spp., *Amphipoea* spp., *Amphipyra* spp., *Amyelois* spp., *Anacamptodes* spp., *Anagrapha* spp., *Anarsia* spp., *Anatrychyntis* spp., *Anavitrinella* spp., *Ancylis* spp., *Andropolia* spp., *Anhimella* spp., *Antheraea* spp., *Antherigona* spp., *Antherigona soccata*, *Anthonomus* ssp., *Anthonomus grandis*, *Anticarsia* spp., *Anticarsia gemmatalis*, *Aonidiella* spp., *Apamea* spp., *Aphania* spp., *Aphelia* spp., Aphididae, *Aphis* spp., *Apotomis* spp., *Aproaerema* spp., *Archippus* spp., *Archips* spp., Acromyrmex, *Arctia* spp., *Argas* spp., *Argolamprotes* spp., *Argyresthia* spp., *Argyrogramma* spp., *Argyroploce* spp., *Argyrotaenia* spp., *Arotrophora* spp., *Ascotis* spp., *Aspidiotus* spp., *Aspilapteryx* spp., *Asthenoptycha* spp., *Aterpia* spp., *Athetis* spp., *Atomaria* spp., *Atomaria linearis*, *Atta* spp., *Atypha* spp., *Autographa* spp., *Axylia* spp., *Bactra* spp., *Barbara* spp., *Batrachedra* spp., *Battaristis* spp., *Bembecia* spp., *Bemisia* spp., *Bemisia tabaci*, *Bibio* spp., *Bibio hortulanis*, *Bisigna* spp., *Blastesthia* spp., *Blatta* spp., *Blatella* spp., *Blepharosis* spp., *Bleptina* spp., *Boarmia* spp., *Bombyx* spp., *Bomolocha* spp., *Boophilus* spp., *Brachmia* spp., *Bradina* spp., *Brevipalpus* spp., *Brithys* spp., *Bryobia* spp., *Bryobia praetiosa*, *Bryotropha* spp., *Bupalus* spp., *Busseola* spp., *Busseola fusca*, *Cabera* spp., *Cacoecimorpha* spp., *Cadra* spp., *Cadra cautella*, *Caenurgina* spp., *Calipitrimerus* spp., *Callierges* spp., *Callophpora* spp., *Callophpora erythrocephala*, *Calophasia* spp., *Caloptilia* spp., *Calybites* spp., *Capnoptycha* spp., *Capua* spp., *Caradrina* spp., *Caripeta* spp., *Carmenta* spp., *Carposina* spp., *Carposina nipponensis*, *Catamacta* spp., *Catelaphris* spp., *Catoptria* spp., *Caustoloma* spp., *Celaena* spp., *Celypha* spp., *Cenopis* spp., *Cephus* spp., *Ceramica* spp., *Cerapteryx* spp., *Ceratitis* spp, *Ceratophyllus* spp., *Ceroplaster* spp., *Chaetocnema* spp., *Chaetocnema tibialis*, *Chamaesphecia* spp., *Charanvca* spp., *Chemophila* spp., *Chersotis* spp., *Chiasmia* spp., *Chilo* spp., *Chionodes* spp., *Chorioptes* spp., *Choristoneura* spp., *Chrysaspidia* spp., *Chrysodeixis* spp., *Chrysomya* spp., *Chrysomphalus* spp., *Chrysomphalus dictyospermi*, *Chrysomphalus aonidium*, *Chrysoteuchia* spp., *Cilix* spp., *Cimex* spp., *Clysia* spp., *Clysia ambiguella*, *Clepsis* spp., *Cnaemidophorus* spp., *Cnaphalocrocis* spp., *Cnephasia* spp., *Coccus* spp., *Coccus hesperidum*, *Cochylis* spp., *Coleophora* spp., *Colotois* spp., *Commophila* spp., *Conistra* spp., *Conopomorpha* spp., *Corcyra* spp., *Cornutiplusia* spp., *Cosmia* spp., *Cosmopolites* spp., *Cosmopterix* spp., *Cossus* spp., *Costaeonvexa* spp., *Crambus* spp., *Creatonotos* spp., *Crocidolomia* spp., *Crocidolomia binotalis*, *Croesia* spp., *Crymodes* spp., *Cryptaspasma* spp., *Cryptoblabes* spp., *Cryptocala* spp., *Cryptophlebia* spp., *Cryptophlebia leucotreta*, *Cryptoptila* spp., *Ctenopseustis* spp., *Cucullia* spp., *Curculio* spp., *Culex* spp., *Cuterebra* spp., *Cydia* spp., *Cydia pomonella*, *Cymbalophora* spp., *Dactylethra* spp., *Dacus* spp., *Dadica* spp., *Damalinea* spp., *Dasychira* spp., *Decadarchis* spp., *Decodes* spp., *Deilephila* spp., *Deltodes* spp., *Dendrolimus* spp., *Depressaria* spp., *Dermestes* spp., *Dermanyssus* spp., *Dermanyssus gallinae*, *Diabrotica* spp., *Diachrysia* spp., *Diaphania* spp., *Diarsia* spp., *Diasemia* spp., *Diatraea* spp., *Diceratura* spp., *Dichomeris* spp., *Dichrocrocis* spp., *Dichrorampha* spp., *Dicycla* spp., *Dioryctria* spp., *Diparopsis* spp., *Diparopsis castanea*, *Dipleurina* spp., *Diprion* spp., Diprionidae, *Discestra* spp., *Distantiella* spp., *Distantiella theobroma*, *Ditula* spp., *Diurnea* spp., *Doratopteryx* spp., *Drepana* spp., *Drosphila* spp., *Drosphila melanogaster*, *Dysauxes* spp., *Dysdercus* spp., *Dysstroma* spp., *Eana* spp., *Earias* spp., *Ecclitica* spp., *Ecdytolopha* spp., *Ecpyrrhorrhoe* spp., *Ectomyelois* spp., *Eetropis* spp., *Egira* spp., *Elasmopalpus* spp., *Emmelia* spp., mpoasca spp., *Empyreuma* spp., *Enargia* spp., *Enarmonia* spp., *Endopiza* spp., *Endothenia* spp., *Endotricha* spp., *Eoreuma* spp., *Eotetranychus* spp., *Eotetranychus carpini*, *Epagoge* spp., *Epelis* spp., *Ephestia* spp., *Ephestiodes* spp., *Epiblema* spp., *Epiehoristodes* spp., *Epinotia* spp., *Epiphyas* spp., *Epiplema* spp., *Epipsestis* spp., *Epirrhoe* spp., *Episimus* spp., *Epitymbia* spp., *Epilachna* spp., *Erannis* spp., *Erastria* spp., *Eremnus* spp., *Ereunetis* spp., *Eriophyes* spp., *Eriosoma* spp., *Eriosoma lanigerum*, *Erythroneura* spp., *Estigmene* spp., *Ethmia* spp., *Etiella* spp., *Euagrotis* spp., *Eucosrna* spp., *Euehlaena* spp., *Euelidia* spp., *Eueosma* spp., *Euchistus* spp., *Eucosmomorpha* spp., *Eudonia* spp., *Eufidonia* spp., *Euhyponeutoides* spp., *Eulepitodes* spp., *Eulia* spp., *Eulithis* spp., *Eupithecia* spp., *Euplexia* spp., *Eupoecilia* spp., *Eupoecilia ambiguella*, *Euproctis* spp., *Eupsilia* spp., *Eurhodope* spp., *Eurois* spp.,

*Eurygaster* spp., *Eurythmia* spp., *Eustrotia* spp., *Euxoa* spp., *Euzophera* spp., *Evergestis* spp., *Evippe* spp., *Exartema* spp., *Fannia* spp., *Faronta* spp., *Feltia* spp., *Filatima* spp., *Fishia* spp., *Frankliniella* spp., *Fumibotys* spp., *Gaesa* spp., *Gasgardia* spp., *Gastrophilus* spp., *Gelechia* spp., *Gilpinia* spp., *Gilpinia polytoma*, *Glossina* spp., *Glyphipterix* spp., *Glyphodes* spp., *Gnorimoschemini* spp., *Gonodonta* spp., *Gortyna* spp., *Gracillaria* spp., *Graphania* spp., *Grapholita* spp., *Grapholitha* spp., *Gravitarmata* spp., *Gretchena* spp., *Griselda* spp., *Gryllotalpa* spp., *Gynaephora* spp., *Gypsonoma* spp., *Hada* spp., Haematopinus spp., *Halisidota* spp., *Harpipteryx* spp., *Harrisina* spp., *Hedya* spp., *Helicoverpa* spp., *Heliophobus* spp., *Heliothis* spp., *Hellula* spp., *Helotropa* spp., *Hemaris* spp., *Hercinothrips* spp., *Herculia* spp., *Hermonassa* spp., *Heterogenea* spp., *Holomelina* spp., *Homadaula* spp., *Homoeosoma* spp., *Homoglaea* spp., *Homohadena* spp., *Homona* spp., *Homonopsis* spp., *Hoplocampa* spp., *Hoplodrina* spp., *Hoshinoa* spp., *Hxalomma* spp., *Hydraecia* spp., *Hydriomena* spp., *Hyles* spp., *Hyloicus* spp., *Hypagyrtis* spp., *Hypatima* spp., *Hyphantria* spp., *Hyphantria cunea*, *Hypocala* spp., *Hypocoena* spp., *Hypodema* spp., *Hyppobosca* spp., *Hypsipyla* spp., *Hyssia* spp., *Hysterosia* spp., *Idaea* spp., Idia app., *Ipimorpha* spp., *Isia* spp., *Isochorista* spp., *Isophrictis* spp., *Isopolia* spp., *Isotrias* spp., *Ixodes* spp., *Itame* spp., *Jodia* spp., *Jodis* spp., *Kawabea* spp., *Keiferia* spp., *Keiferia lycopersicella*, *Labdia* spp., *Lacinipolia* spp., *Lambdina* spp., *Lamprothritpa* spp., *Laodelphax* spp., *Lasius* spp., *Laspeyresia* spp., *Leptinotarsa* spp., *Leptinotarsa decemlineata*, *Leptocorisa* spp., *Leptostales* spp., *Lecanium* spp., *Lecanium corni*, *Lepidosaphes* spp., *Lepisma* spp., *Lepisma saccharina*, *Lesmone* spp., *Leucania* spp., *Leucinodes* spp., *Leucophaea* spp., *Leucophaea maderae*, *Leucoptera* spp., *Leucoptera scitella*, *Linognathus* spp., *Liposcelis* spp., *Lissorhoptrus* spp., *Lithacodia* spp., *Lithocolletis* spp., *Lithomoia* spp., *Lithophane* spp., *Lixodessa* spp., *Lobesia* spp., *Lobesia botrana*, *Lobophora* spp., *Locusta* spp., *Lomanaltes* spp., *Lomographa* spp., *Loxagrotis* spp., *Loxostege* spp., *Lucilia* spp., *Lymantria* spp., *Lymnaecia* spp., *Lyonetia* spp., *Lyriomyza* spp., *Macdonnoughia* spp., *Macrauzata* spp., *Macronoctua* spp., *Macrosiphus* spp., *Malacosoma* spp., *Maliarpha* spp., *Mamestra* spp., *Mamestra brassicae*, *Manduca* spp., *Manduca sexta*, *Marasmia* spp., *Margaritia* spp., *Matratinea* spp., *Matsumuraeses* spp., *Melanagromyza* spp., *Melipotes* spp., *Melissopus* spp., *Melittia* spp., *Melolontha* spp., *Meristis* spp., *Meritastis* spp., *Merophyas* spp., *Mesapamea* spp., *Mesogona* spp., *Mesoleuca* spp., *Metanema* spp., *Metendothenia* spp., *Metzneria* spp., *Micardia* spp., *Microcorses* spp., *Microleon* spp., *Mnesictena* spp., *Mocis* spp., *Monima* spp., *Monochroa* spp., *Monomorium* spp., *Monomorium pharaonis*, *Monopsis* spp., *Morrisonia* spp., *Musca* spp., *Mutuuraia* spp., *Myelois* spp., *Mythimna* spp., *Myzus* spp., *Naranga* spp., *Nedra* spp., *Nemapogon* spp., *Neodiprion* spp., *Neosphaleroptera* spp., *Nephelodes* spp., *Nephotettix* spp., *Nezara* spp., *Nilaparvata* spp., *Niphonympha* spp., *Nippoptilia* spp., *Noctua* spp., *Nola* spp., *Notocelia* spp., *Notodonta* spp., *Nudaurelia* spp., *Ochropleura* spp., *Ocnerostoma* spp., *Oestrus* spp., *Olethreutes* spp., *Oligia* spp., *Olindia* spp., *Olygonychus* spp., *Olygonychus gallinae*, *Oncocnemis* spp., *Operophtera* spp., *Ophisma* spp., *Opogona* spp., *Oraesia* spp., *Orniodoros* spp., *Orgyia* spp., *Oria* spp., *Orseolia* spp., *Orthodes* spp., *Orthogonia* spp., *Orthosia* spp., *Oryzaephilus* spp., *Oscinella* spp., *Oscinella frit*, *Osminia* spp., *Ostrinia* spp., *Ostrinia nubilalis*, *Otiorhynchus* spp., *Ourapteryx* spp., *Pachetra* spp., *Pachysphinx* spp., *Pagyda* spp., *Paleacrita* spp., *Paliga* spp., *Paithis* spp., *Pammene* spp., *Pandemis* spp., *Panemeria* spp., *Panolis* spp., *Panolis flammea*, *Panonychus* spp., *Parargyresthia* spp., *Paradiarsia* spp., *Paralobesia* spp., *Paranthrene* spp., *Parapandemis* spp., *Parapediasia* spp., *Parastichtis* spp., *Parasyndemis* spp., *Paratoria* spp., *Pareromeme* spp., *Pectinophora* spp., *Pectinophora gossypiella*, *Pediculus* spp., *Pegomyia* spp., *Pegomyia hyoscyami*, *Pelochrista* spp., *Pennisetia* spp., *Penstemonia* spp., *Pemphigus* spp., *Peribatodes* spp., *Peridroma* spp., *Perileucoptera* spp., *Periplaneta* spp., *Perizoma* spp., *Petrova* spp., *Pexicopia* spp., *Phalonia* spp., *Phalonidia* spp., *Phaneta* spp., *Phlyctaenia* spp., *Phlyctinus* spp., *Phorbia* spp., *Phragmatobia* spp., *Phricanthes* spp., *Phthorimaea* spp., *Phthorimaea operculella*, *Phyllocnistis* spp., *Phyllocoptruta* spp., *Phyllocoptruta oleivora*, *Phyllonorycter* spp., *Phyllophila* spp., *Phylloxera* spp., *Pieris* spp., *Pieris rapae*, *Piesma* spp., *Planococus* spp., *Planotortrix* spp., *Platyedra* spp., *Platynota* spp., *Platyptilia* spp., *Platysenta* spp., *Plodia* spp., *Plusia* spp., *Plutella* spp., *Plutella xylostella*, *Podosesia* spp., *Polia* spp., *Popillia* spp., *Polymixis* spp., *Polyphagotarsonemus* spp., *Polyphagotarsonemus latus*, *Prays* spp., *Prionoxystus* spp., *Probole* spp., *Proceras* spp., *Prochoerodes* spp., *Proeulia* spp., *Proschistis* spp., *Proselena* spp., *Proserpinus* spp., *Protagrotis* spp., *Proteoteras* spp., *Protobathra* spp., *Protoschinia* spp., *Pselnophorus* spp., *Pseudaletia* spp., *Pseudanthonomus* spp., *Pseudaternelia* spp., *Pseudaulacaspis* spp., *Pseudexentera* spp., *Pseudococus* spp., *Pseudohermenias* spp., *Pseudoplusia* spp., *Psoroptes* spp., *Psylla* spp., *Psylliodes* spp., *Pterophorus* spp., *Ptycholoma* spp., *Pulvinaria* spp., *Pulvinaria aethiopica*, *Pyralis* spp., *Pyrausta* spp., *Pyrgotis* spp., *Pyrreferra* spp., *Pyrrharctia* spp., *Quadraspidiotus* spp., *Rancora* spp., *Raphia* spp., *Reticultermes* spp., *Retinia* spp., *Rhagoletis* spp, *Rhagoletis pomonella*, *Rhipicephalus* spp., *Rhizoglyphus* spp., *Rhizopertha* spp., *Rhodnius* spp., *Rhophalosiphum* spp., *Rhopobota* spp., *Rhyacia* spp., *Rhyacionia* spp., *Rhynchopacha* spp., *Rhyzosthenes* spp., *Rivula* spp., *Rondotia* spp., *Rusidrina* spp., *Rynchaglaea* spp., *Sabulodes* spp., *Sahlbergella* spp., *Sahlbergella singularis*, *Saissetia* spp., *Samia* spp., *Sannina* spp., *Sanninoidea* spp., *Saphoideus* spp., *Sarcoptes* spp., *Sathrobrota* spp., Scarabeidae, *Sceliodes* spp., *Schinia* spp., *Schistocerca* spp., *Schizaphis* spp., *Schizura* spp., *Schreckensteinia* spp., *Sciara* spp., *Scirpophaga* spp., *Scirthrips auranti*, *Scoparia* spp., *Scopula* spp., *Scotia* spp., *Scotinophara* spp., *Scotogramma* spp., *Scrobipalpa* spp., *Scrobipalpopsis* spp., *Semiothisa* spp., *Sereda* spp., *Sesamia* spp., *Sesia* spp., *Sicya* spp., *Sideridis* spp., *Simyra* spp., *Sineugraphe* spp., *Sitochroa* spp., *Sitobion* spp., *Sitophilus* spp., *Sitotroga* spp., *Solenopsis* spp., *Smerinthus* spp., *Sophronia* spp., *Spaelotis* spp., *Spargaloma* spp., *Sparganothis* spp., *Spatalistis* spp., *Sperchia* spp., *Sphecia* spp., *Sphinx* spp., *Spilonota* spp., *Spodoptera* spp., *Spodoptera littoralis*, *Stagmatophora* spp., *Staphylinochrous* spp., *Stathmopoda* spp., *Stenodes* spp., *Sterrha* spp., *Stomoxys* spp., *Strophedra* spp., *Sunira* spp., *Sutyna* spp., *Swammerdamia* spp., *Syllomatia* spp., *Sympistis* spp., *Synanthedon* spp., *Synaxis* spp., *Syncopacma* spp., *Syndemis* spp., *Syngrapha* spp., *Synthomeida* spp., *Tabanus* spp., *Taeniarchis* spp., *Taeniothrips* spp., *Tannia* spp., *Tarsonemus* spp., *Tegulifera* spp., *Tehama* spp., *Teleiodes* spp., *Telorta* spp., *Tenebrio* spp., *Tephrina* spp., *Terataglaea* spp., *Terricula* spp., *Tethea* spp., *Tetranychus* spp., *Thalpophila* spp., *Thaumetopoea* spp., *Thiodia* spp., *Thrips* spp., *Thrips palmi*, *Thrips tabaci*, *Thyridopteryx* spp., *Thyris* spp., *Tineola* spp., *Tipula* spp., *Tortricidia* spp., *Tortrix* spp., *Trachea* spp., *Trialeurodes* spp., *Trialeurodes vaporariorum*, *Triatoma* spp., *Triaxomera* spp., *Tribolium* spp., *Tricodectes* spp., *Trichoplusia* spp., *Trichoplusia ni*, *Trichoptilus* spp., *Trioza* spp., *Trioza erytreae*, *Triphaenia* spp., *Triphosa* spp., *Trogoderma* spp., *Tyria* spp., *Udea* spp., *Unaspis* spp., *Unaspis citri*, *Utetheisa* spp., *Valeriodes* spp.,

*Vespa* spp., *Vespamima* spp., *Vitacea* spp., *Vitula* spp., *Witlesia* spp., *Xanthia* spp., *Xanthorhoe* spp., *Xanthotype* spp., *Xenomicta* spp., *Xenopsylla* spp., *Xenopsylla* cheopsis, *Xestia* spp., *Xylena* spp., *Xylomyges* spp., *Xyrosaris* spp., *Yponomeuta* spp., *Ypsolopha* spp., *Zale* spp., *Zanclognathus* spp., *Zeiraphera* spp., *Zenodoxus* spp., *Zeuzera* spp., *Zygaena* spp., It is also possible to control pests of the class Nematoda using the compounds according to the invention. Such pests include, for example, root knot nematodes, cyst-forming nematodes and also stem and leaf nematodes;

especially of *Heterodera* spp., e.g. *Heterodera schachtii*, *Heterodora avenae* and *Heterodora trifolii*; *Globodera* spp., e.g. *Globodera rostochiensis*; *Meloidogyne* spp., e.g. *Meloidogyne incognita* and *Meloidogyne javanica*; *Radopholus* spp., e.g. *Radopholus similis*; *Pratylenchus*, e.g. *Pratylenchus neglectans* and *Pratylenchus penetrans*; *Tylenchulus*, e.g. *Tylenchulus semipenetrans*; *Longidorus*, *Trichodorus*, *Xiphinema*, *Ditylenchus*, *Apheenchoides* and *Anguina*; especially *Meloidogyne*, e.g. *Meloidogyne incognita*, and *Heterodera*, e.g. *Heterodera glycines*.

An especially important aspect of the present invention is the use of the compounds of formula (I) according to the invention in the protection of plants against parasitic feeding pests.

The action of the compounds according to the invention and the compositions comprising them against animal pests can be significantly broadened and adapted to the given circumstances by the addition of other insecticides, acaricides or nematicides. Suitable additives include, for example, representatives of the following classes of active ingredient: organophosphorus compounds, nitrophenols and derivatives, formamidines, ureas, carbamates, pyrethroids, chlorinated hydrocarbons, neonicotinoids and *Bacillus thuringiensis* preparations.

Examples of especially suitable mixing partners include: azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; iodfenphos; kinoprene; lufenuron; methacriphos; methidathion; monocrotophos; phosphamidon; profenofos; diofenolan; a compound obtainable from the *Bacillus thuringiensis* strain GC91 or from strain NCTC11821; pymetrozine; bromopropylate; methoprene; disulfoton; quinalphos; taufluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; thiamethoxam; clothianidine; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; fenazaquin; pyriproxyfen; pyrimidifen; nitenpyram; acetamiprid; abamectin; emamectin; emamectin-benzoate; spinosad; a plant extract that is active against insects; a preparation that comprises nematodes and is active against insects; a preparation obtainable from *Bacillus subtilis*; a preparation that comprises fungi and is active against insects; a preparation that comprises viruses and is active against insects; chlorfenapyr; acephate; acrinathrin; alanycarb; alphamethrin; amitraz; AZ 60541; azinphos A; azinphos M; azocyclotin; bendiocarb; bensultap; beta-cyfluthrin; BPMC; brofenprox; bromophos A; bufencarb; butocarboxin; butylpyridaben; cadusafos; carbaryl; carbophenothion; chloethocarb; chlorethoxyfos; chlormephos; cis-resmethrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; IKI-220; iprobenfos; isofenphos; isoxathion; ivermectin; malathion; mecarbam; mesulfenphos; metaldehyde; metolcarb; milbemectin; moxidectin; naled; NC 184; omethoate; oxamyl; oxydemethon M; oxydeprofos; permethrin; phenthoate; phorate; phosmet; phoxim; pirimiphos M; pirimiphos E; promecarb; propaphos; prothiofos; prothoate; pyrachlophos; pyradaphenthion; pyresmethrin; pyrethrum; tebufenozide; salithion; sebufos; sulfotep; sulprofos; tebufenpyrad; tebupirimphos; tefluthrin; temephos; terbam; tetrachlorvinphos; thiacloprid; thiafenox; thiodicarb; thiofanox; thionazin; thuringiensin; tralomethrin; triarthene; triazophos; triazuron; trichlorfon; triflumuron; trimethacarb; vamidothion; xylylcarb; YI 5301/5302; zetamethrin; DPX-MP062—indoxacarb; methoxyfenozide; bifenazate; XMC (3,5-xylyl methylcarbamate); or the fungus pathogen *Metarhizium anisopliae*.

The compounds according to the invention can be used to control, i.e. to inhibit or destroy, pests of the mentioned type occurring on plants, especially on useful plants and ornamentals in agriculture, in horticulture and in forestry, or on parts of such plants, such as the fruits, blossoms, leaves, stems, tubers or roots, while in some cases plant parts that grow later are still protected against those pests.

Target crops include especially cereals, such as wheat, barley, rye, oats, rice, maize and sorghum; beet, such as sugar beet and fodder beet; fruit, e.g. pomes, stone fruit and soft fruit, such as apples, pears, plums, peaches, almonds, cherries and berries, e.g. strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

Further areas of use of the compounds according to the invention are the protection of stored goods and storerooms and the protection of raw materials, and also in the hygiene sector, especially the protection of domestic animals and productive livestock against pests of the mentioned type, more especially the protection of domestic animals, especially cats and dogs, from infestation by fleas, ticks and nematodes.

The invention therefore relates also to pesticidal compositions, such as emulsifiable concentrates, suspension concentrates, directly sprayable or dilutable solutions, spreadable pastes, dilute emulsions, wettable powders, soluble powders, dispersible powders, wettable powders, dusts, granules and encapsulations of polymer substances, that comprise at least one of the compounds according to the invention, the choice of formulation being made in accordance with the intended objectives and the prevailing circumstances.

The active ingredient is used in those compositions in pure form, a solid active ingredient, for example, in a specific particle size, or preferably together with at least one of the adjuvants customary in formulation technology, such as extenders, e.g. solvents or solid carriers, or surface-active compounds (surfactants). In the area of parasite control in humans, domestic animals, productive livestock and pets it will be self-evident that only physiologically tolerable additives are used.

Solvents are, for example: non-hydrogenated or partly hydrogenated aromatic hydrocarbons, preferably fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and ethers and esters thereof, such as propylene glycol, dipropylene glycol ether, ethylene glycol or ethylene glycol monomethyl or -ethyl ether, ketones, such as cyclohexanone, isophorone or diacetone alcohol, strongly polar solvents, such as N-methylpyrrolid-2-one, dimethyl sulfoxide or N,N-dimethylformamide, water, non-epoxidized or epoxidized plant oils, such as non-epoxidized or epoxidized rapeseed, castor, coconut or soya oil, and silicone oils.

The solid carriers used, for example for dusts and dispersible powders, are as a rule natural rock powders, such as calcite, talc, kaolin, montmorillonite or attapulgite. Highly disperse silicic acids or highly disperse absorbent polymers can also be added to improve the physical properties. Granular adsorptive granule carriers are porous types, such as pumice, crushed brick, sepiolite or bentonite, and non-sorbent carrier materials are calcite or sand. A large number of granular materials of inorganic or organic nature can furthermore be used, in particular dolomite or comminuted plant residues.

Surface-active compounds are, depending on the nature of the active compound to be formulated, nonionic, cationic and/or anionic surfactants or surfactant mixtures with good emulsifying, dispersing and wetting properties. The surfactants listed below are to be regarded only as examples; many other surfactants which are customary in formulation technology and are suitable according to the invention are described in the relevant literature.

Nonionic surfactants are, in particular, polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols. Substances which are furthermore suitable are water-soluble polyethylene oxide adducts, containing 20 to 250 ethylene glycol ether and 10 to 100 propylene glycol ether groups, on propylene glycol, ethylene diaminopolypropylene glycol and alkyl polypropylene glycol having 1 to 10 carbon atoms in the alkyl chain. The compounds mentioned usually contain 1 to 5 ethylene glycol units per propylene glycol unit. Examples are nonylphenol-polyethoxyethanols, castor oil polyglycol ethers, polypropylene-polyethylene oxide adducts, tributylphenoxypolyethoxyethanol, polyethylene glycol and octylphenoxypolyethoxyethanol. Other substances are fatty acid esters of polyoxyethylene sorbitan, such as polyoxyethylene sorbitan trioleate.

The cationic surfactants are, in particular, quaternary ammonium salts which contain, as substituents, at least one alkyl radical having 8 to 22 C atoms and, as further substituents, lower, non-halogenated or halogenated alkyl, benzyl or lower hydroxyalkyl radicals. The salts are preferably in the form of halides, methyl-sulfates or ethyl-sulfates. Examples are stearyl-trimethyl-ammonium chloride and benzyl-di-(2-chloroethyl)-ethyl-ammonium bromide.

Suitable anionic surfactants can be both water-soluble soaps and water-soluble synthetic surface-active compounds. Suitable soaps are the alkali metal, alkaline earth metal and substituted or unsubstituted ammonium salts of higher fatty acids ($C_{10}$-$C_{22}$), such as the sodium or potassium salts of oleic or stearic acid, or of naturally occurring fatty acid mixtures, which can be obtained, for example, from coconut oil or tall oil; and furthermore also the fatty acid methyl-taurine salts. However, synthetic surfactants are more frequently used, in particular fatty sulfonates, fatty sulfates, sulfonated benzimidazole derivatives or alkylarylsulfonates. The fatty sulfonates and sulfates are as a rule in the form of alkali metal, alkaline earth metal or substituted or unsubstituted ammonium salts and in general have an alkyl radical of 8 to 22 C atoms, alkyl also including the alkyl moiety of acyl radicals; examples are the sodium or calcium salt of ligninsulfonic acid, of dodecylsulfuric acid ester or of a fatty alcohol sulfate mixture prepared from naturally occurring fatty acids. These also include the salts of sulfuric acid esters and sulfonic acids of fatty alcohol-ethylene oxide adducts. The sulfonated benzimidazole derivatives preferably contain 2 sulfonic acid groups and a fatty acid radical having about 8 to 22 C atoms. Alkylarylsulfonates are, for example, the sodium, calcium or triethanolammonium salts of dodecylbenzenesulfonic acid, of dibutylnaphthalenesulfonic acid or of a naphthalenesulfonic acid-formaldehyde condensation product. Corresponding phosphates, such as salts of the phosphoric acid ester of a p-nonylphenol-(4-14)-ethylene oxide adduct or phospholipids, can further also be used.

The compositions as a rule comprise 0.1 to 99%, in particular 0.1 to 95%, of active compound and 1 to 99.9%, in particular 5 to 99.9%, of—at least—one solid or liquid auxiliary, it being possible as a rule for 0 to 25%, in particular 0.1 to 20%, of the composition to be surfactants (% is in each case percent by weight). While concentrated compositions are more preferred as commercial goods, the end user as a rule uses dilute compositions which comprise considerably lower concentrations of active compound. Preferred compositions are composed, in particular, as follows (%=percent by weight):

Emulsifiable Concentrates:

| active ingredient: | 1 to 90%, preferably 5 to 20% |
| surfactant: | 1 to 30%, preferably 10 to 20% |
| solvent: | balance |

Dusts:

| active ingredient: | 0.1 to 10%, preferably 0.1 to 1% |
| solid carrier: | 99.9 to 90%, preferably 99.9 to 99% |

Suspension Concentrates:

| active ingredient: | 5 to 75%, preferably 10 to 50% |
| surfactant: | 1 to 40%, preferably 2 to 30% |
| water: | balance |

Wettable Powders:

| active ingredient: | 0.5 to 90%, preferably 1 to 80% |
|---|---|
| surfactant: | 0.5 to 20%, preferably 1 to 15% |
| solid carrier: | balance |

Granules:

| active ingredient: | 0.5 to 30%, preferably 3 to 15% |
|---|---|
| solid carrier: | 99.5 to 70%, preferably 97 to 85% |

The compositions according to the invention may also comprise further solid or liquid adjuvants, such as stabilisers, e.g. vegetable oils or epoxidised vegetable oils (e.g. epoxidised coconut oil, rapeseed oil or soybean oil), antifoams, e.g. silicone oil, preservatives, viscosity regulators, binders and/or tackifiers as well as fertilisers or other active ingredients for obtaining special effects, e.g. acaricides, bactericides, fungicides, nematicides, molluscicides or selective herbicides.

The crop protection products according to the invention are prepared in known manner, in the absence of adjuvants, e.g. by grinding, sieving and/or compressing a solid active ingredient or mixture of active ingredients, for example to a certain particle size, and in the presence of at least one adjuvant, for example by intimately mixing and/or grinding the active ingredient or mixture of active ingredients with the adjuvant(s). The invention relates likewise to those processes for the preparation of the compositions according to the invention and to the use of the compounds of formula (I) in the preparation of those compositions.

The invention relates also to the methods of application of the crop protection products, i.e. the methods of controlling pests of the mentioned type, such as spraying, atomising, dusting, coating, dressing, scattering or pouring, which are selected in accordance with the intended objectives and the prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha, most preferably from 20 to 100 g/ha.

A preferred method of application in the area of crop protection is application to the foliage of the plants (foliar application), the frequency and the rate of application being dependent upon the risk of infestation by the pest in question. However, the active ingredient can also penetrate the plants through the roots (systemic action) when the locus of the plants is impregnated with a liquid formulation or when the active ingredient is incorporated in solid form into the locus of the plants, for example into the soil, e.g. in granular form (soil application). In the case of paddy rice crops, such granules may be applied in metered amounts to the flooded rice field.

The crop protection products according to the invention are also suitable for protecting plant propagation material, e.g. seed, such as fruits, tubers or grains, or plant cuttings, against animal pests. The propagation material can be treated with the composition before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example to the seed furrow during sowing. The invention relates also to such methods of treating plant propagation material and to the plant propagation material so treated.

PREPARATION EXAMPLES

Since in most cases the compounds are present as mixtures of the avermectin derivatives B1a and B1b, characterization by customary physical data such as melting point or refractive index makes little sense. For this reason, the compounds are characterized by the retention times which are determined in an analysis by HPLC (high performance liquid chromatography). Here, the term B1a refers to the main component in which $R_1$ is sec-butyl, with a content of usually more than 80%. B1b denotes the minor component in which $R_1$ is isopropyl. The compounds where two retention times are given both for the B1a and for the B1b derivative are mixtures of diastereomers which can be separated chromatographically. In the case of compounds where a retention time is given only in column B1a or only in column B1b, the pure B1a or B1b component, respectively, can be obtained during work-up. The correct structures of the B1a and B1b components are assigned by mass spectrometry. The following method is used for HPLC analysis:

| HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [µl/min] |
| 0 | 80 | 20 | 500 |
| 0.1 | 50 | 50 | 500 |
| 10 | 5 | 95 | 500 |
| 15 | 0 | 100 | 500 |
| 17 | 0 | 100 | 500 |
| 17.1 | 80 | 20 | 500 |
| 22 | 80 | 20 | 500 |
| Type of column | YMC-Pack ODS-AQ | | |
| Column length | 125 mm | | |
| Internal diameter of column: | 2 mm | | |
| Temperature | 40° C. | | |

The YMC-Pack ODS-AQ column used for the chromatography of the compounds is manufactured by YMC, Alte Raesfelderstrasse 6, 46514 Schermbeck, Germany.

Example P.1

4'-(S)—O-[(Methylamino)carbonyl]avermectin B1 monosaccharide

Step A: To a solution of 5-O-tert-butyldimethylsilyl avermectin B1 monosaccharide (18 g) in dichloromethane (210 ml) is added 4-dimethylaminopyridine (5.2 g) and 1,1'-carbonyldiimdazole (11.4 g). The mixture is stirred at room temperature for 1.5 hours after which time the mixture is poured into ice-water (350 ml). Extraction with dichloromethane is followed by drying of the organic extracts over magnesium sulphate, filtration and removal of the solvent by distillation under reduced pressure. The crude material obtained is purified by flash column chromatography on silica gel (hexane/ethyl acetate) yielding 5-O-tert-butyldimethylsilyl-4'-O-[(imidazol-1-yl)carbonyl]avermectin B1 monosaccharide, which is characterized by its mass and nmr spectra.

Step B: To a solution of 5-O-tert-butyldimethylsilyl-4'-(S)—O-[(imidazol-1-yl)-carbonyl]avermectin B1 monosaccharide (13.6 g) in methanol (145 ml) cooled in an ice bath is added a solution of methanesulphonic acid (1.0 ml) in methanol (2.5 ml). The mixture is stirred for 3 hours after which time the mixture is poured into saturated sodium hydrogen carbonate (200 ml). Extraction with ethyl acetate is followed by drying of the organic extracts over magnesium sulphate, filtration and removal of the solvent by distillation under reduced pressure. The crude material obtained is purified by flash column chromatography on silica gel (hexane/ethyl acetate) yielding 4'-O-[(imidazol-1-yl)-carbonyl]-avermectin B1 monosaccharide, which is characterized by its mass and nmr spectra.

4'-(S)—O-[(Imidazol-1-yl)-carbonyl]-avermectin B1 monosaccharide: $B_{1a} C_{45}H_{62}N_2O_{12}$, MW: 822 MS: 823 (M+H). 1H NMR (300 MHz, $CDCl_3$) selected data, $\delta H$ (ppm): 8.23 (s, 1H, imidazole), 7.61 (s, 1H, imidazole), 7.13 (s, 1H, imidazole), 3.42 (s, 3H, $OCH_3$).

Step C: To a solution of 4'-(S)—O-[(imidazol-1-yl)-carbonyl]-avermectin B1 monosaccharide (2.9 g) in acetonitrile (20 ml) at room temperature is added methyl iodide (5.4 ml). The mixture is stirred for 3 hours after which time the volatile components are removed by distillation under reduced pressure affording 4'-O-[(3-carbonyl-1-methyl-3H-imidazol-1-ium)iodide]avermectin B1 monosaccharide.

Step D: To a solution of 4'-(S)—O-[(3-carbonyl-1-methyl-3H-imidazol-1-ium)iodide]avermectin B1 monosaccharide (232 mg) in dichloromethane (5 ml) is added methylamine hydrochloride (81 mg) and triethylamine (88 μl). After stirring at room temperature for 0.5 hours, water is added and the mixture is extracted with dichloromethane. Drying of the organic extracts over magnesium sulphate is followed by filtration and removal of the solvent by distillation under reduced pressure. The crude material obtained is purified by flash column chromatography on silica gel (hexane/ethyl acetate) yielding 4'-O-[(methylamino)carbonyl]avermectin B1 monosaccharide which is characterized by its mass and nmr spectra.

4'-(S)—O-[(Methylamino)carbonyl]avermectin monosaccharide: $B_{1a} C_{43}H_{63}NO_{12}$, MW: 785.4 LCMS: $t_{RT}$: 7.15, 808.4 (M+Na); 1H NMR (300 MHz, $CDCl_3$) selected data, $\delta H$ (ppm): 3.28 (m, 1H, CH-2), 3.44 (s, 3H, $OCH_3$), 2.84 (d, J=6 Hz, 3H, $NCH_3$); $B_{1b} C_{42}H_{61}NO_{12}$, MW: 771.4 LCMS: $t_{RT}$: 6.51, 808.4 (M+Na).

Example P.2

4'-(S)—O-[(Cyclohexylamino)carbonyl]avermectin B1 monosaccharide

To a solution of 4'-(S)—O-[(3-carbonyl-1-methyl-3H-imidazol-1-ium)iodide]avermectin B1 monosaccharide (Example P1, step C, 192 mg) in dichloromethane (5 ml) is added cyclohexylamine (114 μl). After stirring at room temperature for 1.5 hours, water is added and the mixture is extracted with dichloromethane. Drying of the organic extracts over magnesium sulphate is followed by filtration and removal of the solvent by distillation under reduced pressure. The crude material obtained is purified by flash column chromatography on silica gel (hexane/ethyl acetate) yielding 4'-O-[(cyclohexylamino)-carbonyl]avermectin B1 monosaccharide, which is characterized by its mass and nmr spectra.

4'-(S)—O-[(Cyclohexylamino)carbonyl]avermectin monosaccharide: $B_{1a} C_{48}H_{71}NO_{12}$, MW: 853.5 LCMS: $t_{RT}$: 9.49, 876.4 (M+Na); $B_{1b} C_{47}H_{69}NO_{12}$, MW: 771.4 LCMS: $t_{RT}$: 8.85, 876.4 (M+Na).

Example P.3

4'-(S)—O-[(Benzylamino)carbonyl]avermectin B1 monosaccharide

To a solution of 4'-(S)—O-[(3-carbonyl-1-methyl-3H-imidazol-1-ium)iodide]avermectin B1 monosaccharide (Example P1, step C, 192 mg) in dichloromethane (5 ml) is added benzylamine (109 μl). After stirring at room temperature for 1.5 hours, water is added and the mixture is extracted with dichloromethane. Drying of the organic extracts over magnesium sulphate is followed by filtration and removal of the solvent by distillation under reduced pressure. The crude material obtained is purified by flash column chromatography on silica gel (hexane/ethyl acetate) yielding 4'-O-[(benzylamino)-carbonyl]avermectin B1 monosaccharide, which is characterized by its mass and nmr spectra.

4'-(S)—O-[(Benzylamino)carbonyl]avermectin B1 monosaccharide: $B_{1a} C_{49}H_{67}NO_{12}$, MW: 861.5 LCMS: $t_{RT}$: 8.80, 884.5 (M+Na); $B_{1b} C_{48}H_{65}NO_{12}$, MW: 847.5 LCMS: $t_{RT}$: 8.16, 870.3 (M+Na).

Example P.4

4'-(R)—O-[(Allylamino)carbonyl]avermectin B1 monosaccharide

Step A: To a solution of 4-oxo-5-O-tert-butyldimethylsilyl avermectin B1 monosaccharide (2.0 g) in isopropanol (15 ml) at 0° C. is added sodium borohydride (30 mg). The mixture is stirred for 0.5 hours after which time the mixture is treated with brine (10 ml). Extraction with tert-butylmethyl ether is followed by drying of the organic extracts over magnesium sulphate, filtration and removal of the solvent by distillation under reduced pressure. The crude material obtained is purified by flash column chromatography on silica gel (hexane/ethyl acetate) yielding 4'-(R)-5-O-tert-butyldimethylsilyl avermectin B1 monosaccharide, which is characterized by its mass and nmr spectra.

Step B: To a solution of 4'-(R)-5-O-tert-butyldimethylsilyl avermectin B1 monosaccharide (1.6 g) in dichloromethane (18 ml) is added 4-dimethylaminopyridine (0.5 g) and 1,1'-carbonyldiimdazole (1.0 g). The mixture is stirred at room temperature for 1.5 hours after which time the mixture is poured into ice-water (100 ml). Extraction with dichloromethane is followed by drying of the organic extracts over magnesium sulphate, filtration and removal of the solvent by distillation under reduced pressure. The crude material obtained is purified by flash column chromatography on silica gel (hexane/ethyl acetate) yielding 5-O-tert-butyldimethylsilyl-4'-(R)—O-[(imidazol-1-yl)carbonyl]avermectin B1 monosaccharide, which is characterized by its mass and nmr spectra.

5-O-tert-Butyldimethylsilyl-4'-(R)—O-[(imidazol-1-yl)carbonyl]avermectin B1a monosaccharide: 1H NMR (300 MHz, $CDCl_3$) selected data, $\delta H$ (ppm): 8.18 (s, 1H, imidazole), 7.45 (s, 1H, imidazole), 7.08 (s, 1H, imidazole), 3.46 (s, 3H, $OCH_3$).

Step C: To a solution of 5-O-tert-butyldimethylsilyl-4'-(R)—O-[(imidazol-1-yl)carbonyl]-avermectin B1 monosaccharide (1.41 g) in acetonitrile (12 ml) at room temperature is added methyl iodide (2.3 ml). The mixture is stirred for 24 hours after which time the volatile components are removed by distillation under reduced pressure affording 5-O-tert-butyldimethylsilyl-4'-O—(R)-[(3-carbonyl-1-methyl-3H-imidazol-1-ium)iodide]avermectin B1 monosaccharide.

Step D: To a solution of 5-O-tert-butyldimethylsilyl-4'-O—(R)-[(3-carbonyl-1-methyl-3H-imidazol-1-ium)iodide] avermectin B1 monosaccharide (192 mg) in dichloromethane (5 ml) 75 µl allyl amine is added. After stirring at room temperature overnight, water is added and the mixture is extracted with dichloromethane. Drying of the organic extracts over magnesium sulphate is followed by filtration and removal of the solvent by distillation under reduced pressure. The crude material obtained is purified by flash column chromatography on silica gel (hexane/ethyl acetate) yielding 5-O-tert-butyldimethylsilyl 4'-O—(R)-[(alkylamino)carbonyl]avermectin B1 monosaccharide, which is characterized by its mass and nmr spectra.

Step E: To a solution of 5-O-tert-butyldimethylsilyl 4'-O—(R)-[(allylamino)carbonyl]avermectin B1 monosaccharide (123 mg) in THF (3 ml) is added pyridine (34 µl) and 70% HF-pyridine (138 µl) solution. The mixture is stirred for 18 h at room temperature, poured into aqueous NaHCO$_3$ (50%), extracted with ethyl acetate, dried over MgSO$_4$, and concentrated in vacuo. Flash chromatography (silica gel, hexane/ethyl acetate 1/1) affords 4'-O—(R)-[(allylamino)carbonyl] avermectin B1 monosaccharide, which is characterized by its mass and nmr spectra.

4'-O—(R)-[(Allylamino)carbonyl]avermectin monosaccharide: B$_{1a}$ C$_{45}$H$_{65}$NO$_{12}$, MW: 811.5 LCMS: t$_{RT}$: 7.68, 834.5 (M+Na); B$_{1b}$ C$_{44}$H$_{63}$NO$_{12}$, MW: 797.4 LCMS: t$_{RT}$: 7.20, 820.4 (M+Na).

Example P.5

4'-(R)—O-[(Cyclohexylamino)carbonyl]avermectin B1 monosaccharide

Step A: To a solution of 5-O-tert-butyldimethylsilyl-4'-O—(R)-[(3-carbonyl-1-methyl-3H-imidazol-1-ium)iodide] avermectin B1 monosaccharide (Example P4, step C, 192 mg) in dichloromethane (5 ml) is added cyclohexyl amine (114 µl). After stirring at room temperature for 12 hours, water is added and the mixture is extracted with dichloromethane. Drying of the organic extracts over magnesium sulphate is followed by filtration and removal of the solvent by distillation under reduced pressure. The crude material obtained is purified by flash column chromatography on silica gel (hexane/ethyl acetate) yielding 5-O-tert-butyldimethylsilyl 4'-O—(R)-[(cyclohexylamino)-carbonyl]avermectin B1 monosaccharide, which is characterized by its mass and nmr spectra.

Step B: To a solution of 5-O-tert-butyldimethylsilyl 4'-O—(R)-[(cyclohexylamino)carbonyl]avermectin B1 monosaccharide (100 mg) in THF (2.5 ml) is added pyridine (27 µl) and 70% HF-pyridine (107 µl) solution. The mixture is stirred for 14 h at room temperature, poured into aqueous NaHCO$_3$ (50%), extracted with ethyl acetate, dried over MgSO$_4$, and concentrated in vacuo. Flash chromatography (silica gel, hexane/ethyl acetate 1/1) affords 4'-O—(R)-[(cyclohexylamino)carbonyl]avermectin B1 monosaccharide, which is characterized by its mass and nmr spectra.

4'-O—(R)-[(Cyclohexylamino)carbonyl]avermectin monosaccharide: B$_{1a}$ C$_{48}$H$_{71}$NO$_{12}$, MW: 853.5 LCMS: t$_{RT}$: 9.60, 876.5 (M+Na); B$_{1b}$ C$_{47}$H$_{69}$NO$_{12}$, MW: 839.5 LCMS: t$_{Rf}$: 9.01, 862.5 (M+Na).

Example P.6

4'-(R)—O-[(Ethoxypropylamino)carbonyl]avermectin B1 monosaccharide

Step A: To a solution of 5-O-tert-butyldimethylsilyl-4'-O—(R)-[(3-carbonyl-1-methyl-3H-imidazol-1-ium)iodide] avermectin B1 monosaccharide (Example P4, step C, 192 mg) in dichloromethane (5 ml) is added 3-ethoxypropyl amine (120 µl). After stirring at room temperature overnight, water is added and the mixture is extracted with dichloromethane. Drying of the organic extracts over magnesium sulphate is followed by filtration and removal of the solvent by distillation under reduced pressure. The crude material obtained is purified by flash column chromatography on silica gel (hexane/ethyl acetate) yielding 5-O-tert-butyldimethylsilyl 4'-O—(R)-[(ethoxypropylamino)-carbonyl]avermectin B1 monosaccharide which is characterized by its mass and nmr spectra.

Step B: To a solution of 5-O-tert-butyldimethylsilyl 4'-O—(R)-[(ethoxypropylamino)carbonyl]avermectin B1 monosaccharide (38 mg) in THF (1.0 ml) is added pyridine (10 µl) and 70% HF-pyridine (41 µl) solution. The mixture is stirred for 16 h at room temperature, poured into aqueous NaHCO$_3$ (50%), extracted with ethyl acetate, dried over MgSO$_4$, and concentrated in vacuo. Flash chromatography (silica gel, hexane/ethyl acetate 1/1) affords 4'-O—(R)-[(ethoxypropylamino)carbonyl]avermectin B1 monosaccharide which is characterized by its mass and nmr spectra.

4'-O—(R)-[(Ethoxypropylamino)carbonyl]avermectin monosaccharide: B$_{1a}$ C$_{47}$H$_{71}$NO$_{13}$, MW: 857.5 LCMS: t$_{RT}$: 8.11, 880.5 (M+Na).

Example P.7

4'-(S)—O-[(Methylamino)thiocarbonyl]avermectin B1 monosaccharide

Step A: To a solution of 5-O-tert-butyldimethylsilyl avermectin B1 monosaccharide (843 mg) in N,N-dimethylformamide (5 ml) is added 1,1'-thiocarbonyldiimdazole (535 mg). The mixture is stirred at 60° C. for 4 hours after which time the mixture is diluted with ethyl acetate (100 ml) and poured into ice-water (100 ml). Extraction with ethyl acetate is followed by drying of the combined organic extracts over magnesium sulphate, filtration and removal of the solvent by distillation under reduced pressure. The crude material obtained is purified by flash column chromatography on silica gel (hexane/ethyl acetate) yielding 5-O-tert-butyldimethylsilyl-4'-O-[(imidazol-1-yl)thiocarbonyl]avermectin B1 monosaccharide, which is characterized by its mass and nmr spectra.

5-O-tert-butyldimethylsilyl 4'-(S)—O-[(Imidazol-1-yl)-thiocarbonyl]-avermectin B1 monosaccharide: B$_{1a}$ C$_{51}$H$_{76}$N$_2$O$_{11}$SSi, MW: 953 MS: 954 (M+H). 1H NMR (300 MHz, CDCl$_3$) selected data, δH (ppm): 8.37 (s, 1H, imidazole), 7.66 (s, 1H, imidazole), 7.06 (s, 1H, imidazole), 3.39 (s, 3H, OCH$_3$).

Step B: To a solution of 5-O-tert-butyldimethylsilyl 4'-(S)—O-[(imidazol-1-yl)thiocarbonyl]-avermectin B1 monosaccharide (381 mg) in methanol (5.0 ml) cooled in an ice bath is added a solution of methanesulphonic acid (29 µl). The mixture is stirred for 4 hours after which time the mixture is poured into saturated sodium hydrogen carbonate (10 ml). Extraction with ethyl acetate is followed by drying of the organic extracts over magnesium sulphate, filtration and removal of the solvent by distillation under reduced pressure.

The crude material obtained is purified by flash column chromatography on silica gel (hexane/ethyl acetate) yielding 4'-O-[(imidazol-1-yl)-thiocarbonyl]-avermectin B1 monosaccharide, which is characterized by its mass and nmr spectra.

4'-(S)—O-[(Imidazol-1-yl)-thiocarbonyl]-avermectin B1 monosaccharide: $B_{1a}$ $C_{45}H_{62}N_2O_{11}S$, MW: 838.4 MS: 861.4 (M+Na). 1H NMR (300 MHz, $CDCl_3$) selected data, $\delta H$ (ppm): 8.35 (s, 1H, imidazole), 7.64 (s, 1H, imidazole), 7.04 (s, 1H, imidazole), 3.38 (s, 3H, $OCH_3$).

Step C: To a solution of 4'-(S)—O-[(imidazol-1-yl)-thiocarbonyl]-avermectin B1 monosaccharide (15.4 g) in acetonitrile (100 ml) at room temperature is added methyl iodide (28.5 ml). The mixture is stirred for 16 hours after which time the volatile components are removed by distillation under reduced pressure affording 4'-O-[(3-thiocarbonyl-1-methyl-3H-imidazol-1-ium)iodide]avermectin B1 monosaccharide.

4'-(S)—O-[(3-Thiocarbonyl-1-methyl-3H-imidazol-1-ium)iodide]avermectin B1 monosaccharide: 1H NMR (300 MHz, $CDCl_3$) selected data, $\delta H$ (ppm): 10.84 (s, 1H, imidazolium), 8.05 (s, 1H, imidazolium), 7.76 (s, 1H, imidazolium), 3.43 (s, 3H, $OCH_3$).

Step D: To a solution of 4'-(S)—O-[(3-thiocarbonyl-1-methyl-3H-imidazol-1-ium)iodide]avermectin B1 monosaccharide (294 mg) in dichloromethane (5 ml) is added methylamine hydrochloride (101 mg) and triethylamine (209 µl). After stirring at room temperature for 16 hours, water is added and the mixture is extracted with dichloromethane. Drying of the organic extracts over magnesium sulphate is followed by filtration and removal of the solvent by distillation under reduced pressure. The crude material obtained is purified by flash column chromatography on silica gel (hexane/ethyl acetate) yielding 4'-(S)—O-[(methylamino)carbonyl]avermectin B1 monosaccharide which is characterized by its mass and nmr spectra.

4'-(S)—O-[(Methylamino)thiocarbonyl]avermectin monosaccharide: $B_{1a}$ $C_{43}H_{63}NO_{11}S$ MW: 801.4 LCMS: $t_{RT}$: 9.12, 824.4 (M+Na); $B_{1b}$ $C_{42}H_{61}NO_{11}S$, MW: 787.4 LCMS: $t_{RT}$: 8.43, 810.4 (M+Na).

Example P.8

4'-(S)—O-[(cyclopropylamino)thiocarbonyl]avermectin B1 monosaccharide

To a solution of 4'-(S)—O-[(3-thiocarbonyl-1-methyl-3H-imidazol-1-ium) iodide]avermectin B1 monosaccharide (Example P7, step C, 294 mg) in dichloromethane (5 ml) is added cyclopropylamine (105 µl). After stirring at room temperature for 16 hours, water is added and the mixture is extracted with dichloromethane. Drying of the organic extracts over magnesium sulphate is followed by filtration and removal of the solvent by distillation under reduced pressure. The crude material obtained is purified by flash column chromatography on silica gel (hexane/ethyl acetate) yielding 4'-O-[(cyclopropylamino)thiocarbonyl]avermectin B1 monosaccharide which is characterized by its mass and nmr spectra.

4'-(S)—O-[(Cyclopropylamino)thiocarbonyl]avermectin monosaccharide: $B_{1a}$ $C_{45}H_{65}NO_{11}S$, MW: 827.4 LCMS: $t_{RT}$: 9.87, 828.4 (M+H); $B_{1b}$ $C_{44}H_{63}NO_{11}S$, MW: 813.4 LCMS: $t_{RT}$: 9.23, 836.4 (M+Na).

Example P.9

4'-(S)—O-[(2-hydroxyethylamino)thiocarbonyl]avermectin B1 monosaccharide

To a solution of 4'-(S)—O-[(3-thiocarbonyl-1-methyl-3H-imidazol-1-ium)iodide]avermectin B1 monosaccharide (Example P.7, step C, 294 mg) in dichloromethane (5 ml) is added ethanolamine (90 µl). After stirring at room temperature for 16 hours, water is added and the mixture is extracted with dichloromethane. Drying of the organic extracts over magnesium sulphate is followed by filtration and removal of the solvent by distillation under reduced pressure. The crude material obtained is purified by flash column chromatography on silica gel (hexane/ethyl acetate) yielding 4'-O-[(2-hydroxyethylamino)thiocarbonyl]avermectin B1 monosaccharide which is characterized by its mass and nmr spectra.

4'-(S)—O-[(2-hydroxyethylamino)thiocarbonyl]avermectin monosaccharide: $B_{1a}$ $C_{44}H_{65}NO_{12}S$, MW: 831.4 LCMS: $t_{RT}$: 8.12, 854.4 (M+H); $B_{1b}$ $C_{43}H_{63}NO_{12}S$, MW: 817.4 LCMS: $t_{RT}$: 7.42, 840.4 (M+Na).

Example P.10

4"-(S)—O-[(pyrrolidino)carbonyl)]-avermectin B1

Step A: To a solution of 5-O-tert-butyldimethylsilyl avermectin B1 (2.0 g) in dichloromethane (20 ml) at 0° C. is added 4-dimethylaminopyridine (0.49 g) and 1,1'-carbonyldiimidazole (1.1 g). The mixture is stirred at room temperature for 2 hours after which time the solvent is removed under reduced pressure. The residue is purified by flash-chromatography (silica gel hexane/ethyl acetate) providing 5-O-tert-butyldimethylsilyl-4"-(S)—O-[(lmidazol-1-yl)-carbonyl]-avermectin B1 which is characterized by its mass and NMR spectra.

Step B: To a solution of 4"-(S)—O-[(Imidazol-1-yl)-carbonyl]-avermectin B1 (0.5 g) in dimethylformamide (20 ml) is added pyrrolidine (0.15 ml). After stirring at room temperature for 48 hours, water is added and the mixture is extracted with ethyl acetate. Drying of the organic extracts over sodium sulphate is followed by filtration and removal of the solvent by distillation under reduced pressure. The crude residue obtained is used as such for the next step.

Step C: To a solution of the crude residue obtained in step B in 15 ml tetrahydrofuran is added 2 ml of a HF-pyridine solution (consisting of 25 g 70% HF-Pyridin, 27.5 ml tetrahydrofuran and 12.5 ml pyridine), and the mixture is stirred at room temperature for 24 hours, poured into water, extracted with ethyl acetate; the organic phase is washed with saturated sodium bicarbonate, dried over sodium sulfate, and concentrated in vacuo. The residue is purified by flash-chromatography (silica gel hexane/ethyl acetate) providing 4"-O-[(pyrrolidino)carbonyl)]-avermectin B1 which is characterized by its mass and NMR spectra.

4"-(S)—O-[(pyrrolidino)carbonyl)]-avermectin B1: $B_{1a}$ $C_{53}H_{79}NO_{15}$ MW: 969.5 LCMS: $t_{RT}$: 11.01, 992.4 (M+Na).

Example P.11

4"-(S)—O-[(allylamino)carbonyl]avermectin B1

Step A: To a solution of 5-O-tert-butyldimethylsilyl avermectin B1 (1 g) in dichloromethane (5 ml) at 0° C. is added 4-dimethylaminopyridine (0.13 g) and 1,1'-carbonyldiimidazole (0.31 g). The mixture is stirred at room temperature for 2 hours after which time allylamine is added (0.20 ml). After stirring at room temperature for 18 hours, water is added (5 ml) and the mixture is extracted with dichloromethane. Drying of the organic extracts over sodium sulphate is followed by filtration and removal of the solvent by distillation under reduced pressure. The crude residue obtained is used as such in the next step.

Step B: To a solution of the crude residue obtained in step A in 10 ml tetrahydrofuran is added 5 ml of a HF-pyridine solution (consisting of 25 g 70% HF-Pyridin, 27.5 ml tetrahydrofuran and 12.5 ml pyridine), and the mixture is stirred at room temperature for 16 hours, poured into water, extracted with ethyl acetate; the organic phase is washed with saturated sodium bicarbonate, dried over sodium sulfate, and concentrated in vacuo. The residue is purified by flash-chromatography (silica gel hexane/ethyl acetate) providing 4"-(S)—O-[(allylamino)carbonyl]avermectin B1 which is characterized by its mass and NMR spectra.

4"-(S)—O-[(allylamino)carbonyl)]-avermectin B1: $B_{1a}$ $C_{52}H_{77}NO_{15}$ MW: 955.5 LCMS: $t_{RT}$: 9.85, 978.5 (M+Na).

Example P.12

4"-(S)—O-[(4-picolylamino)carbonyl]avermectin B1

Step A: To a solution of 5-O-tert-butyldimethylsilyl avermectin B1 (1 g) in dichloromethane (5 ml) at 0° C. is added 4-dimethylaminopyridine (0.13 g) and 1,1'-carbonyldiimidazole (0.31 g). The mixture is stirred at room temperature for 2 hours after which time 4-picolylamine is added (0.25 ml). After stirring at room temperature for 18 hours, water is added (5 ml) and the mixture is extracted with dichloromethane. Drying of the organic extracts over sodium sulphate is followed by filtration and removal of the solvent by distillation under reduced pressure. The crude residue obtained is used as such for the next step.

Step B: To a solution of the crude residue obtained in step A in 10 ml tetrahydrofuran is added 5 ml of a HF-pyridine solution (consisting of 25 g 70% HF-Pyridin, 27.5 ml tetrahydrofuran and 12.5 ml pyridine), and the mixture is stirred at room temperature for 16 hours, poured into water, extracted with ethyl acetate; the organic phase is washed with saturated sodium bicarbonate, dried over sodium sulfate, and concentrated in vacuo. The residue is purified by flash-chromatography (silica gel hexane/ethyl acetate) providing 4"-(S)—O-[(4-picolylamino)carbonyl]avermectin B1, which is characterized by its mass and NMR spectra.

4"-(S)—O-[(4-picolylamino)carbonyl)]avermectin B1: $B_{1a}$ $C_{55}H_{78}N_2O_{15}$ MW: 1006.5 LCMS: $t_{RT}$: 5.12, 1007.5 (M+H), 1029.5 (M+Na).

Example P.13

4"-(S)—O—[(O-methylhydroxylamino)carbonyl]avermectin B1

Step A: To a solution of 5-O-tert-butyldimethylsilyl-4"-(S)—O-[(Imidazol-1-yl)-carbonyl]-avermectin B1 (Example P.10, Step A, 280 mg) in dimethylformamide (5 ml) is added O-methylhydroxylamine hydrochloride (87 mg) and triethylamine (52 mg). After stirring at room temperature for 24 hours, water is added and the mixture is extracted with diethyl ether; the organic phase is washed with water and brine, dried over sodium sulfate, and concentrated in vacuo. The crude residue obtained is used as such in the next step.

Step B: To a solution of the crude residue obtained in step A in 10 ml methanol is added 0.13 ml of methanesulfonic acid, and the mixture is stirred at room temperature for 30 minutes, poured into saturated sodium bicarbonate, extracted with diethyl ether; the organic phase is washed with water and brine, dried over sodium sulfate, and concentrated in vacuo. The residue is purified by flash-chromatography (silica gel hexane/ethyl acetate) providing 4"-(S)—O—[(O-methylhydroxylamino)carbonyl]avermectin B1, which is characterized by its mass and NMR spectra.

4"-(S)—O—[(O-methylhydroxylamino)carbonyl]avermectin B1: $B_{1a}$ $C_{50}H_{75}NO_{16}$, MW: 946.15 MS: 963 (M+NH$_4^+$). 1H NMR (300 MHz, CDCl$_3$) selected data, δH (ppm): 7.41 (s, 1H, NH); 3.72 (s, 3H, NHOCH$_3$).

Example P.14

4'-(S)—O-[(hydrazino)carbonyl]avermectin B1

Step A: To a solution of 5-O-tert-butyldimethylsilyl-4"-(S)—O-[(Imidazol-1-yl)-carbonyl]-avermectin B1 (Example P.10, Step A, 500 mg) in dimethylformamide (5 ml) is added hydrazine hydrochloride (174 mg) and triethylamine (0.46 ml). After stirring at room temperature for 3 hours, water is added and the mixture is extracted with dichloromethane; the organic phase is washed with water and brine, dried over sodium sulfate, and concentrated in vacuo. The crude residue obtained is used as such in the next step.

Step B: To a solution of the crude residue obtained in step A in 15 ml methanol is added 0.2 ml of methanesulfonic acid, and the mixture is stirred at room temperature for 30 minutes, poured into saturated sodium bicarbonate, extracted with diethyl ether; the organic phase is washed with water and brine, dried over sodium sulfate, and concentrated in vacuo. The residue is purified by flash-chromatography (silica gel hexane/ethyl acetate) providing 4"-(S)—O-[(hydrazino)carbonyl]avermectin B1, which is characterized by its mass and NMR spectra.

4"-(S)—O-[(hydrazino)carbonyl]avermectin B1: $B_{1a}$ $C_{49}H_{74}N_2O_{15}$ MW: 930.5 LCMS: $t_{RT}$: 7.05, 931.3 (M+H); $B_{1b}$ $C_{48}H_{72}N_2O_{15}$ MW: 916.5 LCMS: $t_{RT}$: 8.43, 917.5 (M+H).

Example P.15

4"-(S)—O-[(phenylsulfamido)carbonyl]avermectin B1

Step A: To a solution of 5-O-tert-butyldimethylsilyl-avermectin B1 (600 mg) in dichloromethane (12 ml) at 0° C. is added dropwise chlorosulfonylisocyanate (129 mg). After stirring at 0° C. for 45 minutes, aniline (283 mg), is added water is added, and the mixture is stirred at room temperature for 3 hours, poured into water, extracted with dichloromethane; the organic phase is washed with water and brine, dried over sodium sulfate, and concentrated in vacuo. The crude residue obtained is used as such in the next step.

Step B: To a solution of the crude residue obtained in step A in 5 ml tetrahydrofuran is added 1 ml of a HF-pyridine solution (consisting of 25 g 70% HF-Pyridin, 27.5 ml tetrahydrofuran and 12.5 ml pyridine), and the mixture is stirred at room temperature for 16 hours, poured into water, extracted with ethyl acetate; the organic phase is washed with saturated sodium bicarbonate, dried over sodium sulfate, and concentrated in vacuo. The residue is purified by flash-chromatography (silica gel hexane/ethyl acetate) providing 4"-O—(S)-[(phenylsulfamido)carbonyl]avermectin B1, which is characterized by its mass and NMR spectra.

4"-(S)—O-[(phenylsulfamido)carbonyl]avermectin B1: $B_{1a}$ $C_{55}H_{78}N_2O_{17}S$ MW: 1070.5 LCMS: $t_{RT}$: 9.54, 1071.5 (M+H), 1093.5 (M+Na).

Example P.16

4"-(R)—O-[(methylamino)carbonyl]avermectin B1

Step A: To a solution of 5-O-tert-butyldimethylsilyl-4"-(R)-avermectin B1 (9.87 g) in dichloromethane (100 ml) is added 4-dimethylaminopyridine (2.5 g) and 1,1'-carbonyldiimidazole (5.4 g). The mixture is stirred at room temperature for 2 hours after which time the mixture is poured into water. Extraction with dichloromethane is followed by drying of the organic extracts over magnesium sulphate, filtration and removal of the solvent by distillation under reduced pressure. The crude material obtained is purified by flash column chromatography on silica gel (hexane/ethyl acetate) yielding 5-O-tert-butyldimethylsilyl-4"-(R)—O-[(imidazol-1-yl)-carbonyl]avermectin B1 which is characterized by its mass and nmr spectra.

Step B: To a solution of 5-O-tert-butyldimethylsilyl-4"-(R)—O-[(imidazol-1-yl)-carbonyl]avermectin B1 obtained above in methanol (100 ml) cooled in an ice bath is added methanesulphonic acid (2 ml). The mixture is stirred for 30 minutes at room temperature after which time the mixture is poured into saturated sodium hydrogen carbonate. Extraction with ethyl acetate is followed by drying of the organic extracts over magnesium sulphate, filtration and removal of the solvent by distillation under reduced pressure. The crude material obtained is purified by flash column chromatography on silica gel (hexane/ethyl acetate) yielding 4"-(R)—O-[(imidazol-1-yl)-carbonyl]avermectin B1, which is characterized by its mass and nmr spectra.

Step C: To a solution of 4"-(R)—O-[(imidazol-1-yl)-carbonyl]avermectin B1 (1.9 g) in acetonitrile (10 ml) at room temperature is added methyl iodide (3 ml). The mixture is stirred for 3 hours after which time the volatile components are removed by distillation under reduced pressure affording 4'-(R)—O-[(3-carbonyl-1-methyl-3H-imidazol-1-ium)iodide]avermectin B1, which is characterized by its mass spectra.

Step D: To a solution of 4"-(R)—O-[(3-carbonyl-1-methyl-3H-imidazol-1-ium)iodide]avermectin B1 (222 mg) in dichloromethane (4 ml) is added methylamine hydrochloride (81 mg) and triethylamine (88 µl). After stirring at room temperature for 2 hours, water is added and the mixture is extracted with dichloromethane. Drying of the organic extracts over magnesium sulphate is followed by filtration and removal of the solvent by distillation under reduced pressure. The crude material obtained is purified by flash column chromatography on silica gel (hexane/ethyl acetate) yielding 4"-(R)—O-[(methylamino)carbonyl]avermectin B1, which is characterized by its mass and nmr spectra.

4"-(R)—O-[(methylamino)carbonyl]avermectin B1: $B_{1a}$ $C_{50}H_{75}NO_{15}$ MW: 929.5 LCMS: $t_{RT}$: 8.59, 930.5 (M+H), 952.5 (M+Na).

Example P.17

4"-(R)—O-[(4-methoxyphenylamino)carbonyl]avermectin B1

To a solution of 4'-(R)—O-[(3-carbonyl-1-methyl-3H-imidazol-1-ium)iodide]avermectin B1 (Example P16, Step C, 222 mg) in dichloromethane (4 ml) is added 4-methoxyaniline (123 mg). After stirring at room temperature for 2 hours, water is added and the mixture is extracted with dichloromethane. Drying of the organic extracts over magnesium sulphate is followed by filtration and removal of the solvent by distillation under reduced pressure. The crude material obtained is purified by flash column chromatography on silica gel (hexane/ethyl acetate) yielding 4'-(R)—O-[(4-methoxyphenylamino)carbonyl]avermectin B1, which is characterized by its mass and nmr spectra.

4"-(R)—O-[(4-methoxyphenylamino)carbonyl]avermectin B1: $B_{1a}$ $C_{56}H_{79}NO_{16}$ MW: 1021.5 LCMS: $t_{RT}$: 10.27, 1022.5 (M+H).

Example P.18

4"-(S)—O-[(methylamino)thiocarbonyl)]-avermectin B1

Step A: To a solution of 5-O-tert-butyldimethylsilyl avermectin B1 (1.48 g) in acetonitrile (15 ml) is added 4-dimethylaminopyridine (183 mg) and 1,1'-thiocarbonyldiimidazole (800 mg). After stirring at room temperature for 12 hours, water is added and the mixture is extracted with diethyl ether, washed with HCl 1N, water, saturated sodium bicarbonate and brine. Drying of the organic extracts over sodium sulphate is followed by filtration and removal of the solvent by distillation under reduced pressure, providing 5-O-tert-butyldimethylsilyl-4"-O-[(Imidazol-1-yl)thiocarbonyl]-avermectin B1, which is characterized by its mass and NMR spectra.

Step B: To a solution of 5-O-tert-butyldimethylsilyl-4"-(S)—O-[(imidazol-1-yl)thiocarbonyl]-avermectin B1 (176 mg) in dimethylformamide (4 ml) is added triethylamine (0.14 ml) and methylamine hydrochloride (68 mg). After stirring at room temperature for 1 hour, water is added and the mixture is extracted with ethyl acetate. Drying of the organic extracts over sodium sulphate is followed by filtration and removal of the solvent by distillation under reduced pressure. The crude residue obtained is used as such for the next step.

Step C: To a solution of the crude residue obtained in step B in 2 ml tetrahydrofuran is added 0.75 ml of a HF-pyridine solution (consisting of 25 g 70% HF-Pyridine, 27.5 ml tetrahydrofuran and 12.5 ml pyridine), and the mixture is stirred at room temperature for 24 hours, poured into water, extracted with ethyl acetate; the organic phase is washed with saturated sodium bicarbonate, dried over sodium sulfate, and concentrated in vacuo. The residue is purified by flash-chromatography (silica gel hexane/ethyl acetate) providing 4"-O—(S)-[(methylamino)thiocarbonyl)]-avermectin B1, which is characterized by its mass and NMR spectra.

4"-(S)—O-[(methylamino)thiocarbonyl)]-avermectin B1: $B_{1a}$ $C_{50}H_{75}NO_{14}S$ MW: 945.5 LCMS: $t_{RT}$: 10.87, 946.6 (M+H); $B_{1b}$ $C_{49}H_{73}NO_{14}S$ MW: 931.5 LCMS: $t_{RT}$: 10.15, 932.3 (M+H).

Example P.19

4"-(S)—O-[(cyanomethylamino)thiocarbonyl)]-avermectin B1

Step A: To a solution of 5-O-tert-butyldimethylsilyl-4"-(S)—O-[(imidazol-1-yl)thiocarbonyl]-avermectin B1 (Example P18, Step A, 3.36 g) in 15 ml tetrahydrofuran is added 5 ml of a HF-pyridine solution (consisting of 25 g 70% HF-Pyridin, 27.5 ml tetrahydrofuran and 12.5 ml pyridine), and the mixture is stirred at room temperature for 48 hours, poured into water, extracted with ethyl acetate; the organic phase is washed with saturated sodium bicarbonate, dried over sodium sulfate, and concentrated in vacuo. The residue is purified by flash-chromatography (silica gel hexane/ethyl acetate) providing 4"-O-[(Imidazol-1-yl)-thiocarbonyl]-avermectin B1, which is characterized by its mass and NMR spectra.

Step B: To a solution of 4"-(S)—O-[(imidazol-1-yl)thiocarbonyl]-avermectin B1 (220 mg) in dimethylformamide (5 ml) is added triethylamine (0.14 ml) and cyanomethylamine hydrochloride (410 mg). After stirring at room temperature for 3 hours, water is added and the mixture is extracted with diethyl ether. Drying of the organic extracts over sodium sulphate is followed by filtration and removal of the solvent by distillation under reduced pressure. The residue is purified by preparative HPLC providing 4"-O—[(cyanomethylamino)thiocarbonyl)]avermectin B1, which is characterized by its mass and NMR spectra.

4"-(S)—O-[(cyanomethylamino)thiocarbonyl)]-avermectin B1: $B_{1a}$ $C_{51}H_{74}N_2O_{14}S$ MW: 970.5 LCMS: $t_{RT}$: 11.02, 971.9 (M+H); $B_{1b}$ $C_{50}H_{72}N_2O_{14}S$ MW: 956.5 LCMS: $t_{RT}$: 10.36, 957.3 (M+H).

Example P.20

4"-(S)—O-[(2-methylhydrazino)thiocarbonyl)]-avermectin B1

To a solution of 4"-(S)—O-[(imidazol-1-yl)thiocarbonyl]-avermectin B1 (Example P19, Step A, 160 mg) in dimethylformamide (5 ml) is added methylhydrazine (16 mg). After stirring at room temperature for 12 hours, saturated sodium bicarbonate is added and the mixture is extracted with diethyl ether. Drying of the organic extracts over sodium sulphate is followed by filtration and removal of the solvent by distillation under reduced pressure. The residue is purified by preparative HPLC providing 4'-O-[(2-methylhydrazino)thiocarbonyl)]-avermectin B1, which is characterized by its mass and NMR spectra.

4"-(S)—O-[(2-methylhydrazino)thiocarbonyl]avermectin B1: $B_{1a}$ $C_{50}H_{76}N_2O_{14}S$ MW: 960.5 LCMS: $t_{RT}$: 9.66, 961.6 (M+H).

Example P.21

4'-(S)—O-[allyloxycarbonyl)]-avermectin B1 monosaccharide

Step A: To a solution of 5-O-tert-butyldimethylsilyl avermectin B1 monosaccharide (500 mg) in dichloromethane (5 ml) and pyridine (190 µl) is added allylchloroformate (172 mg) and 4-dimethylaminopyridine (36 mg). The mixture is stirred at room temperature for 48 hours after which time the mixture is poured into aqueous ammonium chloride. Extraction with ethyl acetate is followed by drying of the organic extracts over magnesium sulphate, filtration and removal of the solvent by distillation under reduced pressure. The crude material obtained is purified by flash column chromatography on silica gel (hexane/ethyl acetate) yielding 5-O-tert-butyldimethylsilyl-4'-(S)—O-[allyloxycarbonyl)]-avermectin B1 monosaccharide, which is characterized by its mass and nmr spectra.

Step B: To a solution of the 63 mg of 5-O-tert-butyldimethylsilyl-4'-(S)—O-[allyloxycarbonyl)]-avermectin B1 monosaccharide obtained in step A in 1.5 ml methanol is added 5 µl of methanesulfonic acid, and the mixture is stirred for 40 minutes, poured into saturated sodium bicarbonate, extracted with diethyl ether; the organic phase is washed with water and brine, dried over sodium sulfate, and concentrated in vacuo. The residue is purified by flash-chromatography (silica gel hexane/ethyl acetate) providing 4'-(S)—O-[allyloxycarbonyl)]-avermectin B1 monosaccharide which is characterized by its mass and NMR spectra.

4'-(S)—O-[allyloxycarbonyl)]-avermectin B1 monosaccharide: $B_{1a}$ $C_{45}H_{64}O_{13}$ MW: 812.4 LCMS: $t_{RT}$: 10.24 minutes, 935.4 (M+Na); $B_{1b}$ $C_{44}H_{62}O_{13}$ MW: 798.4 LCMS: $t_{RT}$: 9.55 minutes, 821.4 (M+Na).

Example P.22

4'-(S)—O-[(methoxy)thiocarbonyl)]-avermectin B1 monosaccharide

To a solution of 5-O-tert-butyldimethylsilyl 4'-O-[(imidazol-1-yl)-thiocarbonyl]-avermectin B1 monosaccharide (381 mg) from Example P.7 (step A) in methanol (6.5 ml) cooled in an ice bath is added a solution of methanesulphonic acid (55 mg). The mixture is stirred for 24 hours after which time the mixture is poured into saturated sodium hydrogen carbonate (10 ml). Extraction with ethyl acetate is followed by drying of the organic extracts over magnesium sulphate, filtration and removal of the solvent by distillation under reduced pressure. The crude material obtained is purified by flash column chromatography on silica gel (hexane/ethyl acetate) yielding 4'-(S)—O-[(methoxy)thiocarbonyl)]-avermectin B1 monosaccharide which is characterized by its mass and nmr spectra.

4'-(S)—O-[(methoxy)thiocarbonyl)]-avermectin B1 monosaccharide: $B_{1a}$ $C_{43}H_{62}O_{12}S$, MW: 802.4 LCMS: $t_{RT}$: 10.88 min., 825.5 (M+Na); $B_{1b}$ $C_{42}H_{60}O_{12}S$ MW: 788.4 LCMS: $t_{RT}$: 10.24 min., 811.2 (M+Na).

Similarly to the preparation examples above it is also possible to prepare the corresponding compounds listed in Tables.

TABLE 1

Compounds of the formula

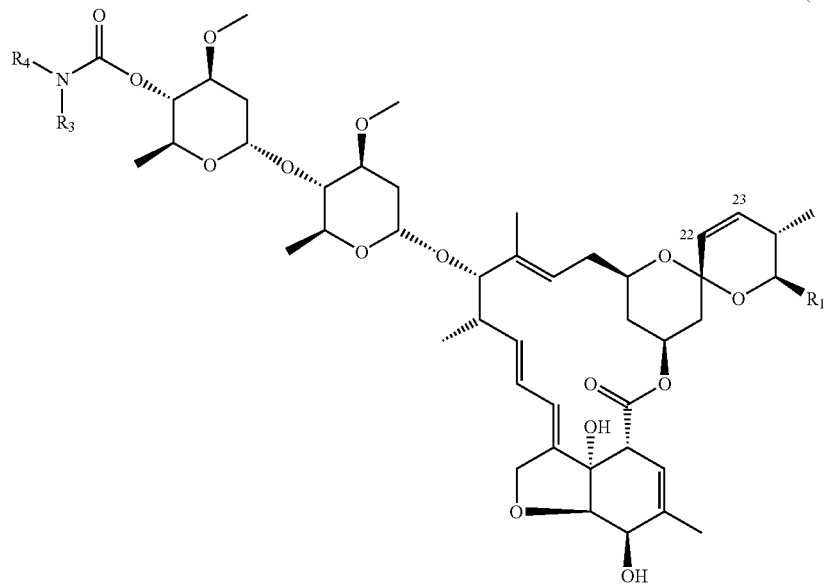

(Ic)

in which $R_1$ is sec-butyl (B1a) or isopropyl (B1b)

| No. | $R_3$ | $R_4$ | Retention time (min) | |
| --- | --- | --- | --- | --- |
| | | | B1a | B1b |
| 1.1 | H | $CH_3$ | 9.10 | |
| 1.2 | H | $CH_2CH_3$ | | |
| 1.3 | H | $n-C_3H_7$ | | |
| 1.4 | H | $i-C_3H_7$ | 10.22 | 9.46 |
| 1.5 | H | $n-C_4H_9$ | | |
| 1.6 | H | $i-C_4H_9$ | | |
| 1.7 | H | $sec-C_4H_9$ | | |
| 1.8 | H | $t-C_4H_9$ | | |
| 1.9 | H | $n-C_5H_{11}$ | | |
| 1.10 | H | $n-C_6H_{13}$ | | |
| 1.11 | H | $Cyclo-C_5H_9$ | | |
| 1.12 | H | $CH_2C_6H_5$ | | |
| 1.13 | H | $Cyclo-C_6H_{11}$ | | |
| 1.14 | H | $p-NO_2C_6H_5$ | | |
| 1.15 | H | $CH_2CH_2OCH_3$ | 10.40 | 9.66 |
| 1.16 | H | $CH_2(CH_2)_2OCH_2CH_3$ | | |
| 1.17 | H | $CH_2CH{=}CH_2$ | 9.85 | 9.10 |
| 1.18 | H | $CH_2$-(tetrahydrofuran-2-yl) | 10.86 | 10.10 |
| 1.19 | H | $CH_2CH_2OH$ | 8.88 | 8.11 |
| 1.20 | H | $CH(CH_3)CH(OCH_3)_2$ | | |
| 1.21 | H | Cyclopropyl | 9.73 | 8.96 |
| 1.22 | H | $CH_2CH(OH)CH_2OH$ | 6.96 | 6.23 |
| 1.23 | H | $CH_2CH(OCH_3)_2$ | 9.41 | 8.69 |
| 1.24 | $CH_2CH_2OCH_2CH_2$ | | 10.91 | 10.13 |
| 1.25 | H | $CH_2CH_2F$ | | |
| 1.26 | H | $CH_2CF_3$ | 10.25 | 9.54 |
| 1.27 | H | $CH_2CH_2N(CH_3)_2$ | | |
| 1.28 | H | $OCH_3$ | | |
| 1.29 | H | 1-naphthyl | 12.37 | 11.85 |

TABLE 1-continued

| | | | | |
|---|---|---|---|---|
| 1.30 | H | CH$_2$–(pyrrolidin-1-yl) | 6.13 | 5.71 |
| 1.31 | H | CH$_2$–(pyridin-4-yl) | 6.11 | 5.72 |
| 1.32 | CH$_2$CH$_2$OH | CH$_2$CH$_2$OH | 8.38 | 7.62 |
| 1.33 | H | CH$_2$CH$_2$NH$_2$ | 5.44 | 5.04 |
| 1.34 | | CH$_2$(CH$_2$)$_3$CH$_2$ | 12.33 | 11.61 |
| 1.35 | H | CH$_2$(CH$_2$)$_3$NH$_2$ | 5.84 | 5.43 |
| 1.36 | H | CH$_2$(CH$_2$)$_5$NH$_2$ | 6.29 | 5.86 |
| 1.37 | H | CH$_2$(CH$_2$)$_2$O(CH$_2$)$_3$NH$_2$ | 6.16 | 5.74 |
| 1.38 | | CH$_2$(CH$_2$)$_2$CH$_2$ | 11.01 | |
| 1.39 | H | CH$_2$–(furan-2-yl) | 9.96 | 9.28 |
| 1.40 | H | CH$_2$–(pyridin-2-yl) | 5.99 | |
| 1.41 | H | CH$_2$CH$_2$NHCH$_3$ | 4.79 | 4.40 |
| 1.42 | H | CH$_2$–C≡CH | 9.32 | 8.72 |
| 1.43 | H | CH$_2$(CH$_2$)$_2$Cl | 10.13 | 9.38 |
| 1.44 | H | CH$_2$CH$_2$N$^+$Me$_3$I$^-$ | 5.52 | 5.12 |
| 1.45 | H | NH$_2$ | 7.10 | 6.40 |
| 1.46 | H | NHMe | 8.22 | 7.47 |
| 1.47 | H | NMe$_2$ | 9.13 | 8.44 |
| 1.48 | H | NHOMe | | |
| 1.49 | H | CH$_2$CH$_2$OS(O)$_2$NH$_2$ | 7.93 | 7.20 |
| 1.50 | H | OH | 7.80 | 7.16 |
| 1.51 | H | S(O)$_2$NHBenzyl | 9.88 | 9.24 |
| 1.52 | H | S(O)$_2$NH$_2$ | 8.00 | |
| 1.53 | H | S(O)$_2$NHPh | 9.56 | 8.88 |
| 1.54 | H | pMeOC$_6$H$_5$ | | |
| 1.55 | H | (CH$_2$)$_{12}$NH$_2$ | 8.29 | 7.79 |
| 1.56 | H | trans-2-methylcyclohexylamine | 6.74 | |
| 1.57 | H | CH(CH$_3$)CH$_2$CH$_3$ | 10.60 | 10.02 |
| 1.58 | H | (CH$_2$)$_4$N$^+$Me$_3$I$^-$ | 5.15 | |
| 1.59 | H | (CH$_2$)$_6$N$^+$Me$_3$I$^-$ | 5.54 | |
| 1.60 | H | (CH$_2$)$_3$O(CH$_2$)$_3$N$^+$Me$_3$I$^-$ | 5.31 | |
| 1.61 | H | (CH$_2$)$_{12}$N$^+$Me$_3$I$^-$ | 7.61 | |
| 1.62 | H | trans-2-methylcyclohexyl-NMe$_3$$^+$ I$^-$ | 6.13 | |
| 1.63 | H | 2-phenylcyclopropyl | 10.94 | 10.38 |
| 1.64 | CH$_3$ | CH$_3$ | | |
| 1.65 | CH$_3$ | CH$_2$CH$_3$ | | |
| 1.66 | CH$_3$ | n-C$_3$H$_7$ | | |
| 1.67 | CH$_3$ | i-C$_3$H$_7$ | | |

TABLE 1-continued

| | | | | |
|---|---|---|---|---|
| 1.68 | $CH_3$ | $n\text{-}C_4H_9$ | | |
| 1.69 | $CH_3$ | $i\text{-}C_4H_9$ | | |
| 1.70 | $CH_3$ | $Sec\text{-}C_4H_9$ | | |
| 1.71 | $CH_3$ | $t\text{-}C_4H_9$ | | |
| 1.72 | $CH_3$ | $n\text{-}C_5H_{11}$ | | |
| 1.73 | $CH_3$ | $n\text{-}C_6H_{13}$ | | |
| 1.74 | $CH_2CH_3$ | $CH_2CH_3$ | | |
| 1.75 | $CH_2CH_3$ | $n\text{-}C_3H_7$ | | |
| 1.76 | $CH_2CH_3$ | $i\text{-}C_3H_7$ | | |
| 1.77 | $CH_2CH_3$ | $n\text{-}C_4H_9$ | | |
| 1.78 | $CH_2CH_3$ | $i\text{-}C_4H_9$ | | |
| 1.79 | $CH_2CH_3$ | $Sec\text{-}C_4H_9$ | | |
| 1.80 | $CH_2CH_3$ | $t\text{-}C_4H_9$ | | |
| 1.81 | $CH_2CH_3$ | $n\text{-}C_5H_{11}$ | | |
| 1.82 | $CH_2CH_3$ | $n\text{-}C_6H_{13}$ | | |
| 1.83 | H | H | | |
| 1.84 | H | $C_6H_5$ | 13.7 | |
| 1.85 | H | N-phthalimidyl group | 12.85 | 12.43 |
| 1.86 | H | $CH_2CH_2Cl$ | 9.38 | 8.83 |
| 1.87 | H | $CH_2CH_2SCH_3$ | 9.45 | 8.90 |
| 1.88 | H | $CH_2CH_2SCH_2CH_3$ | 9.96 | 9.44 |
| 1.89 | H | $C(CH_3)_2CH_2SCH_3$ | 10.56 | |
| 1.90 | | $CH_2CH_2SCH_2CH_2$ | 10.0 | 9.47 |
| 1.91 | H | $CH_2CH_2OCH_2CH_3$ | 9.08 | 8.50 |
| 1.92 | H | $CH_2CH_2OCH_2(CH_3)_2$ | 9.57 | 9.03 |

TABLE 2

Compounds of the formula (Id)

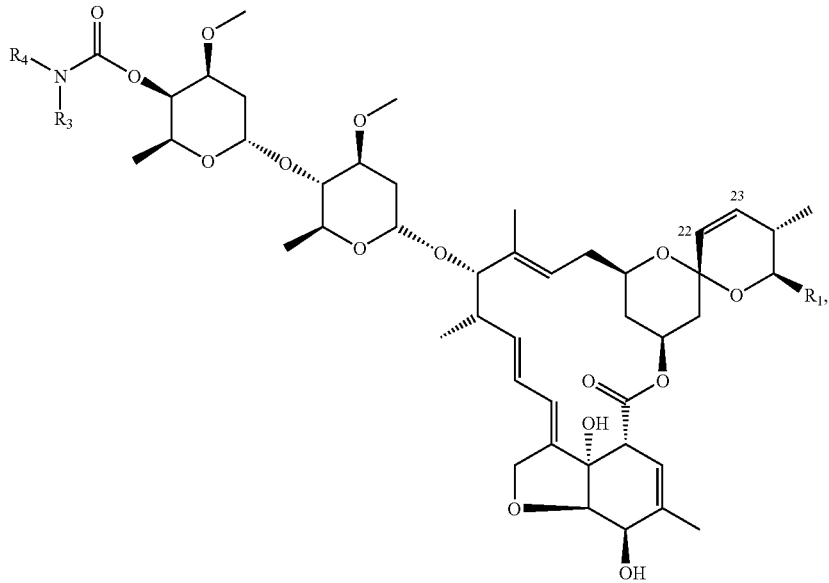

in which $R_1$ is sec-butyl (B1a) or isopropyl (B1b)

| | | | Retention time (min) | |
|---|---|---|---|---|
| No. | $R_3$ | $R_4$ | B1a | B1b |
| 2.1 | H | $pNO_2C_6H_5$ | | |
| 2.2 | H | $CH_3$ | 8.59 | 7.79 |
| 2.3 | H | $CH_3CH_2$ | 9.33 | 8.54 |
| 2.4 | H | $Cyclo\text{-}C_5H_9$ | | |

TABLE 2-continued

| | | | | |
|---|---|---|---|---|
| 2.5 | H | CH$_2$CH(CH$_3$)$_2$ | | |
| 2.6 | H | CH$_2$C$_6$H$_5$ | | |
| 2.7 | H | Cyclo-C$_6$C$_{11}$ | | |
| 2.8 | H | CH$_2$(CH$_2$)$_4$CH$_3$ | | |
| 2.9 | H | CH$_2$CH$_2$CH$_3$ | | |
| 2.10 | H | CH$_2$CH$_2$OCH$_3$ | 8.71 | 7.91 |
| 2.11 | H | CH(CH$_3$)$_2$ | 9.98 | 9.19 |
| 2.12 | H | CH$_2$(CH$_2$)$_2$OCH$_2$CH$_3$ | | |
| 2.13 | H | CH$_2$CH=CH$_2$ | | |
| 2.14 | H | 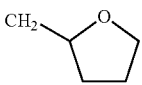 | 9.17 | 8.36 |
| 2.15 | H | CH$_2$CH$_2$OH | 7.05 | 6.36 |
| 2.16 | H | CH(CH$_3$)CH(OCH$_3$)$_2$ | | |
| 2.17 | H |  | 9.33 | 8.67 |
| 2.18 | H | CH$_2$CH(OH)CH$_2$OH | | |
| 2.19 | H | CH$_2$CH(OCH$_3$)$_2$ | | |
| 2.20 | | CH$_2$CH$_2$OCH$_2$CH$_2$ | | |
| 2.21 | H | CH$_2$CH$_2$F | | |
| 2.22 | H | CH$_2$CF$_3$ | | |
| 2.23 | H | CH$_2$CH$_2$N(CH$_3$)$_2$ | | |
| 2.24 | H | OCH$_3$ | | |
| 2.25 | H | 1- 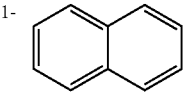 | | |
| 2.26 | H | 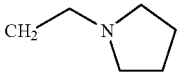 | 5.62 | |
| 2.27 | H | 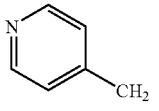 | 6.04 | 5.72 |
| 2.28 | CH$_2$CH$_2$OH | CH$_2$CH$_2$OH | | |
| 2.29 | CH$_2$CH$_2$NH$_2$ | CH$_2$CH$_2$NH$_2$ | | |
| 2.30 | | CH$_2$(CH$_2$)$_3$CH$_2$ | 12.57 | 11.87 |
| 2.31 | H | CH$_2$(CH$_2$)$_3$NH$_2$ | | |
| 2.32 | H | CH$_2$(CH$_2$)$_5$NH$_2$ | | |
| 2.33 | H | CH$_2$(CH$_2$)$_2$O(CH$_2$)$_3$NH$_2$ | | |
| 2.34 | | CH$_2$(CH$_2$)$_2$CH$_2$ | 5.62 | 5.14 |
| 2.35 | H | 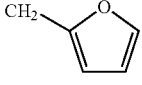 | | |
| 2.36 | H | 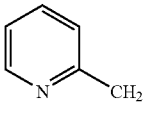 | | |
| 2.37 | H | CH$_2$CH$_2$NHCH$_3$ | | |
| 2.38 | H | CH$_2$C≡CH | | |
| 2.39 | H | CH$_2$(CH$_2$)$_2$Cl | | |
| 2.40 | H | CH$_2$CH$_2$N$^+$Me$_3$I$^-$ | | |
| 2.41 | CH$_2$CH$_3$ | CH$_2$CH$_3$ | | |
| 2.42 | H | NH$_2$ | | |
| 2.43 | H | NHMe | | |
| 2.44 | H | NMe$_2$ | | |
| 2.45 | H | NHOMe | | |
| 2.46 | H | CH$_2$CH$_2$OS(O)$_2$NH$_2$ | | |
| 2.47 | H | NHOH | | |
| 2.48 | H | S(O)$_2$NHBenzyl | | |
| 2.49 | H | S(O)$_2$NH$_2$ | | |
| 2.50 | H | S(O)$_2$NHPh | | |

TABLE 2-continued
| | | | | |
|---|---|---|---|---|
| 2.51 | H | pMeOC$_6$H$_5$ | 10.33 | 9.74 |
| 2.52 | CH$_3$ | CH$_3$ | | |
| 2.53 | CH$_3$ | CH$_2$CH$_3$ | | |
| 2.54 | CH$_3$ | n-C$_3$H$_7$ | | |
| 2.55 | CH$_3$ | i-C$_3$H$_7$ | | |
| 2.56 | CH$_3$ | n-C$_4$H$_9$ | | |
| 2.57 | CH$_3$ | i-C$_4$H$_9$ | | |
| 2.58 | CH$_3$ | Sec-C$_4$H$_9$ | | |
| 2.59 | CH$_3$ | t-C$_4$H$_9$ | | |
| 2.60 | CH$_3$ | n-C$_5$H$_{11}$ | | |
| 2.61 | CH$_3$ | n-C$_6$H$_{13}$ | | |
| 2.62 | CH$_2$CH$_3$ | n-C$_3$H$_7$ | | |
| 2.63 | CH$_2$CH$_3$ | i-C$_3$H$_7$ | | |
| 2.64 | CH$_2$CH$_3$ | n-C$_4$H$_9$ | | |
| 2.65 | CH$_2$CH$_3$ | i-C$_4$H$_9$ | | |
| 2.66 | H | H | 8.16 | 7.47 |
| 2.67 | H | n-C$_4$H$_9$ | | |
| 2.68 | H | i-C$_4$H$_9$ | | |
| 2.69 | H | sec-C$_4$H$_9$ | | |
| 2.70 | H | t-C$_4$H$_9$ | | |
| 2.71 | H | n-C$_5$H$_{11}$ | | |
| 2.72 | H | n-C$_6$H$_{13}$ | | |
| 2.73 | H | 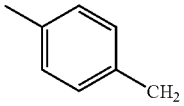 | 13.74 | |
| 2.74 | H | C$_6$H$_5$ | 13.48 | |
| 2.75 | CH$_3$ | C$_6$H$_5$ | 13.59 | |
| 2.76 | H | 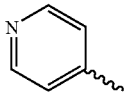 | 5.62 | |
| 2.77 | H | 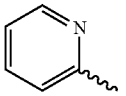 | 11.24 | |
| 2.78 | H | 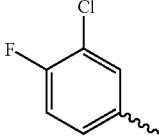 | 14.09 | |
| 2.79 | H | 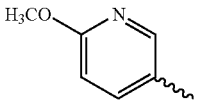 | 12.82 | |
| 2.80 | H | 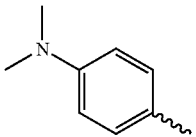 | 8.00 | |
| 2.81 | CH$_3$ | 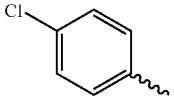 | 13.97 | |
| 2.82 | H | 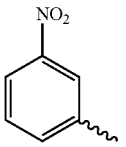 | 13.71 | |
| 2.83 | H | CH$_2$CH$_2$Cl | 8.96 | 8.40 |

TABLE 2-continued

| | | | | |
|---|---|---|---|---|
| 2.84 | H | $CH_2CH_2SCH_3$ | 9.02 | 8.45 |
| 2.85 | H | $C(CH_3)_2CH_2SCH_3$ | 10.22 | 9.73 |
| 2.86 | H | $CH_2CH_2SCH_2CH_3$ | 9.59 | 9.06 |
| 2.87 | | $CH_2CH_2SCH_2CH_2$ | 9.77 | 9.21 |
| 2.88 | H | $CH_2CH_2OCH_2CH_3$ | 8.55 | 7.96 |
| 2.89 | H | $CH_2CH_2OCH_2(CH_3)_2$ | 9.10 | 8.54 |

TABLE 3

Compounds of the formula

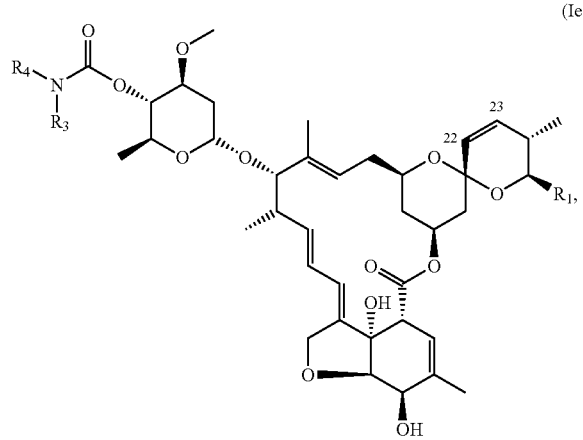

(Ie)

in which $R_1$ is sec-butyl (B1a) or isopropyl (B1b)

| No. | $R_3$ | $R_4$ | B1a | B1b |
|---|---|---|---|---|
| 3.1 | H | $pNO_2C_6H_5$ | 10.04 | |
| 3.2 | H | $CH_3$ | 7.15 | 6.51 |
| 3.3 | H | $CH_3CH_2$ | 8.97 | |
| 3.4 | H | Cyclo-$C_5H_9$ | 8.96 | 8.37 |
| 3.5 | H | $CH_2CH(CH_3)_2$ | 8.59 | 7.95 |
| 3.6 | H | $CH_2C_6H_5$ | 8.80 | 8.16 |
| 3.7 | H | Cyclo-$C_6C_{11}$ | 9.49 | 8.85 |
| 3.8 | H | $CH_2(CH_2)_4CH_3$ | 10.08 | 9.44 |
| 3.9 | H | $CH_2CH_2CH_3$ | 8.27 | 7.63 |
| 3.10 | H | $CH_2CH_2OCH_3$ | 8.21 | 7.57 |
| 3.11 | H | $CH(CH_3)_2$ | 8.27 | 7.63 |
| 3.12 | H | $CH_2(CH_2)_2OCH_2CH_3$ | 8.48 | 7.79 |
| 3.13 | H | $CH_2CH=CH_2$ | 8.75 | 8.16 |
| 3.14 | H | $CH_2$-tetrahydrofuranyl | 8.48 | 7.84 |
| 3.15 | H | $CH_2CH_2OH$ | 6.77 | 6.13 |
| 3.16 | H | $CH(CH_3)CH(OCH_3)_2$ | 9.01 | 8.27 |
| 3.17 | H | Cyclo-$C_3H_5$ | 8.43 | 7.79 |
| 3.18 | H | $CH_2CH(OH)CH_2OH$ | 6.24 | 5.60 |
| 3.19 | H | $CH_2CH(OCH_3)_2$ | 8.21 | 7.52 |
| 3.20 | | $CH_2CH_2OCH_2CH_2$ | 8.32 | 7.63 |
| 3.21 | H | $CH_2CH_2F$ | 8.05 | 7.47 |
| 3.22 | H | $CH_2CF_3$ | 8.96 | 8.27 |
| 3.23 | H | $CH_2CH_2N(CH_3)_2$ | 4.37 | 4.05 |
| 3.24 | H | $OCH_3$ | | |
| 3.25 | H | 1-naphthyl | | |
| 3.26 | H | $CH_2$-pyrrolidinyl | | |
| 3.27 | H | $CH_2$-(4-pyridyl) | | |
| 3.28 | $CH_2CH_2OH$ | $CH_2CH_2OH$ | | |
| 3.29 | $CH_2CH_2NH_2$ | $CH_2CH_2NH_2$ | | |
| 3.30 | | $CH_2(CH_2)_3CH_2$ | | |
| 3.31 | H | $CH_2(CH_2)_3NH_2$ | | |
| 3.32 | H | $CH_2(CH_2)_5NH_2$ | | |
| 3.33 | H | $CH_2(CH_2)_2O(CH_2)_3NH_2$ | | |
| 3.34 | | $CH_2(CH_2)_2CH_2$ | | |
| 3.35 | H | $CH_2$-furanyl | | |
| 3.36 | H | $CH_2$-(2-pyridyl) | | |
| 3.37 | H | $CH_2CH_2NHCH_3$ | | |
| 3.38 | H | $CH_2C{\equiv}CH$ | | |
| 3.39 | H | $CH_2(CH_2)_2Cl$ | | |
| 3.40 | H | $CH_2CH_2N^+Me_3I^-$ | | |
| 3.41 | $CH_2CH_3$ | $CH_2CH_3$ | | |
| 3.42 | H | $NH_2$ | | |
| 3.43 | H | NHMe | | |
| 3.44 | H | $NMe_2$ | | |
| 3.45 | H | NHOMe | | |
| 3.46 | H | $CH_2CH_2OS(O)_2NH_2$ | | |
| 3.47 | H | NHOH | | |
| 3.48 | H | $S(O)_2$NHBenzyl | | |

TABLE 3-continued

Compounds of the formula

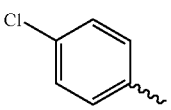

(Ie)

in which $R_1$ is sec-butyl (B1a) or isopropyl (B1b)

| No. | $R_3$ | $R_4$ | Retention time (min) B1a | B1b |
|---|---|---|---|---|
| 3.49 | H | S(O)$_2$NH$_2$ | | |
| 3.50 | H | S(O)$_2$NHPh | | |
| 3.51 | H | pMeOC$_6$H$_5$ | | |
| 3.52 | CH$_3$ | CH$_3$ | | |
| 3.53 | CH$_3$ | CH$_2$CH$_3$ | | |
| 3.54 | CH$_3$ | n-C$_3$H$_7$ | | |
| 3.55 | CH$_3$ | i-C$_3$H$_7$ | | |
| 3.56 | CH$_3$ | n-C$_4$H$_9$ | | |
| 3.57 | CH$_3$ | i-C$_4$H$_9$ | | |
| 3.58 | CH$_3$ | Sec-C$_4$H$_9$ | | |
| 3.59 | CH$_3$ | t-C$_4$H$_9$ | | |
| 3.60 | CH$_3$ | n-C$_5$H$_{11}$ | | |
| 3.61 | CH$_3$ | n-C$_6$H$_{13}$ | | |
| 3.62 | CH$_2$CH$_3$ | CH$_3$ | | |
| 3.63 | CH$_2$CH$_3$ | n-C$_3$H$_7$ | | |
| 3.64 | CH$_2$CH$_3$ | i-C$_3$H$_7$ | | |
| 3.65 | CH$_2$CH$_3$ | n-C$_4$H$_9$ | | |
| 3.66 | CH$_2$CH$_3$ | i-C$_4$H$_9$ | | |
| 3.67 | H | n-C$_4$H$_9$ | | |
| 3.68 | H | i-C$_4$H$_9$ | | |
| 3.69 | H | sec-C$_4$H$_9$ | | |
| 3.70 | H | t-C$_4$H$_9$ | | |
| 3.71 | H | n-C$_5$H$_{11}$ | | |
| 3.72 | H | n-C$_6$H$_{13}$ | | |
| 3.73 | H | 4-Cl-C$_6$H$_4$ | 13.67 | |

TABLE 3-continued

Compounds of the formula

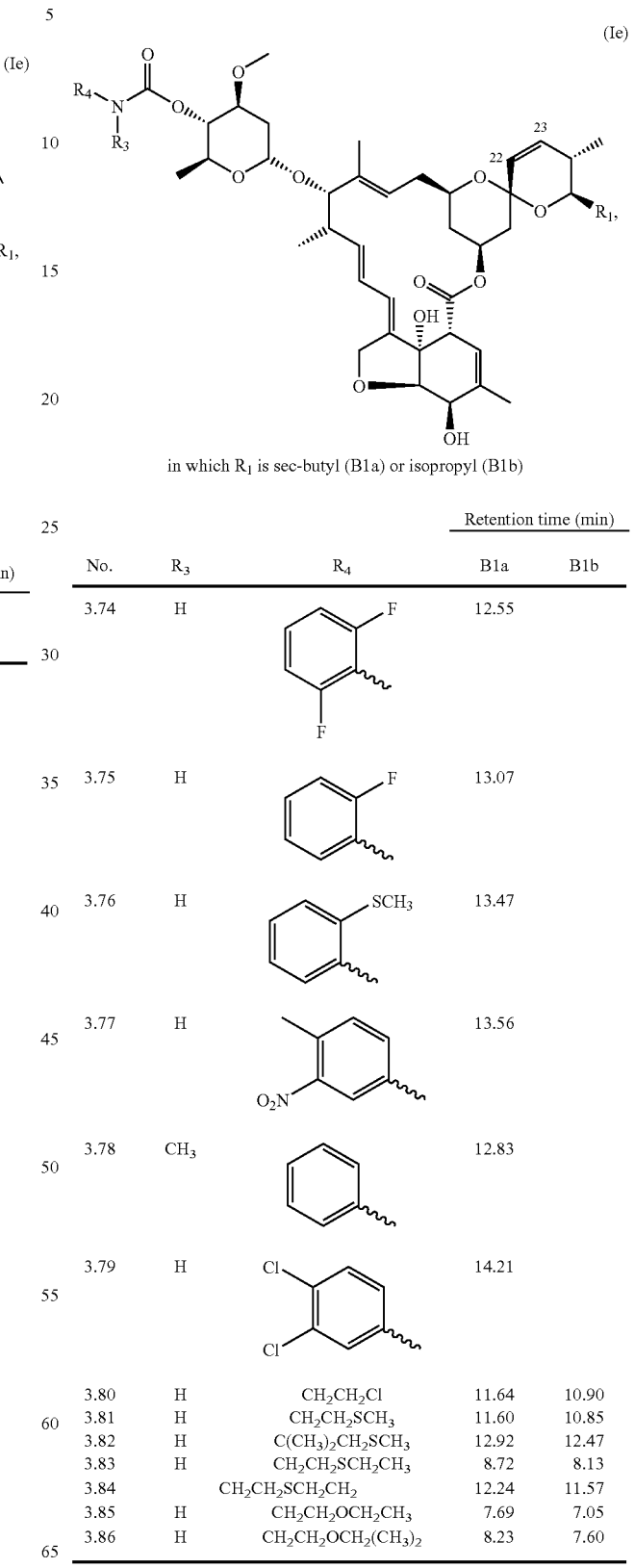

(Ie)

in which $R_1$ is sec-butyl (B1a) or isopropyl (B1b)

| No. | $R_3$ | $R_4$ | Retention time (min) B1a | B1b |
|---|---|---|---|---|
| 3.74 | H | 2,6-F$_2$-C$_6$H$_3$ | 12.55 | |
| 3.75 | H | 2-F-C$_6$H$_4$ | 13.07 | |
| 3.76 | H | 2-SCH$_3$-C$_6$H$_4$ | 13.47 | |
| 3.77 | H | 2-CH$_3$-5-NO$_2$-C$_6$H$_3$ | 13.56 | |
| 3.78 | CH$_3$ | C$_6$H$_5$ | 12.83 | |
| 3.79 | H | 3,4-Cl$_2$-C$_6$H$_3$ | 14.21 | |
| 3.80 | H | CH$_2$CH$_2$Cl | 11.64 | 10.90 |
| 3.81 | H | CH$_2$CH$_2$SCH$_3$ | 11.60 | 10.85 |
| 3.82 | H | C(CH$_3$)$_2$CH$_2$SCH$_3$ | 12.92 | 12.47 |
| 3.83 | H | CH$_2$CH$_2$SCH$_2$CH$_3$ | 8.72 | 8.13 |
| 3.84 | | CH$_2$CH$_2$SCH$_2$ | 12.24 | 11.57 |
| 3.85 | H | CH$_2$CH$_2$OCH$_2$CH$_3$ | 7.69 | 7.05 |
| 3.86 | H | CH$_2$CH$_2$OCH$_2$(CH$_3$)$_2$ | 8.23 | 7.60 |

TABLE 4

Compounds of the formula (If)

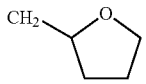

in which $R_1$ is sec-butyl (B1a) or isopropyl (B1b)

| No. | $R_3$ | $R_4$ | Retention time (min) B1a | B1b |
|---|---|---|---|---|
| 4.1 | H | pNO$_2$C$_6$H$_5$ | 8.53 | |
| 4.2 | H | CH$_3$ | 6.98 | 6.43 |
| 4.3 | H | CH$_3$CH$_2$ | 7.18 | |
| 4.4 | H | Cyclo-C$_5$H$_9$ | 9.39 | |
| 4.5 | H | CH$_2$CH(CH$_3$)$_2$ | 8.59 | 7.95 |
| 4.6 | H | CH$_2$C$_6$H$_5$ | 8.69 | 8.16 |
| 4.7 | H | Cyclo-C$_6$C$_{11}$ | 9.49 | 8.85 |
| 4.8 | H | CH$_2$(CH$_2$)$_4$CH$_3$ | 10.30 | 9.66 |
| 4.9 | H | CH$_2$CH$_2$CH$_3$ | 8.00 | 7.36 |
| 4.10 | H | CH$_2$CH$_2$OCH$_3$ | 6.88 | 6.29 |
| 4.11 | H | CH(CH$_3$)$_2$ | 8.21 | 7.63 |
| 4.12 | H | CH$_2$(CH$_2$)$_2$OCH$_2$CH$_3$ | 8.11 | |
| 4.13 | H | CH$_2$CH=CH$_2$ | 7.64 | 7.20 |
| 4.14 | H | 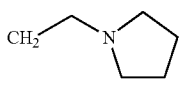 | 7.47 | 6.93 |
| 4.15 | H | CH$_2$CH$_2$OH | 5.73 | 5.33 |
| 4.16 | H | CH(CH$_3$)CH(OCH$_3$)$_2$ | 7.79 | 7.25 |
| 4.17 | H | Cyclo-C$_3$H$_5$ | 7.73 | 7.15 |
| 4.18 | H | CH$_2$CH(OH)CH$_2$OH | 5.23 | |
| 4.19 | H | CH$_2$CH(OCH$_3$)$_2$ | | |
| 4.20 | | CH$_2$CH$_2$OCH$_2$CH$_2$ | | |
| 4.21 | H | CH$_2$CH$_2$F | | |
| 4.22 | H | CH$_2$CF$_3$ | | |
| 4.23 | H | CH$_2$CH$_2$N(CH$_3$)$_2$ | | |
| 4.24 | H | OCH$_3$ | | |
| 4.25 | H | 1-naphthyl | | |
| 4.26 | H | 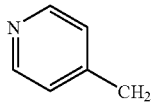 | | |
| 4.27 | H | 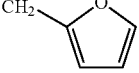 | | |
| 4.28 | CH$_2$CH$_2$OH | CH$_2$CH$_2$OH | | |
| 4.29 | CH$_2$CH$_2$NH$_2$ | CH$_2$CH$_2$NH$_2$ | | |
| 4.30 | | CH$_2$(CH$_2$)$_3$CH$_2$ | | |
| 4.31 | H | CH$_2$(CH$_2$)$_3$NH$_2$ | | |
| 4.32 | H | CH$_2$(CH$_2$)$_5$NH$_2$ | | |
| 4.33 | H | CH$_2$(CH$_2$)$_2$O(CH$_2$)$_3$NH$_2$ | | |
| 4.34 | | CH$_2$(CH$_2$)$_2$CH$_2$ | | |
| 4.35 | H | 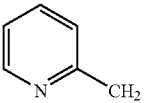 | | |
| 4.36 | H | (2-pyridyl)CH$_2$ | | |
| 4.37 | H | CH$_2$CH$_2$NHCH$_3$ | | |
| 4.38 | H | CH$_2$C≡CH | | |
| 4.39 | H | CH$_2$(CH$_2$)$_2$Cl | | |
| 4.40 | H | CH$_2$CH$_2$N$^+$Me$_3$I$^-$ | | |
| 4.41 | CH$_2$CH$_3$ | CH$_2$CH$_3$ | | |
| 4.42 | H | NH$_2$ | | |
| 4.43 | H | NHMe | | |
| 4.44 | H | NMe$_2$ | | |
| 4.45 | H | NHOMe | | |
| 4.46 | H | CH$_2$CH$_2$OS(O)$_2$NH$_2$ | | |
| 4.47 | H | NHOH | | |
| 4.48 | H | S(O)$_2$NHBenzyl | | |
| 4.49 | H | S(O)$_2$NH$_2$ | | |
| 4.50 | H | S(O)$_2$NHPh | | |
| 4.51 | H | pMeOC$_6$H$_5$ | | |
| 4.52 | CH$_3$ | CH$_3$ | | |
| 4.53 | CH$_3$ | CH$_2$CH$_3$ | | |
| 4.54 | CH$_3$ | n-C$_3$H$_7$ | | |
| 4.55 | CH$_3$ | i-C$_3$H$_7$ | | |
| 4.56 | CH$_3$ | n-C$_4$H$_9$ | | |
| 4.57 | CH$_3$ | i-C$_4$H$_9$ | | |
| 4.58 | CH$_3$ | sec-C$_4$H$_9$ | | |
| 4.59 | CH$_3$ | t-C$_4$H$_9$ | | |
| 4.60 | CH$_3$ | n-C$_5$H$_{11}$ | | |
| 4.61 | CH$_3$ | n-C$_6$H$_{13}$ | | |
| 4.62 | CH$_2$CH$_3$ | CH$_3$ | | |
| 4.63 | CH$_2$CH$_3$ | n-C$_3$H$_7$ | | |
| 4.64 | CH$_2$CH$_3$ | i-C$_3$H$_7$ | | |
| 4.65 | CH$_2$CH$_3$ | n-C$_4$H$_9$ | | |
| 4.66 | CH$_2$CH$_3$ | i-C$_4$H$_9$ | | |
| 4.67 | H | n-C$_4$H$_9$ | | |
| 4.68 | H | i-C$_4$H$_9$ | | |
| 4.69 | H | sec-C$_4$H$_9$ | | |
| 4.70 | H | t-C$_4$H$_9$ | | |
| 4.71 | H | n-C$_5$H$_{11}$ | | |
| 4.72 | H | n-C$_6$H$_{13}$ | | |
| 4.73 | H | CH$_2$CH$_2$Cl | 10.97 | |
| 4.74 | H | CH$_2$CH$_2$SCH$_3$ | 11.04 | |
| 4.75 | H | CH$_2$CH$_2$SCH$_2$CH$_3$ | 8.23 | |
| 4.76 | H | C(CH$_3$)$_2$CH$_2$SCH$_3$ | 12.60 | |
| 4.77 | | CH$_2$CH$_2$SCH$_2$CH$_2$ | 12.16 | |
| 4.78 | H | CH$_2$CH$_2$OCH$_2$CH$_3$ | 6.97 | |
| 4.79 | H | CH$_2$CH$_2$OCH$_2$(CH$_3$)$_2$ | 7.64 | |

TABLE 5

Compounds of the formula

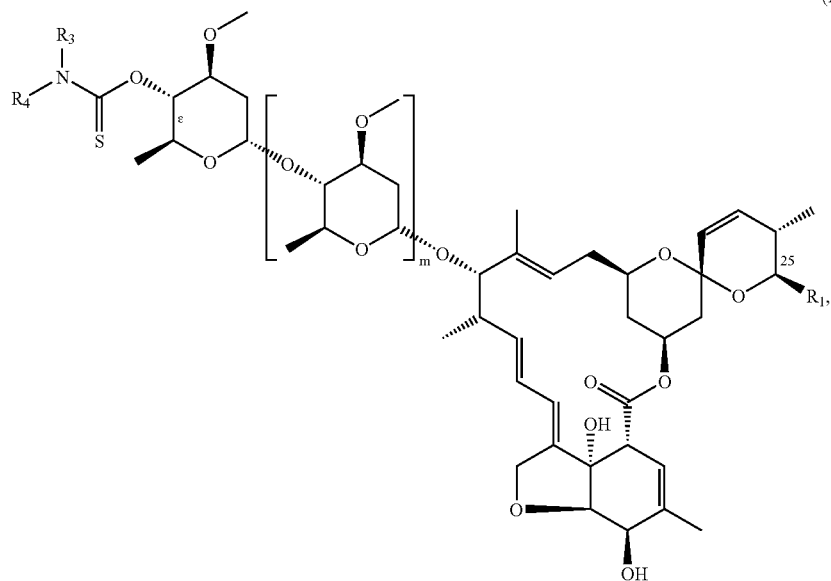

(Ig)

in which $R_1$ is sec-butyl (B1a) or isopropyl (B1b)

| No. | $R_3$ | $R_4$ | m | Retention time (min) B1a | B1b |
|---|---|---|---|---|---|
| 5.1 | H | pNO$_2$C$_6$H$_5$ | 0 | | |
| 5.2 | H | CH$_3$ | 0 | 9.12 | 8.43 |
| 5.3 | H | CH$_3$CH$_2$ | 0 | | |
| 5.4 | H | Cyclo-C$_5$H$_9$ | 0 | 10.93 | 10.35 |
| 5.5 | H | CH$_2$CH(CH$_3$)$_2$ | 0 | 10.88 | 10.24 |
| 5.6 | H | CH$_2$C$_6$H$_5$ | 0 | | |
| 5.7 | H | Cyclo-C$_6$C$_{11}$ | 0 | 11.04 | 10.40 |
| 5.8 | H | CH$_2$(CH$_2$)$_4$CH$_3$ | 0 | 11.63 | |
| 5.9 | H | CH$_2$CH$_2$CH$_3$ | 0 | 10.40 | 9.76 |
| 5.10 | H | CH$_2$CH$_2$OCH$_3$ | 0 | 9.77 | 9.07 |
| 5.11 | H | CH(CH$_3$)$_2$ | 0 | 10.40 | 9.71 |
| 5.12 | H | CH$_2$(CH$_2$)$_2$OCH$_2$CH$_3$ | 0 | 10.14 | 9.44 |
| 5.13 | H | CH$_2$CH=CH$_2$ | 0 | 9.77 | 9.18 |
| 5.14 | H | CH$_2$-(tetrahydrofuran-2-yl) | 0 | | |
| 5.15 | H | CH$_2$CH$_2$OH | 0 | 8.12 | 7.42 |
| 5.16 | H | CH(CH$_3$)CH(OCH$_3$)$_2$ | 0 | | |
| 5.17 | H | cyclopropyl-CH$_2$ | 0 | 9.87 | 9.23 |
| 5.18 | H | CH$_2$CH(OH)CH$_2$OH | 0 | | |
| 5.19 | H | CH$_2$CH(OCH$_3$)$_2$ | 0 | | |
| 5.20 | | CH$_2$CH$_2$OCH$_2$CH$_2$ | 0 | | |
| 5.21 | H | CH$_2$CH$_2$F | 0 | | |
| 5.22 | H | CH$_2$CF$_3$ | 0 | 10.29 | 9.60 |
| 5.23 | H | CH$_2$CH$_2$N(CH$_3$)$_2$ | 0 | | |
| 5.24 | H | OCH$_3$ | 0 | | |
| 5.25 | H | 1-naphthyl | 0 | | |
| 5.26 | H | CH$_2$-pyrrolidin-1-yl | 0 | | |

TABLE 5-continued

| | | | |
|---|---|---|---|
| 5.27 | H | 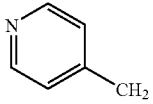 | 0 |
| 5.28 | CH₂CH₂OH | CH₂CH₂OH | 0 |
| 5.29 | H | CH₂CH₂NH₂ | 0 |
| 5.30 | | CH₂(CH₂)₃CH₂ | 0 |
| 5.31 | H | CH₂(CH₂)₃NH₂ | 0 |
| 5.32 | H | CH₂(CH₂)₅NH₂ | 0 |
| 5.33 | H | CH₂(CH₂)₂O(CH₂)₃NH₂ | 0 |
| 5.34 | | CH₂(CH₂)₂CH₂ | 0 |
| 5.35 | H | 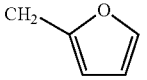 | 0 |
| 5.36 | H | 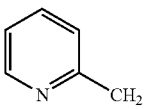 | 0 |
| 5.37 | H | CH₂CH₂NHCH₃ | 0 |
| 5.38 | H | —CH₂C≡CH | 0 |
| 5.39 | H | CH₂(CH₂)₂Cl | 0 |
| 5.40 | H | CH₂CH₂N⁺Me₃I⁻ | 0 |
| 5.41 | CH₂CH₃ | CH₂CH₃ | 0 |
| 5.42 | H | NH₂ | 0 |
| 5.43 | H | NHMe | 0 |
| 5.44 | H | NMe₂ | 0 |
| 5.45 | H | NHOMe | 0 |
| 5.46 | H | CH₂CH₂OS(O)₂NH₂ | 0 |
| 5.47 | H | OH | 0 |
| 5.48 | H | S(O)₂NHBenzyl | 0 |
| 5.49 | H | S(O)₂NH₂ | 0 |
| 5.50 | H | S(O)₂NHPhenyl | 0 |
| 5.51 | H | pMeOC₆H₅ | 0 |
| 5.52 | H | (CH₂)₁₂NH₂ | 0 |
| 5.53 | H | 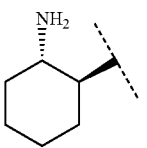 | 0 |
| 5.54 | H | CH(CH₃)CH₂CH₃ | 0 |
| 5.55 | H | (CH₂)₄N⁺Me₃I⁻ | 0 |
| 5.56 | H | (CH₂)₆N⁺Me₃I⁻ | 0 |
| 5.57 | H | (CH₂)₃O(CH₂)₃N⁺Me₃I⁻ | 0 |
| 5.58 | H | (CH₂)₁₂N⁺Me₃I⁻ | 0 |
| 5.59 | H | 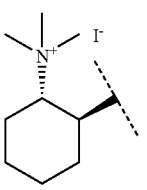 | 0 |
| 5.60 | H | 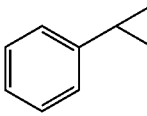 | 0 |
| 5.61 | H | H | 0 |
| 5.62 | H | pNO₂C₆H₅ | 1 |
| 5.63 | H | CH₃ | 1 |
| 5.64 | H | CH₃CH₂ | 1 |
| 5.65 | H | Cyclo-C₅H₉ | 1 |
| 5.66 | H | CH₂CH(CH₃)₂ | 1 |
| 5.67 | H | CH₂C₆H₅ | 1 |

TABLE 5-continued

| | | | | | |
|---|---|---|---|---|---|
| 5.68 | H | Cyclo-C$_6$H$_{11}$ | 1 | | |
| 5.69 | H | CH$_2$(CH$_2$)$_4$CH$_3$ | 1 | | |
| 5.70 | H | CH$_2$CH$_2$CH$_3$ | 1 | | |
| 5.71 | H | CH$_2$CH$_2$OCH$_3$ | 1 | | |
| 5.72 | H | CH(CH$_3$)$_2$ | 1 | | |
| 5.73 | H | CH$_2$(CH$_2$)$_2$OCH$_2$CH$_3$ | 1 | | |
| 5.74 | H | CH$_2$CH=CH$_2$ | 1 | | |
| 5.75 | H | CH$_2$-(tetrahydrofuran-2-yl) | 1 | | |
| 5.76 | H | CH$_2$CH$_2$OH | 1 | | |
| 5.77 | H | CH(CH$_3$)CH(OCH$_3$)$_2$ | 1 | | |
| 5.78 | H | Cyclopropyl | 1 | | |
| 5.79 | H | CH$_2$CH(OH)CH$_2$OH | 1 | | |
| 5.80 | H | CH$_2$CH(OCH$_3$)$_2$ | 1 | | |
| 5.81 | | CH$_2$CH$_2$OCH$_2$CH$_2$ | 1 | | |
| 5.82 | H | CH$_2$CH$_2$F | 1 | | |
| 5.83 | H | CH$_2$CF$_3$ | 1 | | |
| 5.84 | H | CH$_2$CH$_2$N(CH$_3$)$_2$ | 1 | | |
| 5.85 | H | OCH$_3$ | 1 | | |
| 5.86 | H | 1-naphthyl | 1 | | |
| 5.87 | H | CH$_2$-(pyrrolidin-1-yl) | 1 | | |
| 5.88 | H | CH$_2$-(pyridin-4-yl) | 1 | | |
| 5.89 | CH$_2$CH$_2$OH | CH$_2$CH$_2$OH | 1 | | |
| 5.90 | H | CH$_2$CH$_2$NH$_2$ | 1 | | |
| 5.91 | | CH$_2$(CH$_2$)$_3$CH$_2$ | 1 | | |
| 5.92 | H | CH$_2$(CH$_2$)$_3$NH$_2$ | 1 | | |
| 5.93 | H | CH$_2$(CH$_2$)$_5$NH$_2$ | 1 | | |
| 5.94 | H | CH$_2$(CH$_2$)$_2$O(CH$_2$)$_3$NH$_2$ | 1 | | |
| 5.95 | | CH$_2$(CH$_2$)$_2$CH$_2$ | 1 | | |
| 5.96 | H | CH$_2$-(furan-2-yl) | 1 | | |
| 5.97 | H | CH$_2$-(pyridin-2-yl) | 1 | | |
| 5.98 | H | CH$_2$CH$_2$NHCH$_3$ | 1 | | |
| 5.99 | H | CH$_2$C≡CH | 1 | | |
| 5.100 | H | CH$_2$(CH$_2$)$_2$Cl | 1 | | |
| 5.101 | H | CH$_2$CH$_2$N$^+$Me$_3$I$^-$ | 1 | | |
| 5.102 | CH$_2$CH$_3$ | CH$_2$CH$_3$ | 1 | | |
| 5.103 | H | NH$_2$ | 1 | 9.18 | 8.38 |
| 5.104 | H | NHMe | 1 | 9.67 | |
| 5.105 | H | NMe$_2$ | 1 | 9.13 | 8.38 |
| 5.106 | H | NHOMe | 1 | | |
| 5.107 | H | CH$_2$CH$_2$OS(O)$_2$NH$_2$ | 1 | | |
| 5.108 | H | OH | 1 | | |
| 5.109 | H | S(O)$_2$NHBenzyl | 1 | | |
| 5.110 | H | S(O)$_2$NH$_2$ | 1 | | |
| 5.111 | H | S(O)$_2$NHPhenyl | 1 | | |
| 5.112 | H | pMeOC$_6$H$_5$ | 1 | | |
| 5.113 | H | (CH$_2$)$_{12}$NH$_2$ | 1 | | |
| 5.114 | H | trans-2-methylcyclohexan-1-amine | 1 | | |

TABLE 5-continued

| | | | |
|---|---|---|---|
| 5.115 | H | $CH(CH_3)CH_2CH_3$ | 1 |
| 5.116 | H | $(CH_2)_4N^+Me_3I^-$ | 1 |
| 5.117 | H | $(CH_2)_6N^+Me_3I^-$ | 1 |
| 5.118 | H | $(CH_2)_3O(CH_2)_3N^+Me_3I^-$ | 1 |
| 5.119 | H | $(CH_2)_{12}N^+Me_3I^-$ | 1 |
| 5.120 | H | | 1 |
| 5.121 | H | | 1 |
| 5.122 | $CH_3$ | $CH_3$ | 1 |
| 5.123 | $CH_3$ | $CH_2CH_3$ | 1 |
| 5.124 | $CH_3$ | $n-C_3H_7$ | 1 |
| 5.125 | $CH_3$ | $i-C_3H_7$ | 1 |
| 5.126 | $CH_3$ | $n-C_4H_9$ | 1 |
| 5.127 | $CH_3$ | $i-C_4H_9$ | 1 |
| 5.128 | $CH_3$ | $Sec-C_4H_9$ | 1 |
| 5.129 | $CH_3$ | $t-C_4H_9$ | 1 |
| 5.130 | $CH_3$ | $n-C_5H_{11}$ | 1 |
| 5.131 | $CH_3$ | $n-C_6H_{13}$ | 1 |
| 5.132 | $CH_2CH_3$ | $CH_3$ | 1 |
| 5.133 | $CH_2CH_3$ | $n-C_3H_7$ | 1 |
| 5.134 | $CH_2CH_3$ | $i-C_3H_7$ | 1 |
| 5.135 | $CH_2CH_3$ | $n-C_4H_9$ | 1 |
| 5.136 | $CH_2CH_3$ | $i-C_4H_9$ | 1 |

TABLE 6

Compounds of the formula (Ih)

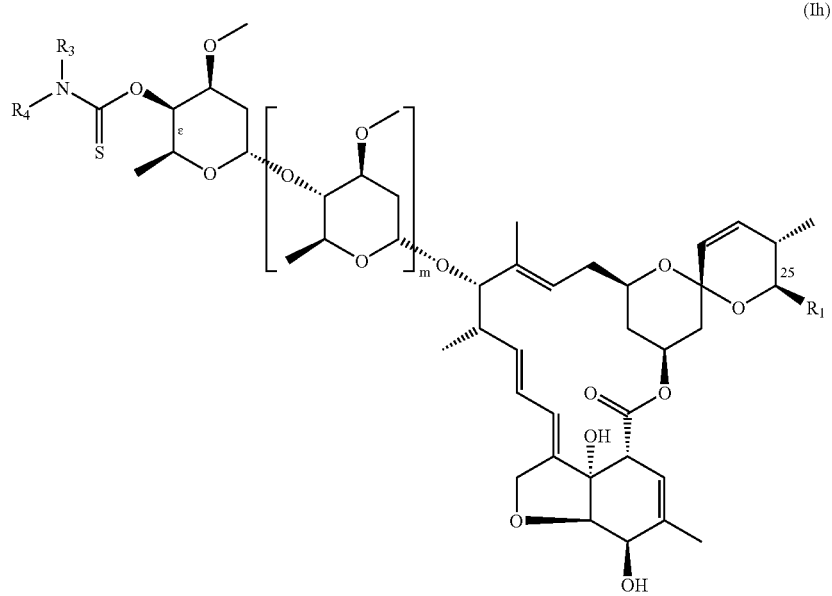

in which $R_1$ is sec-butyl (B1a) or isopropyl (B1b)

| | | | | Retention time (min) | |
|---|---|---|---|---|---|
| No. | $R_3$ | $R_4$ | m | B1a | B1b |
| 6.1 | H | $pNO_2C_6H_5$ | 1 | | |
| 6.2 | H | $CH_3$ | 1 | | |
| 6.3 | H | $CH_3CH_2$ | 1 | | |

TABLE 6-continued

| | | | |
|---|---|---|---|
| 6.4 | H | Cyclo-$C_5H_9$ | 1 |
| 6.5 | H | $CH_2CH(CH_3)_2$ | 1 |
| 6.6 | H | $CH_2C_6H_5$ | 1 |
| 6.7 | H | Cyclo-$C_6H_{11}$ | 1 |
| 6.8 | H | $CH_2(CH_2)_4CH_3$ | 1 |
| 6.9 | H | $CH_2CH_2CH_3$ | 1 |
| 6.10 | H | $CH_2CH_2OCH_3$ | 1 |
| 6.11 | H | $CH(CH_3)_2$ | 1 |
| 6.12 | H | $CH_2(CH_2)_2OCH_2CH_3$ | 1 |
| 6.13 | H | $CH_2CH{=}CH_2$ | 1 |
| 6.14 | H | 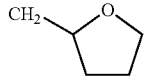 | 1 |
| 6.15 | H | $CH_2CH_2OH$ | 1 |
| 6.16 | H | $CH(CH_3)CH(OCH_3)_2$ | 1 |
| 6.17 | H | Cyclopropyl | 1 |
| 6.18 | H | $CH_2CH(OH)CH_2OH$ | 1 |
| 6.19 | H | $CH_2CH(OCH_3)_2$ | 1 |
| 6.20 | | $CH_2CH_2OCH_2CH_2$ | 1 |
| 6.21 | H | $CH_2CH_2F$ | 1 |
| 6.22 | H | $CH_2CF_3$ | 1 |
| 6.23 | H | $CH_2CH_2N(CH_3)_2$ | 1 |
| 6.24 | H | $OCH_3$ | 1 |
| 6.25 | H | 1-naphthyl | 1 |
| 6.26 | H | 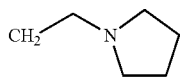 | 1 |
| 6.27 | H | 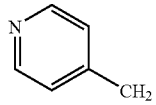 | 1 |
| 6.28 | $CH_2CH_2OH$ | $CH_2CH_2OH$ | 1 |
| 6.29 | H | $CH_2CH_2NH_2$ | 1 |
| 6.30 | | $CH_2(CH_2)_3CH_2$ | 1 |
| 6.31 | H | $CH_2(CH_2)_3NH_2$ | 1 |
| 6.32 | H | $CH_2(CH_2)_5NH_2$ | 1 |
| 6.33 | H | $CH_2(CH_2)_2O(CH_2)_3NH_2$ | 1 |
| 6.34 | | $CH_2(CH_2)_2CH_2$ | 1 |
| 6.35 | H | 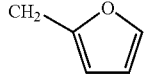 | 1 |
| 6.36 | H | 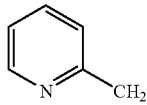 | 1 |
| 6.37 | H | $CH_2CH_2NHCH_3$ | 1 |
| 6.38 | H | $CH_2C{\equiv}CH$ | 1 |
| 6.39 | H | $CH_2(CH_2)_2Cl$ | 1 |
| 6.40 | H | $CH_2CH_2N^+Me_3I^-$ | 1 |
| 6.41 | H | H | 1 |
| 6.42 | $CH_3$ | $CH_3$ | 1 |
| 6.43 | $CH_3$ | $CH_2CH_3$ | 1 |
| 6.44 | $CH_3$ | n-$C_3H_7$ | 1 |
| 6.45 | $CH_3$ | i-$C_3H_7$ | 1 |
| 6.46 | $CH_3$ | n-$C_4H_9$ | 1 |
| 6.47 | $CH_3$ | i-$C_4H_9$ | 1 |
| 6.48 | $CH_3$ | Sec-$C_4H_9$ | 1 |
| 6.49 | $CH_3$ | t-$C_4H_9$ | 1 |
| 6.50 | $CH_3$ | n-$C_5H_{11}$ | 1 |
| 6.51 | $CH_3$ | n-$C_6H_{13}$ | 1 |
| 6.52 | $CH_2CH_3$ | $CH_3$ | 1 |
| 6.53 | $CH_2CH_3$ | n-$C_3H_7$ | 1 |
| 6.54 | $CH_2CH_3$ | i-$C_3H_7$ | 1 |
| 6.55 | $CH_2CH_3$ | n-$C_4H_9$ | 1 |
| 6.56 | $CH_2CH_3$ | i-$C_4H_9$ | 1 |
| 6.57 | H | p$NO_2C_6H_5$ | 0 |
| 6.58 | H | $CH_3$ | 0 |
| 6.59 | H | $CH_3CH_2$ | 0 |

TABLE 6-continued

| | | | |
|---|---|---|---|
| 6.60 | H | Cyclo-$C_5H_9$ | 0 |
| 6.61 | H | $CH_2CH(CH_3)_2$ | 0 |
| 6.62 | H | $CH_2C_6H_5$ | 0 |
| 6.63 | H | Cyclo-$C_6H_{11}$ | 0 |
| 6.64 | H | $CH_2(CH_2)_4CH_3$ | 0 |
| 6.65 | H | $CH_2CH_2CH_3$ | 0 |
| 6.66 | H | $CH_2CH_2OCH_3$ | 0 |
| 6.67 | H | $CH(CH_3)_2$ | 0 |
| 6.68 | H | $CH_2(CH_2)_2OCH_2CH_3$ | 0 |
| 6.69 | H | $CH_2CH=CH_2$ | 0 |
| 6.70 | H | $CH_2$-(tetrahydrofuran-2-yl) | 0 |
| 6.71 | H | $CH_2CH_2OH$ | 0 |
| 6.72 | H | $CH(CH_3)CH(OCH_3)_2$ | 0 |
| 6.73 | H | Cyclopropyl | 0 |
| 6.74 | H | $CH_2CH(OH)CH_2OH$ | 0 |
| 6.75 | H | $CH_2CH(OCH_3)_2$ | 0 |
| 6.76 | | $CH_2CH_2OCH_2CH_2$ | 0 |
| 6.77 | H | $CH_2CH_2F$ | 0 |
| 6.78 | H | $CH_2CF_3$ | 0 |
| 6.79 | H | $CH_2CH_2N(CH_3)_2$ | 0 |
| 6.80 | H | $OCH_3$ | 0 |
| 6.81 | H | 1-naphthyl | 0 |
| 6.82 | H | $CH_2$-(pyrrolidin-1-yl) | 0 |
| 6.83 | H | $CH_2$-(pyridin-4-yl) | 0 |
| 6.84 | $CH_2CH_2OH$ | $CH_2CH_2OH$ | 0 |
| 6.85 | H | $CH_2CH_2NH_2$ | 0 |
| 6.86 | | $CH_2(CH_2)_3CH_2$ | 0 |
| 6.87 | H | $CH_2(CH_2)_3NH_2$ | 0 |
| 6.88 | H | $CH_2(CH_2)_5NH_2$ | 0 |
| 6.89 | H | $CH_2(CH_2)_2O(CH_2)_3NH_2$ | 0 |
| 6.90 | | $CH_2(CH_2)_2CH_2$ | 0 |
| 6.91 | H | $CH_2$-(furan-2-yl) | 0 |
| 6.92 | H | $CH_2$-(pyridin-2-yl) | 0 |
| 6.93 | H | $CH_2CH_2NHCH_3$ | 0 |
| 6.94 | H | $CH_2C\equiv CH$ | 0 |
| 6.95 | H | $CH_2(CH_2)_2Cl$ | 0 |
| 6.96 | H | $CH_2CH_2N^+Me_3I^-$ | 0 |
| 6.97 | H | H | 0 |
| 6.98 | $CH_3$ | $CH_3$ | 0 |
| 6.99 | $CH_3$ | $CH_2CH_3$ | 0 |
| 6.100 | $CH_3$ | n-$C_3H_7$ | 0 |
| 6.101 | $CH_3$ | i-$C_3H_7$ | 0 |
| 6.102 | $CH_3$ | n-$C_4H_9$ | 0 |
| 6.103 | $CH_3$ | i-$C_4H_9$ | 0 |
| 6.104 | $CH_3$ | Sec-$C_4H_9$ | 0 |
| 6.105 | $CH_3$ | t-$C_4H_9$ | 0 |
| 6.106 | $CH_3$ | n-$C_5H_{11}$ | 0 |
| 6.107 | $CH_3$ | n-$C_6H_{13}$ | 0 |
| 6.108 | $CH_2CH_3$ | $CH_3$ | 0 |
| 6.109 | $CH_2CH_3$ | n-$C_3H_7$ | 0 |
| 6.110 | $CH_2CH_3$ | i-$C_3H_7$ | 0 |
| 6.111 | $CH_2CH_3$ | n-$C_4H_9$ | 0 |
| 6.112 | $CH_2CH_3$ | i-$C_4H_9$ | 0 |

TABLE 7
Compounds of the formula
(Ii)
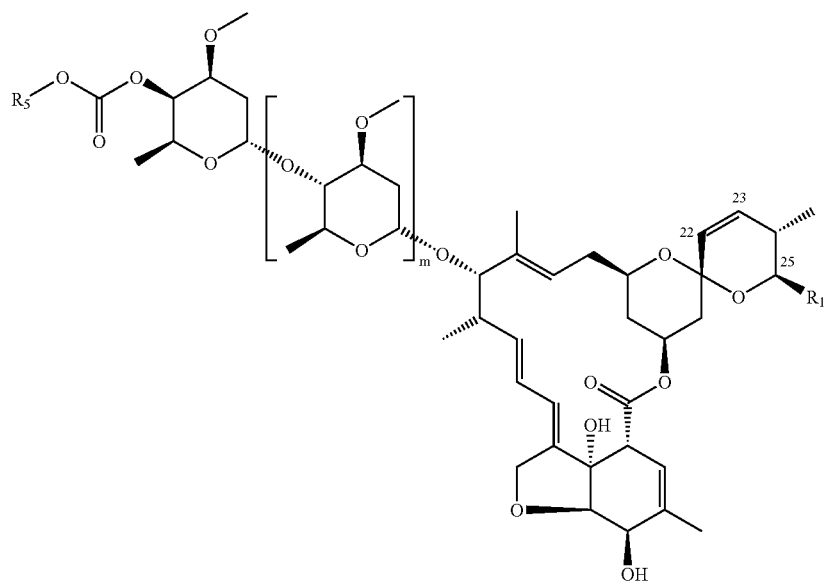
in which $R_1$ is sec-butyl (B1a) or isopropyl (B1b)
| No. | $R_5$ | m | Retention time (min) B1a | Retention time (min) B1b |
|---|---|---|---|---|
| 7.1 | $CH_3$ | 0 | 8.2 | |
| 7.2 | $CH_3CH_2$ | 0 | | |
| 7.3 | Cyclo-$C_5H_9$ | 0 | | |
| 7.4 | $CH_2CH(CH_3)_2$ | 0 | | |
| 7.5 | $CH_2C_6H_5$ | 0 | | |
| 7.6 | Cyclo-$C_6C_{11}$ | 0 | | |
| 7.7 | $CH_2(CH_2)_4CH_3$ | 0 | | |
| 7.8 | $CH_2CH_2CH_3$ | 0 | | |
| 7.9 | $ClCH_2CH_2$ | 0 | | |
| 7.10 | $CH_3$ | 1 | 10.1 | 9.5 |
| 7.11 | $CH_3CH_2$ | 1 | | |
| 7.12 | Cyclo-$C_5H_9$ | 1 | | |
| 7.13 | $CH_2CH(CH_3)_2$ | 1 | | |
| 7.14 | $CH_2C_6H_5$ | 1 | | |
| 7.15 | Cyclo-$C_6C_{11}$ | 1 | | |
| 7.16 | $CH_2(CH_2)_4CH_3$ | 1 | | |
| 7.17 | $CH_2CH_2CH_3$ | 1 | | |
| 7.18 | $ClCH_2CH_2$ | 1 | 11.0 | 10.4 |
| 7.19 | $CH_2OCH_3$ | 1 | 12.7 | 12.2 |
| 7.20 | $CH_2OCH_3$ | 0 | 11.3 | 10.6 |

TABLE 8
Compounds of the formula
(Ik)
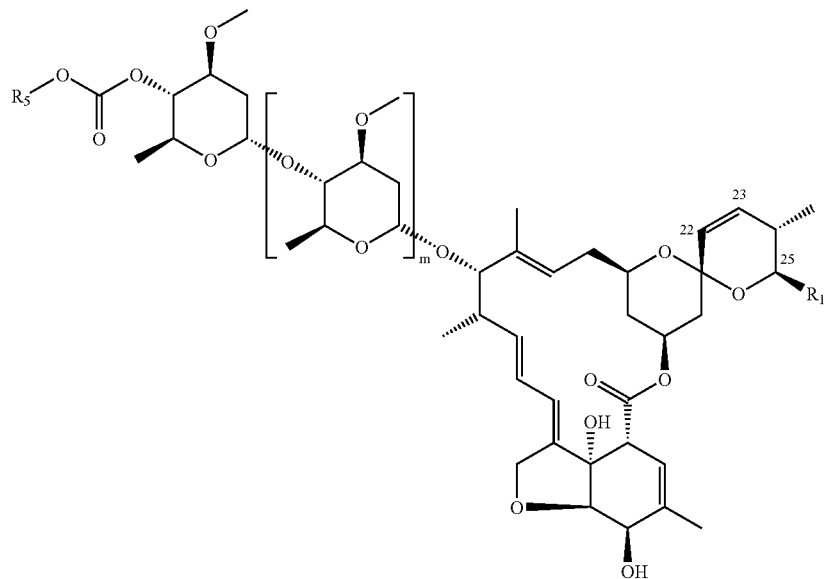
in which $R_1$ is sec-butyl (B1a) or isopropyl (B1b)
| No. | $R_5$ | m | Retention time (min) | |
|---|---|---|---|---|
| | | | B1a | B1b |
| 8.1 | $CH_3$ | 1 | 10.3 | 9.6 |
| 8.2 | $ClCH_2CH_2$ | 1 | 11.4 | 10.8 |
| 8.3 | $CH_2CH=CH_2$ | 1 | 11.41 | |
| 8.4 | $CH_3$ | 0 | 8.9 | |
| 8.5 | $CH_2CH=CH_2$ | 0 | 10.2 | 9.6 |
| 8.6 | $CH_3CH_2$ | 1 | | |
| 8.7 | Cyclo-$C_5H_9$ | 1 | | |
| 8.8 | $CH_2CH(CH_3)_2$ | 1 | | |
| 8.9 | $CH_2C_6H_5$ | 1 | | |
| 8.10 | Cyclo-$C_6C_{11}$ | 1 | | |
| 8.11 | $CH_2(CH_2)_4CH_3$ | 1 | | |
| 8.12 | $CH_2CH_2CH_3$ | 1 | | |
| 8.13 | $CH_2OCH_3$ | 1 | 13.0 | 12.6 |
| 8.14 | $CH_2OCH_3$ | 0 | 11.9 | 11.2 |

TABLE 9
Compounds of the formula
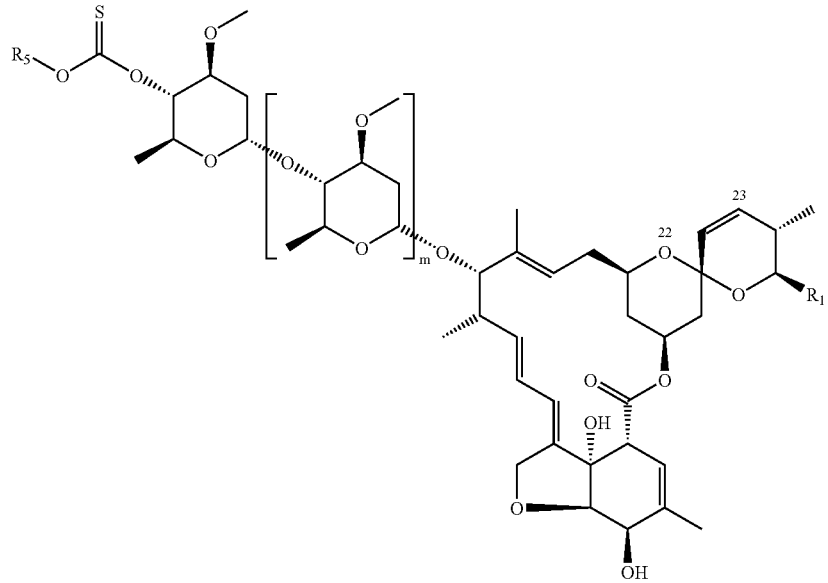
(IL)
in which $R_1$ is sec-butyl (B1a) or isopropyl (B1b)
| No. | $R_5$ | m | Retention time (min) B1a | B1b |
|---|---|---|---|---|
| 9.1 | $CH_2CH_2N_3$ | 0 | 12.8 | 12.3 |
| 9.2 | $CH_2CH_2CH_3$ | 0 | 11.9 | |
| 9.3 | $CH_2CH_2$ | 0 | 11.5 | 11.0 |
| 9.4 | $CH_3$ | 0 | 10.9 | 10.2 |
| 9.5 | $CH_2CH_2CF_3$ | 0 | 12.9 | 12.4 |
| 9.6 | $CH_2CH(CH_3)_2$ | 0 | 12.6 | |
| 9.7 | $CH_2CH_2SCH_2CH_3$ | 0 | 12.1 | |
| 9.8 | $CH_2CF_3$ | 0 | 11.4 | |
| 9.9 | $(CH_2)_2(CF_2)_3CF_3$ | 0 | 13.0 | |
| 9.10 | $CH_2$-cyclopropyl | 0 | 11.7 | |
| 9.11 | $CH_2$-cyclopentyl | 0 | 13.3 | 12.7 |
| 9.12 | $CH_2$-oxiranyl | 0 | 10.4 | |
| 9.13 | $CH_2$-(4-methoxyphenyl) | 0 | 12.4 | 11.9 |
| 9.14 | $-CH_2-C\equiv C-CH_3$ | 0 | 11.8 | 11.1 |
| 9.15 | $CH_2CH_2N_3$ | 1 | | |
| 9.16 | $CH_2CH_2CH_3$ | 1 | | |
| 9.17 | $CH_2CH_2$ | 1 | | |
| 9.18 | $CH_3$ | 1 | | |
| 9.19 | $CH_2CH_2CF_3$ | 1 | | |
| 9.20 | $CH_2CH(CH_3)_2$ | 1 | | |
| 9.21 | $CH_2CH_2SCH_2CH_3$ | 1 | | |
| 9.22 | $CH_2CF_3$ | 1 | | |
| 9.23 | $(CH_2)_2(CF_2)_3CF_3$ | 1 | | |

TABLE 9-continued
| 9.24 | CH₂-cyclopropyl | 1 |
| 9.25 | CH₂-cyclopentyl | 1 |
| 9.26 | CH₂-oxiranyl | 1 |
| 9.27 | CH₂CH₂-(4-methoxyphenyl) | 1 |
| 9.28 | —CH₂—C≡C—CH₃ | 1 |
TABLE 10
Compounds of the formula
(Im)
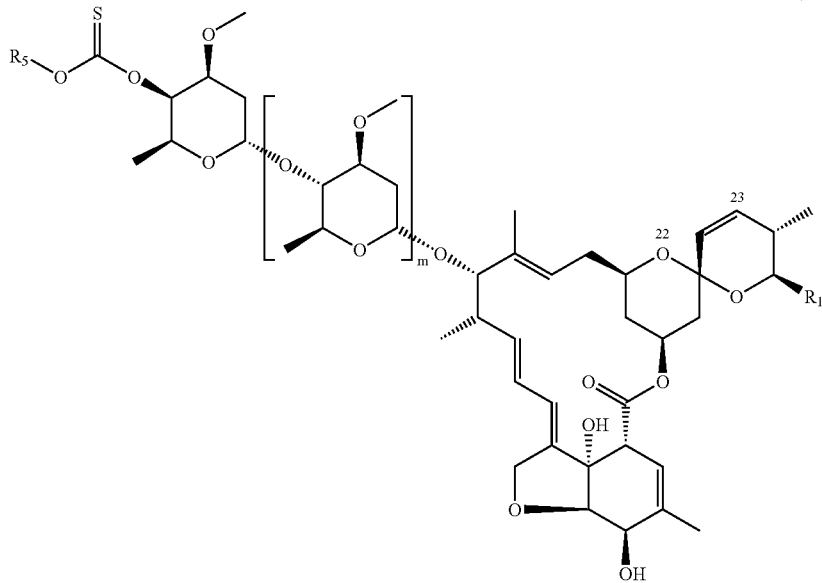
in which $R_1$ is sec-butyl (B1a) or isopropyl (B1b)
| No. | $R_5$ | m | Retention time (min) B1a | B1b |
|---|---|---|---|---|
| 10.1 | $CH_2CH_2N_3$ | 0 | | |
| 10.2 | $CH_2CH_2CH_3$ | 0 | | |
| 10.3 | $CH_2CH_2$ | 0 | | |
| 10.4 | $CH_3$ | 0 | | |
| 10.5 | $CH_2CH_2CF_3$ | 0 | | |
| 10.6 | $CH_2CH(CH_3)_2$ | 0 | | |
| 10.7 | $CH_2CH_2SCH_2CH_3$ | 0 | | |
| 10.8 | $CH_2CF_3$ | 0 | | |
| 10.9 | $(CH_2)_2(CF_2)_3CF_3$ | 0 | | |
| 10.10 | CH₂-cyclopropyl | 0 | | |

TABLE 10-continued

| | | |
|---|---|---|
| 10.11 | cyclopentyl-CH₂— | 0 |
| 10.12 | (epoxide)-CH₂— | 0 |
| 10.13 | 4-methoxyphenyl-CH₂CH₂— | 0 |
| 10.14 | —CH₂—C≡C—CH₃ | 0 |
| 10.15 | CH₂CH₂N₃ | 1 |
| 10.16 | CH₂CH₂CH₃ | 1 |
| 10.17 | CH₂CH₂ | 1 |
| 10.18 | CH₃ | 1 |
| 10.19 | CH₂CH₂CF₃ | 1 |
| 10.20 | CH₂CH(CH₃)₂ | 1 |
| 10.21 | CH₂CH₂SCH₂CH₃ | 1 |
| 10.22 | CH₂CF₃ | 1 |
| 10.23 | (CH₂)₂(CF₂)₃CF₃ | 1 |
| 10.24 | cyclopropyl-CH₂— | 1 |
| 10.25 | cyclopentyl-CH₂— | 1 |
| 10.26 | (epoxide)-CH₂— | 1 |
| 10.27 | 4-methoxyphenyl-CH₂CH₂— | 1 |
| 10.28 | —CH₂—C≡C—CH₃ | 1 |

Table 11: Compounds of the formula (Ic), wherein $R_1$ is Cyclohexyl and the combination of the substituents $R_3$ and $R_4$ for each compound corresponds to a line 1.1 to 1.92 of Table 1.

Table 12: Compounds of the formula (Ic), wherein $R_1$ is 1-methyl-butyl and the combination of the substituents $R_3$ and $R_4$ for each compound corresponds to a line 1.1 to 1.92 of Table 1.

Table 13: Compounds of the formula (Id), wherein $R_1$ is Cyclohexyl and the combination of the substituents $R_3$ and $R_4$ for each compound corresponds to a line 2.1 to 2.89 of Table 2.

Table 14: Compounds of the formula (Id), wherein $R_1$ is 1-methyl-butyl and the combination of the substituents $R_3$ and $R_4$ for each compound corresponds to a line 2.1 to 2.89 of Table 2.

Table 15: Compounds of the formula (Ie), wherein $R_1$ is Cyclohexyl and the combination of the substituents $R_3$ and $R_4$ for each compound corresponds to a line 3.1 to 3.86 of Table 3.

Table 16: Compounds of the formula (Ie), wherein $R_1$ is 1-methyl-butyl and the combination of the substituents $R_3$ and $R_4$ for each compound corresponds to a line 3.1 to 3.86 of Table 3.

Table 17: Compounds of the formula (If), wherein $R_1$ is Cyclohexyl and the combination of the substituents $R_3$ and $R_4$ for each compound corresponds to a line 4.1 to 4.79 of Table 4.

Table 18: Compounds of the formula (If), wherein $R_1$ is 1-methyl-butyl and the combination of the substituents $R_3$ and $R_4$ for each compound corresponds to a line 4.1 to 4.79 of Table 4.

Table 19: Compounds of the formula (Ig), wherein $R_1$ is Cyclohexyl and the combination of $R_3$, $R_4$ and m for each compound corresponds to a line 5.1 to 5.136 of Table 5.

Table 20: Compounds of the formula (Ig), wherein $R_1$ is 1-methyl-butyl and the combination of $R_3$, $R_4$ and m for each compound corresponds to a line 5.1 to 5.136 of Table 5.

Table 21: Compounds of the formula (Ih), wherein $R_1$ is Cyclohexyl and the combination of $R_3$, $R_4$ and m for each compound corresponds to a line 6.1 to 6.112 of Table 6.

Table 22: Compounds of the formula (Ih), wherein $R_1$ is 1-methyl-butyl and the combination of $R_3$, $R_4$ and m for each compound corresponds to a line 6.1 to 6.112 of Table 6.

Table 23: Compounds of the formula (Ii), wherein $R_1$ is Cyclohexyl and the combination of $R_5$ and m for each compound corresponds to a line 7.1 to 7.20 of Table 7.

Table 24: Compounds of the formula (Ii), wherein $R_1$ is 1-methyl-butyl and the combination of $R_5$ and m for each compound corresponds to a line 7.1 to 7.20 of Table 7.

Table 25: Compounds of the formula (Ik), wherein $R_1$ is Cyclohexyl and the combination of $R_5$ and m for each compound corresponds to a line 8.1 to 8.14 of Table 8.

Table 26: Compounds of the formula (Ik), wherein $R_1$ is 1-methyl-butyl and the combination of $R_5$ and m for each compound corresponds to a line 8.1 to 8.14 of Table 8.

Table 27: Compounds of the formula (IL), wherein $R_1$ is Cyclohexyl and the combination of $R_5$ and m for each compound corresponds to a line 9.1 to 9.28 of Table 9.

Table 28: Compounds of the formula (IL), wherein $R_1$ is 1-methyl-butyl and the combination of $R_5$ and m for each compound corresponds to a line 9.1 to 9.28 of Table 9.

Table 29: Compounds of the formula (Im), wherein $R_1$ is Cyclohexyl and the combination of $R_5$ and m for each compound corresponds to a line 10.1 to 10.28 of Table 10.

Table 30: Compounds of the formula (Im), wherein $R_1$ is 1-methyl-butyl and the combination of $R_5$ and m for each compound corresponds to a line 10.1 to 10.28 of Table 10.

Formulation examples for use in crop protection (%=percent by weight)

Example F1

Emulsifiable Concentrates

|  | a) | b) | c) |
|---|---|---|---|
| Active compound | 25% | 40% | 50% |
| Calcium dodecylbenzenesulphonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

Mixing of finely ground active compound and additives gives an emulsion concentrate which, by dilution with water, affords emulsions of the desired concentration.

Example F2

Solutions

|  | a) | b) | c) | d) |
|---|---|---|---|---|
| Active compound | 80% | 10% | 5% | 95% |
| Ethylene glycol monomethyl ether | — | 20% | — | — |
| Polyethylene glycol (MW 400) | — | 70% | — | — |
| N-methylpyrrolid-2-one | 20% | — | — | — |
| Epoxidized coconut oil | — | — | 1% | — |
| Aliphatic hydrocarbon (boiling range: 160-190°) | — | — | 94% | 5% |

Mixing of finely ground active compound and additives gives a solution suitable for use in the form of microdrops.

Example F3

Granules

|  | a) | b) | c) | d) |
|---|---|---|---|---|
| Active compound | 5% | 10% | 8% | 21% |
| Kaolin | 94% | — | 79% | 54% |
| Finely divided silicic acid | 1% | — | 13% | 7% |
| Attapulgite | — | 90% | — | 18% |

The active compound is dissolved in dichloromethane, the solution is sprayed onto the mixture of carriers and the solvent is evaporated under reduced pressure.

Example F4

Wettable Powder

|  | a) | b) | c) |
|---|---|---|---|
| Active compound | 25% | 50% | 75% |
| Sodium lignosulphonate | 5% | 5% | — |
| Sodium lauryl sulphate | 3% | — | 5% |
| Sodium diisobutylnaphthalene sulphonate | — | 6% | 10% |
| Octylphenol polyethylene glycol ether (7-8 mol of EO) | — | 2% | — |
| Finely divided silicic acid | 5% | 10% | 10% |
| Kaolin | 62% | 27% | — |

Active compound and additives are mixed and the mixture is ground in a suitable mill. This gives wettable powders which can be diluted with water to give suspensions of the desired concentration.

Example F5

Emulsifiable Concentrate

| Active compound | 10% |
|---|---|
| Octylphenol polyethylene glycol ether (4-5 mol of EO) | 3% |
| Calcium dodecylbenzenesulphonate | 3% |
| Castor oil polyethylene glycol ether (36 mol of EO) | 4% |
| Cyclohexanone | 30% |
| Xylene mixture | 50% |

Mixing of finely ground active compound and additives gives an emulsion concentrate which, by dilution with water, affords emulsions of the desired concentration.

Example F6

Extruder Granules

| | |
|---|---|
| Active compound | 10% |
| Sodium lignosulphonate | 2% |
| Carboxymethylcellulose | 1% |
| Kaolin | 87% |

Active compound and additives are mixed, the mixture is ground, moistened with water, extruded and granulated, and the granules are dried in a stream of air.

Example F7

Coated Granules

| | |
|---|---|
| Active compound | 3% |
| Polyethylene glycol (MW 200) | 3% |
| Kaolin | 94% |

In a mixer, the finely ground active compound is applied uniformly to the kaolin which has been moistened with polyethylene glycol. This gives dust-free coated granules.

Example F8

Suspension Concentrate

| | |
|---|---|
| Active compound | 40% |
| Ethylene glycol | 10% |
| Nonylphenol polyethylene glycol ether (15 mol of EO) | 6% |
| Sodium lignosulphonate | 10% |
| Carboxymethylcellulose | 1% |
| Aqueous formaldehyde solution (37%) | 0.2% |
| Aqueous silicone oil emulsion (75%) | 0.8% |
| Water | 32% |

Mixing of finely ground active compound and additives gives a suspension concentrate which, by dilution with water, affords suspensions of the desired concentration.

Biological Examples

Example B1

Activity Against *Spodoptera littoralis*

Young soya bean plants are sprayed with an aqueous emulsion spray liquor which comprises 12.5 ppm of active compound, and, after the spray coating has dried on, populated with 10 caterpillars of the first stage of *Spodoptera littoralis* and introduced into a plastic container. 3 days later, the reduction in the population in percent and the reduction in the feeding damage in percent (% activity) are determined by comparing the number of dead caterpillars and the feeding damage between the treated and the untreated plants.

In this test, the compounds of the tables show good activity. Thus, in particular compound numbers 1.1, 1.4, 1.22, 1.31, 1.41, 1.44, 1.46, 2.2, 2.3, 2.26, 2.27, 3.5, 3.10, 3.17, 4.2, 4.17, 5.2, 5.105, 9.3 and 9.4 effect a reduction in the pest population by more than 80%.

Example B2

Activity Against *Spodoptera littoralis*, Systemic

Maize seedlings are placed into the test solution which comprises 12.5 ppm of active compound. After 6 days, the leaves are cut off, placed onto moist filter paper in a Petri dish and populated with 12 to 15 *Spodoptera littoralis* larvae of the L, stage. 4 days later, the reduction of the population in percent (% activity) is determined by comparing the number of dead caterpillars between the treated and the untreated plants.

In this test, the compounds of the tables show good activity. Thus, in particular compound numbers 1.22, 1.31, 1.41, 1.46, 5.105 and 8.4, 9.4 effect a reduction in the pest population by more than 80%.

Example B3

Activity Against *Heliothis virescens*

35 0- to 24-hour-old eggs of *Heliothis virescens* are placed onto filter paper in a Petri dish on a layer of synthetic feed. 0.8 ml of the test solution which comprises 12.5 ppm of active compound, is then pipetted onto the filter papers. Evaluation is carried out after 6 days. The reduction in the population in percent (% activity) is determined by comparing the number of dead eggs and larvae on the treated and the untreated filter papers.

In this test, the compounds of the tables show good activity. Thus, in particular compound numbers 1.30, 3.2, 3.4, 3.5, 3.9, 3.10, 3.17, 4.2, 4.11, 9.4 and 9.10 effect a reduction in the pest population by more than 80%.

Example B4

Activity Against *Plutella xylostella* Caterpillars

Young cabbage plants are sprayed with an aqueous emulsion spray liquor which comprises 12.5 ppm of the active compound. After the spray coating has dried on, the cabbage plants are populated with 10 caterpillars of the first stage of *Plutella xylostella* and introduced into a plastic container. Evaluation is carried out after 3 days. The reduction in the population in percent and the reduction in the feeding damage in percent (% activity) are determined by comparing the number of dead caterpillars and the feeding damage on the treated and the untreated plants.

In this test, the compounds of the tables show good activity against *Plutella xylostella*. Thus, in particular compound numbers 1.1, 1.15, 1.23, 1.26, 1.42, 2.10, 2.11, 2.14, 2.15, 2.66, 3.3, 3.13, 4.5, 4.9, 7.1 and 9.4 effect a reduction in the pest population by more than 80%.

Example B5

Activity Against *Frankliniella occidentalis*

In Petri dishes, discs of the leaves of beans are placed onto agar and sprayed with test solution which comprises 12.5 ppm of active compound, in a spraying chamber. The leaves are then populated with a mixed population of *Frankliniella occidentalis*. Evaluation is carried out after 10 days. The reduction in percent (% activity) is determined by comparing the population on the treated leaves with that of the untreated leaves.

In particular compound numbers 1.1, 1.24, 1.40, 2.14, 2.3, 2.11, 2.15, 2.17, 2.66, 3.21, 4.17, 5.2, 5.9, 8.5, 9.4 and 9.6 effect a reduction in the pest population by more than 80%.

Example B6

Activity Against *Diabrotica balteata*

Maize seedlings are sprayed with an aqueous emulsion spray liquor which comprises 12.5 ppm of active compound and, after the spray coating has dried on, populated with 10 larvae of the second stage of *Diabrotica balteata* and then introduced into a plastic container. After 6 days, the reduction in the population in percent (% activity) is determined by comparing the dead larvae between the treated and the untreated plants.

In this test, the compounds of the tables show good activity. Thus, in particular compound numbers 1.1, 1.4, 1.21, 1.22, 1.26, 1.45, 1.56, 2.10, 2.14, 3.1, 3.12, 5.10, 7.1 and 8.5 effect a reduction in the pest population by more than 80%.

Example B7

Activity Against *Tetranychus urticae*

Young bean plants are populated with a mixed population of *Tetranychus urticae* and, after 1 day, sprayed with an aqueous emulsion spray liquor which comprises 12.5 ppm of active compound, incubated at 25° C. for 6 days and then evaluated. The reduction in the population in percent (% activity) is determined by comparing the number of dead eggs, larvae and adults on the treated and on the untreated plants.

In this test, the compounds of the tables show good activity. Thus, in particular compound numbers 1.1, 1.2, 1.17, 1.18, 1.33, 1.38, 1.47, 2.66, 3.6, 3.7, 3.21, 4.2, 5.2, 5.13, 7.10, 8.5 and 9.7 effect a reduction in the pest population by more than 80%.

The invention claimed is:

1. A compound of the formula

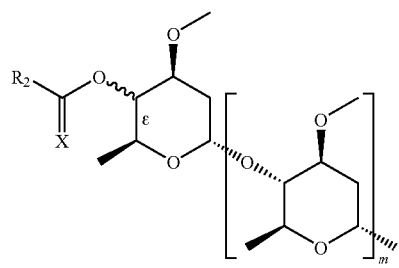

(I)

-continued

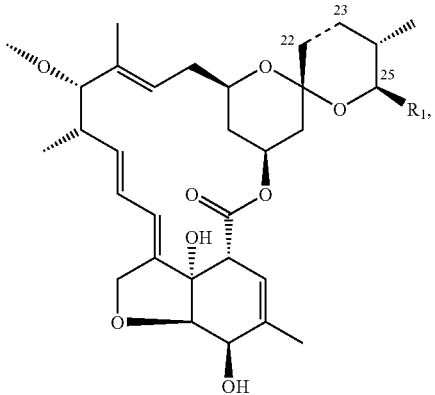

wherein the bond between carbon atoms 22 and 23 is a single or double bond;
m is 0 or 1;
$R_1$ is $C_1$-$C_{12}$alkyl, $C_3$-$C_8$cycloalkyl or $C_2$-$C_{12}$alkenyl; and either
(A) $R_2$ is —N($R_3$)$R_4$, and
  (1) X is O, wherein
    $R_3$ is hydrogen, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, aryl or heterocyclyl, and
    $R_4$ is mono- to pentasubstituted $C_1$-$C_{12}$alkyl, unsubstituted or mono- to penta-substituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted or mono- to trisubstituted heterocyclyl, unsubstituted or mono- to pentasubstituted aryl, $NH_2$, $NHC_1$-$C_{12}$alkyl, $N(C_1$-$C_{12}$alkyl$)_2$, $C_1$-$C_6$alkyl-$N(C_1$-$C_{12}$alkyl$)_2SO_2NH_2$, $SO_2NHC_6H_5$, $SO_2$Phenyl, $SO_2$Benzyl, OH, —$OC_1$-$C_{12}$alkyl, —$OC_1$-$C_{12}$alkenyl or —$OC_1$-$C_{12}$alkynyl; or
  (2) X is S, wherein
    $R_3$ is hydrogen, unsubstituted or mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl; aryl or heterocyclyl, and
    $R_4$ is hydrogen, unsubstituted or mono- to pentasubstituted $C_1$-$C_{12}$alkyl, unsubstituted or mono- to pentasubstituted $C_3$-$Ci_{12}$cycloalkyl, unsubstituted or mono- to pentasubstituted $C_2$-$C_{12}$alkenyl, unsubstituted or mono- to pentasubstituted $C_2$-$C_{12}$alkynyl, unsubstituted or mono- to trisubstituted heterocyclyl, unsubstituted or mono- to pentasubstituted aryl, $NH_2$, $NHC_1$-$C_{12}$alkyl, $N(C_1$-$C_{12}$alkyl$)_2$, $SO_2NH_2$, $SO_2NHC_6H_5$, $SO_2$Phenyl, $SO_2$Benzyl, OH or —$OC_1$-$C_{12}$alkyl; or
  (3) X is O or S, wherein $R_3$ and $R_4$ together are a three- to seven-membered alkylene or a four- to seven-membered alkenylene bridge, in which a $CH_2$ group may be replaced by S, C=O or $NR_6$;
in which the substituents of the alkyl-, alkenyl-, alkynyl-, alkylene-, alkenylene-, heterocyclyl-, aryl- and cycloalkyl-radicals mentioned under $R_3$ and $R_4$ are selected from the group consisting of halogen, halo-$C_1$-$C_2$alkyl, CN, SCN, $NO_2$, $C_2$-$C_6$alkynyl, $C_3$-$C_8$cycloalkyl which is unsubstituted or substituted by one to three methyl groups; norbornylenyl; $C_3$-$C_8$cycloalkenyl which is unsubstituted or substituted by one to three methyl groups; $C_3$-$C_8$halocycloalkyl, $C_1$-$C_{12}$alkoxy, $C_1$-$C_{12}$alkoxy, $C_1$-$C_{12}$alkoxy, $C_3$-$C_8$cycloalkoxy, $C_1$-$C_{12}$alkylthio, $C_3$-$C_8$cycloalkylthio, $C_1$-$C_{12}$haloalkylthio, $C_1$-$C_{12}$alkylsulfinyl, $C_3$-$C_8$cycloalkylsulfinyl, $C_1$-$C_{12}$haloalkylsulfinyl, $C_3$-$C_8$halocycloalkylsulfinyl, $C_1$-$C_{12}$alkylsulfonyl, $C_3$-$C_8$cyclo-alkylsulfonyl, $C_1$-$C_{12}$haloalkylsulfonyl, $C_3$-$C_8$halocycloalkylsulfonyl, $C_2$-$C_8$alkenyl, $C_2$-$C_8$alkynyl, —$N(R_6)_2$, wherein the two $R_6$ are independent of each other; —C(=O)$R_7$, —O—C(=O)$R_8$, —NHC(=O)$R_7$, —S—C(=S)$R_8$, —P(=O)(O$C_1$-$C_6$alkyl)$_2$, —S(=O)$_2R_{11}$; —NH—S(=O)$_2R_{11}$, —OC(=O)—$C_1$-$C_6$alkyl-S(=O)$_2R_{11}$; heterocyclyl, aryloxy, benzyloxy, heterocyclyloxy, arylthio, benzylthio or heterocyclylthio, each of which may be mono- to pentasubstituted by substituents selected from the group consisting of OH, halogen, CN, $NO_2$, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, dimethylamino-$C_1$-$C_6$alkoxy, $C_2$-$C_8$alkenyl, $C_2$-$C_8$alkynyl, phenoxy, phenyl-$C_1$-$C_6$alkyl, methylenedioxy, —C(=O)$R_7$, 13 O—C(=O)—$R_8$, —NH—C(=O)$R_8$, —$N(R_{10})_2$, wherein the two $R_{10}$ are independent of each other; $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cyclo-alkylsulfonyl, $C_1$-$C_6$haloalkylsulfonyl and $C_3$-$C_8$halocycloalkylsulfonyl; or (B) $R_2$ is $OR_5$ and X is O or S, wherein $R_5$ is mono- to pentasubstituted $C_1$-$C_{12}$alkyl, unsubstituted or mono- to pentasubstituted $C_3$-$C_{12}$cycloalkyl, unsubstituted or mono- to pentasubstituted $C_2$-$C_{12}$alkenyl, unsubstituted or mono- to pentasubstituted $C_2$-$C_{12}$alkynyl;

in which the substituents of the alkyl-, alkenyl-, alkynyl and cycloalkyl-radicals mentioned under $R_5$ are selected from the group consisting of OH, CN, SCN, $NO_2$, $C_2$-$C_6$alkynyl, $C_3$-$C_8$cycloalkyl which is unsubstituted or substituted by one to three methyl groups; norbornylenyl; $C_3$-$C_8$cycloalkenyl which is unsubstituted or substituted by one to three methyl groups; $C_3$-$C_8$halocycloalkyl, $C_1$-$C_{12}$alkoxy, $C_1$-$C_{12}$alkoxy$C_1$-$C_{12}$alkoxy, $C_3$-$C_8$cycloalkoxy, $C_1$-$C_{12}$alkylthio, $C_3$-$C_8$cycloalkylthio, $C_1$-$C_{12}$haloalkylthio, $C_1$-$C_{12}$alkylsulfinyl, $C_3$-$C_8$cycloalkylsulfinyl, $C_1$-$C_{12}$haloalkylsulfinyl, $C_3$-$C_8$halocycloalkylsulfinyl, $C_1$-$C_{12}$alkylsulfonyl, $C_3$-$C_8$cycloalkylsulfonyl, $C_1$-$C_{12}$haloalkylsulfonyl, $C_3$-$C_8$halocycloalkylsulfonyl, $C_2$-$C_8$alkenyl, $C_2$-$C_8$alkynyl, —$N(R_6)_2$, wherein the two $R_6$ are independent of each other; —C(=O)$R_7$, —O—C(=O)$R_8$, —NHC(=O)$R_7$, —S—C(=S)$R_8$, —P(=O)(O$C_1$-$C_6$alkyl)$_2$, —S(=O)$_2R_{11}$; —NH—S(=O)$_2R_{11}$, —OC(=O)—$C_1$-$C_6$alkyl-S(=O)$_2R_{11}$; aryl, heterocyclyl, aryloxy, benzyloxy, heterocyclyloxy, arylthio, benzylthio or heterocyclylthio each of which may be mono- to pentasubstituted by substituents selected from the group consisting of OH, halogen, CN, $NO_2$, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, dimethylamino-$C_1$-$C_6$alkoxy, $C_2$-$C_8$alkenyl, $C_2$-$C_8$alkynyl, phenoxy, phenyl-$C_1$-$C_6$alkyl, methylenedioxy, —C(=O)$R_7$, —O—C(=O)—$R_8$, —NH—C(=O)$R_8$, —$N(R_{10})_2$, wherein the two $R_{10}$ are independent of each other; $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl and $C_3$-$C_8$halocycloalkylsulfonyl;

$R_6$ is H, $C_1$-$C_8$alkyl, hydroxy-$C_1$-$C_8$alkyl, $C_3$-$C_8$cycloalkyl, $C_2$-$C_8$alkenyl, $C_2$-$C_8$alkynyl, phenyl, benzyl, —C(=O)$R_7$, or —$CH_2$—C(=O)—$R_7$;

$R_7$ is H, OH, SH, —$N(R_{10})_2$, wherein the two $R_{10}$ are independent of each other; $C_1$-$C_{24}$alkyl, $C_2$-$C_{12}$alkenyl, $C_1$-$C_8$hydroxyalkyl, $C_1$-$C_{12}$haloalkyl, $C_1$-$C_{12}$alkoxy, $C_1$-$C_{12}$haloalkoxy, $C_1$-$C_6$alkoxy-$C_1$-$C_6$alkyl, $C_1$-$C_6$alkoxy-$C_1$-$C_6$alkoxy, $C_1$-$C_6$alkoxy-$C_1$-$C_6$alkoxy-$C_1$-$C_6$alkyl, $C_1$-$C_{12}$alkylthio, $C_2$-$C_8$alkenyloxy, $C_2$-$C_8$alkynyloxy, NH—$C_1$-$C_6$alkyl-C(=O)$R_9$, —$N(C_1$-$C_6$alkyl) -$C_1$-$C_6$alkyl-C(=O)—$R_9$, —O—$C_1$-$C_2$alkyl-C(=O)$R_9$, —$C_1$-$C_6$alkyl-S(=O)$_2R_9$; or aryl, benzyl, heterocyclyl, aryloxy, benzyloxy or heterocyclyloxy, each of which are unsubstituted or mono- to trisubstituted in the ring independently of one another by halogen, nitro, $C_1$-$C_6$alkyl, $C_1$-$C_6$alkoxy, $C_1$-$C_6$haloalkyl or $C_1$-$C_6$haloalkoxy;

$R_8$ is H, $C_1$-$C_{24}$alkyl, $C_1$-$C_{12}$haloalkyl, $C_1$-$C_{12}$hydroxyalkyl, $C_2$-$C_8$alkenyl, $C_2$-$C_8$alkynyl, $C_1$-$C_6$alkoxy-$C_1$-$C_6$alkyl, $N(R_{10})_2$, wherein the two $R_{10}$ are independent of each other; —$C_1$-$C_6$alkyl -C(=O)$R_{10}$, —$C_1$-$C_6$alkyl-S(=O)$_2R_9$, or aryl, benzyl or heterocyclyl, each of which may be mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio;

$R_9$ is H, OH, $C_1$-$C_{24}$alkyl which is optionally subsituted with OH, or —S(=O)$_2$-$C_1$-$C_6$alkyl; $C_1$-$C_{12}$alkenyl, $C_1$-$C_{12}$alkynyl, $C_1$-$C_{12}$alkoxy, $C_1$-$C_6$alkoxy-$C_1$-$C_6$alkyl, $C_1$-$C_6$alkoxy-$C_1$-$C_6$alkoxy, $C_2$-$C_8$alkenyloxy, aryl, aryloxy, benzyloxy, heterocyclyl, heterocyclyloxy or —$N(R_{10})_2$, wherein the two $R_{10}$ are independent of each other;

$R_{10}$ is H, $C_1$-$C_6$alkyl, which is optionally substituted with one to five substituents selected from the group consisting of halogen, $C_1$-$C_6$alkoxy, hydroxy and cyano; $C_1$-$C_8$-cycloalkyl, or aryl, benzyl or heterocyclyl, each of which may be mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio;

or, an E/Z isomer, E/Z isomer mixture and/or tautomer thereof, or a salt thereof.

2. A pesticide composition which contains at least one compound of the formula (I) as described in claim 1 as active compound and at least one auxiliary.

3. A method for controlling pests wherein a composition as defined in claim 2 is applied to the pests or their habitat.

4. A process for preparing a composition as defined in claim 2 which contains at least one auxiliary, wherein the active compound is mixed intimately and/or ground with the auxiliary(s).

5. A method for protecting plant propagation material against damage by a pest, wherein the propagation material or the location where the propagation material is planted is treated with a composition as defined in claim 2.

6. The compound of claim 1, wherein $R_2$ is $-N(R_3)R_4$, and X is O.

7. The compound of claim 1, wherein $R_2$ is $-N(R_3)R_4$, and X is S.

8. The compound of claim 1, wherein $R_2$ is $-N(R_3)R_4$, and X is O or S, wherein $R_3$ and $R_4$ together are a three- to seven-membered alkylene or a four- to seven-membered alkenylene bridge, in which a $CH_2$ group may be replaced by O, S, C=O or $NR_6$.

9. The compound of claim 1, wherein $R_2$ is $OR_5$ and X is O or S.

10. The compound of claim 1, wherein:
$R_2$ is $-N(R_3)R_4$,
X is O;
$R_3$ is hydrogen; and
$R_4$ is mono- to pentasubstituted $C_1$-$C_{12}$alkyl, or unsubstituted or mono- to pentasubstituted $C_3$-$C_{12}$cycloalkyl.

11. The compound of claim 1, wherein:
$R_2$ is $-N(R_3)R_4$,
X is O;
$R_3$ is hydrogen; and
$R_4$ is unsubstituted or mono- to pentasubstituted $C_2$-$C_{12}$alkenyl, or unsubstituted or mono- to pentasubstituted $C_2$-$C_{12}$alkynyl.

12. The compound of claim 1, wherein:
$R_2$ is $-N(R_3)R_4$,
X is O;
$R_3$ is hydrogen; and
$R_4$ is unsubstituted or mono- to trisubstituted heterocyclyl, or unsubstituted and mono- to pentasubstituted aryl.

13. The compound of claim 1, wherein:
$R_2$ is $-N(R_3)R_4$,
X is S;
$R_3$ is hydrogen; and
$R_4$ is hydrogen, mono- to pentasubstituted $C_1$-$C_{12}$alkyl, or unsubstituted or mono- to pentasubstituted $C_3$-$C_{12}$cycloalkyl.

14. The compound of claim 1, wherein:
$R_2$ is $-N(R_3)R_4$,
X is S;
$R_3$ is hydrogen; and
$R_4$ is unsubstituted or mono- to pentasubstituted $C_2$-$C_{12}$alkenyl, or unsubstituted or mono- to pentasubstituted $C_3$-$C_{12}$cycloalkyl.

15. The compound of claim 1, wherein:
$R_2$ is $-N(R_3)R_4$,
X is S;
$R_3$ is hydrogen; and
$R_4$ is unsubstituted or mono- to trisubstituted heterocyclyl unsubstituted, or mono- to pentasubstituted aryl.

16. The compound of claim 1, wherein:
$R_2$ is $OR_5$, and
$R_5$ is mono- to pentasubstituted $C_1$-$C_{12}$alkyl, or unsubstituted or mono- to pentasubstituted $C_3$-$C_{12}$cycloalkyl.

17. The compound of claim 1, wherein:
$R_2$ is $OR_5$, and
$R_5$ is unsubstituted or mono- to pentasubstituted $C_2$-$C_{12}$alkenyl, or unsubstituted or mono- to pentasubstituted alkynyl.

18. The compound of claim 1, wherein the configuration at the $\epsilon$-position is (R).

19. The compound of claim 1, wherein the configuration at the $\epsilon$-position is (S).

\* \* \* \* \*